US009765142B2

(12) United States Patent
Dimitrov et al.

(10) Patent No.: US 9,765,142 B2
(45) Date of Patent: Sep. 19, 2017

(54) TEM8 ANTIBODIES AND THEIR USE IN TREATMENT AND DETECTION OF TUMORS

(71) Applicants: The United States of America, as represented by the Secretary Department of Health and Human Services, Washington, DC (US); BioMed Valley Discoveries, Inc., Kansas City, MO (US)

(72) Inventors: Dimiter Dimitrov, Frederick, MD (US); Zhongyu Zhu, Frederick, MD (US); Brad St. Croix, Frederick, MD (US); Enrique Zudaire, Germantown, MD (US); Saurabh Saha, Wellesley Hills, MA (US); Xiaoyan Michelle Zhang, Lexington, MA (US); Gary Decrescenzo, Parkville, MO (US); Dean Welsch, Parkville, MO (US)

(73) Assignees: The United States of America, as Represented by the Secretary, Department of Health and Human Services, Washington, DC (US); Biomed Valley Discoveries, Inc., Kansas City, MO (US)

( * ) Notice: Subject to any disclaimer, the term of this patent is extended or adjusted under 35 U.S.C. 154(b) by 0 days.

(21) Appl. No.: 15/028,337

(22) PCT Filed: Oct. 13, 2014

(86) PCT No.: PCT/US2014/060299
§ 371 (c)(1),
(2) Date: Apr. 8, 2016

(87) PCT Pub. No.: WO2015/054691
PCT Pub. Date: Apr. 16, 2015

(65) Prior Publication Data
US 2016/0264662 A1    Sep. 15, 2016

Related U.S. Application Data

(60) Provisional application No. 61/889,958, filed on Oct. 11, 2013.

(51) Int. Cl.
| C07K 16/30 | (2006.01) |
| A61P 35/00 | (2006.01) |
| A61K 39/395 | (2006.01) |
| G01N 33/574 | (2006.01) |
| C07K 16/28 | (2006.01) |
| A61K 47/48 | (2006.01) |
| A61K 9/00 | (2006.01) |
| A61K 45/06 | (2006.01) |
| A61K 49/16 | (2006.01) |
| C07K 14/725 | (2006.01) |
| C07K 14/705 | (2006.01) |
| A61K 39/00 | (2006.01) |

(52) U.S. Cl.
CPC ............ *C07K 16/28* (2013.01); *A61K 9/0019* (2013.01); *A61K 39/39558* (2013.01); *A61K 45/06* (2013.01); *A61K 47/48384* (2013.01); *A61K 47/48561* (2013.01); *A61K 47/48569* (2013.01); *A61K 49/16* (2013.01); *C07K 14/7051* (2013.01); *C07K 16/30* (2013.01); *C07K 16/3046* (2013.01); *G01N 33/57419* (2013.01); *A61K 2039/505* (2013.01); *A61K 2039/54* (2013.01); *C07K 2317/21* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,543,210 B2 | 4/2003 | Rostoucher |
| 7,074,913 B2 | 7/2006 | Young et al. |
| 7,393,932 B2 | 7/2008 | Carson-Walter et al. |
| 9,181,340 B2 | 11/2015 | St. Croix et al. |
| 2003/0017157 A1 | 1/2003 | St. Croix et al. |
| 2003/0083263 A1 | 5/2003 | Doronina et al. |

(Continued)

FOREIGN PATENT DOCUMENTS

| CN | 101591395 | 12/2009 |
| WO | WO 02/46228 | 6/2002 |

(Continued)

OTHER PUBLICATIONS

Kuo et al, 2014. Mol Pharmaceutics. 11: 3996-4006.*

(Continued)

*Primary Examiner* — Zachary Howard
(74) *Attorney, Agent, or Firm* — Bryan Cave LLP

(57) ABSTRACT

Antibodies that specifically bind TEM8 protein, conjugates thereof, and their use, are disclosed herein. In some examples the conjugates and antibodies are useful for methods of detecting and treating pathogenic angiogenesis. In other examples the conjugates and antibodies are useful for methods of detecting and treating cancer. In additional examples, the conjugates and antibodies are useful for methods of decreasing binding of Anthrax protective antigen to a cell.

49 Claims, 11 Drawing Sheets

(56) References Cited

U.S. PATENT DOCUMENTS

| | | | |
|---|---|---|---|
| 2003/0220287 | A1 | 11/2003 | Phillips et al. |
| 2005/0196407 | A1 | 9/2005 | Young et al. |
| 2005/0238649 | A1 | 10/2005 | Doronina et al. |
| 2005/0281830 | A1 | 12/2005 | Morrow et al. |
| 2006/0024317 | A1 | 2/2006 | Boyd et al. |
| 2006/0074008 | A1 | 4/2006 | Senter et al. |
| 2006/0083746 | A1 | 4/2006 | Young et al. |
| 2007/0020271 | A1 | 1/2007 | Teicher et al. |
| 2007/0028314 | A1 | 2/2007 | Komori et al. |
| 2007/0258987 | A1 | 11/2007 | Francisco et al. |
| 2008/0305044 | A1 | 12/2008 | McDonagh et al. |
| 2011/0268751 | A1 | 11/2011 | Sievers et al. |
| 2012/0213783 | A1 | 8/2012 | Rosenberg et al. |

FOREIGN PATENT DOCUMENTS

| | | |
|---|---|---|
| WO | WO 2004/010957 | 2/2004 |
| WO | WO 2008/000734 | 1/2008 |
| WO | WO 2012/065161 | 5/2012 |
| WO | WO 2012/079000 | 6/2012 |
| WO | WO 2012/172495 | 12/2012 |
| WO | WO 2012/174160 | 12/2012 |
| WO | WO 2013/059593 | 4/2013 |
| WO | WO 2013/126726 | 8/2013 |

OTHER PUBLICATIONS

Albini, et al. "Cancer prevention by targeting angiogenesis." *Nature Reviews Clinical Oncology* 9, No. 9 (2012): 498-509.

Carson-Walter, et al. "Cell surface tumor endothelial markers are conserved in mice and humans." *Cancer Research* 61, No. 18 (2001): 6649-6655.

Carter, et al. "Antibody-drug conjugates for cancer therapy." *The Cancer Journal*, 14.3 (2008): 154-169.

Chaudhary, et at. "Selective blockade of tumor angiogenesis." *Cell Cycle* 11, No. 12 (2012): 2253-2259.

Chaudhary, et al. "TEM8/ANTXR1 blockade inhibits pathological angiogenesis and potentiates tumoricidal responses against multiple cancer types," *Cancer Cell* 21, No. 2 (2012): 212-226.

Cryan, et al. "Targeting the anthrax receptors, TEM-8 and CMG-2, for anti-angiogenic therapy." *Frontiers in Bioscience; A Journal and Virtual Library*, 16 (2011): 1574-1588.

Cullen, et al. "Host-derived tumor endothelial marker 8 promotes the growth of melanoma." *Cancer Research* 69, No. 15 (2009): 6021-6026.

Davies, et al. "Elevated levels of tumour endothelial marker-8 in human breast cancer and its clinical significance." *International Journal of Oncology*. 29.5 (2006): 1311-1317.

Doronina, et al. "Enhanced activity of monomethylauristatin F through monoclonal antibody delivery: effects of linker technology on efficacy and toxicity." *Bioconjugate Chemistry* 17, No. 1 (2006): 114-124.

Fernando, et al. "Targeting tumor endothelial marker 8 in the tumor vasculature of colorectal carcinomas in mice." *Cancer Research* 69, No. 12 (2009): 5126-5132.

Francisco, et al. "cAC10-vcMMAE, an anti-CD30—monomethyl auristatin E conjugate with potent and selective antitumor activity." *Blood* 102, No. 4 (2003): 1458-1465.

Frankel, et al. "TEM8 Targeted Cancer Therapy." *Anti-Cancer Agents in Medicinal Chemistry (Formerly Current Medicinal Chemistry-Anti-Cancer Agents)* 11, No. 10 (2011): 983-992.

Friedlander. "Macrophages are sensitive to anthrax lethal toxin through an acid-dependent process," *Journal of Biological Chemistry* 261, No. 16 (1986): 7123-7126.

GENBANK® Accession No. AAF86457, as accessed on Apr. 8, 2016.

GENBANK® Accession No. NM_032208.2, as accessed on Apr. 8, 2016.

GENBANK® Accession No. NP_115584.1, as accessed on Apr. 8, 2016.

Grupp, et al. "Chimeric antigen receptor-modified T cells for acute lymphoid leukemia," *New England Journal of Medicine* 368, No. 16 (2013): 1509-1518.

Gutwein, et al. "Tumor endothelial marker 8 expression in triple-negative breast cancer," *Anticancer Research* 31, No. 10 (2011): 3417-3422.

Han, et al. "Chimeric antigen receptor-engineered T cells for cancer immunotherapy: progress and challenges." *J Hematol Oncol* 6, No. 1 (2013): 47.

Hoogenboom. "Designing and optimizing library selection strategies for generating high-affinity antibodies." *Trends in Biotechnology* 15, No. 2 (1997): 62-70.

International Search Report and written opinion for application No. PCT/IB2012/052990, mailed by the International Searching Authority on Oct. 24, 2012.

International Search Report and written opinion for application No. PCT/US2012/042315, mailed by the International Searching Authority on Jul. 30, 2012.

Li, et al. "The inhibition of the interaction between the anthrax toxin and its cellular receptor by an anti-receptor monoclonal antibody." *Biochemical and Biophysical Research Communications* 385 (2009): 591-595.

Lonberg. "Fully human antibodies from transgenic mouse and phage display platforms." *Current Opinion in Immunology*, 20.4 (2008): 450-459.

Maurya, et at. "Expression pattern of tumor endothelial marker 8 protein in gallbladder carcinomas." *Asian Pac J Cancer Prev* 12 (2011): 507-512.

McCarron, et al. "Antibody conjugates and therapeutic strategies." *Molecular Interventions* 5, No. 6 (2005): 368-380.

Moayeri, et al. "The roles of anthrax toxinpathogenesis." *Current Opinion in Microbiology* 7, No. 1 (2004): 19-24.

Nanda, et al. "Identification of a binding partner for the endothelial cell surface proteins TEM7 and TEM7R." *Cancer Research*, 64, No. 23 (2004): 8507-8511.

Nanda, et al., "TEM8 interacts with the cleaved C5 domain of collagen α3 (VI)." *Cancer Research* 64, No. 3 (2004): 817-820.

Nanda et al. "Tumor endothelial markers: new targets for cancer therapy." *Current Opinion in Oncology* 16, No. 1 (2004): 44-49.

Park, et al. "Treating cancer with genetically engineered T cells." *Trends in Biotechnology* 29, No. 11 (2011): 550-557.

Phillips, et al. "Targeting HER2-positive breast cancer with trastuzumab-DM1, an antibody-cytotoxic drug conjugate." *Cancer Research* 68, No. 22 (2008): 9280-9290.

Puri, et al. "Highly efficient selection of epitope specific antibody through competitive yeast display library sorting." in *MAbs*, vol. 5, No. 4, pp. 533-539. Taylor & Francis, 2013.

Rmali, et al. "Identification of microvessels using tumour endothelial marker-8 (TEM-8) in breast cancer and its correlation with tumour progression." *Breast Cancer Research and Treatment*, vol. 88. 233 (2004): p. S144.

Rmali, et al. "Tumour endothelial marker 8 (TEM-8) in human colon cancer and its association with tumour progression." *European Journal of Surgical Oncology (EJSO)*, 30.9 (2004): 948-953.

Scobie, et al. "Human capillary morphogenesis protein 2 functions as an anthrax toxin receptor," *Proceedings of the National Academy of Sciences* 100, No. 9 (2003): 5170-5174.

St. Croix, et al. "Genes expressed in human tumor endothelium." *Science* 289, No. 5482 (2000): 1197-1202.

Van Der Goot, et al, "Receptors of anthrax toxin and cell entry." *Molecular Aspects of Medicine* 30, No. 6 (2009): 406-412.

Wark, et al. "Latest technologies for the enhancement of antibody affinity." *Advanced Drug Delivery Reviews* 58, No. 5 (2006): 657-670.

Yang, et al, "The cell surface structure of tumor endothelial marker 8 (TEM8) is regulated by the actin cytoskeleton." *Biochimica et Biophysica Acta (BBA)—Molecular Cell Research* 1813, No. 1 (2011): 39-49.

Yu, et al. "The biosynthetic gene cluster of the maytansinoid antitumor agent ansamitocin from Actinosynnema pretiosum." *Proceedings of the National Academy of Sciences* 99, No. 12 (2002): 7968-7973.

(56) References Cited

OTHER PUBLICATIONS

Zhao, et al. "Effect of anthrax toxin's lethal factor on ion channels formed by the protective antigen." *Journal of Biological Chemistry* 270, No. 31 (1995): 18626-18630.
Zhu, et al. "Potent neutralization of Hendra and Nipah viruses by human monoclonal antibodies." *Journal of Virology* 80, No. 2 (2006): 891-899.
Zhu, et al. "Quantitative high throughput screening identifies inhibitors of anthrax-induced cell death." *Bioorg Med Chem.*, 17(14) (2009): 5139-5145.

* cited by examiner

FIG. 9 Efficacy of Anti-TEM8 ADC in HCT116 Colon Model

TEM8 ANTIBODIES AND THEIR USE IN TREATMENT AND DETECTION OF TUMORS

CROSS REFERENCE TO RELATED APPLICATIONS

This is the U.S. National Stage of International Application No. PCT/US2014/060299, filed Oct. 13, 2014, which was published in English under PCT Article 21(2), which in turn claims the benefit of U.S. Provisional Application No. 61/889,958, filed Oct. 11, 2013. The provisional application is incorporated by reference herein in its entirety.

PARTIES TO A JOINT RESEARCH AGREEMENT

This invention was made under Public Health Service Cooperative Research and Development Agreement (PHS-CRADA) No. 02744 between the National Institutes of Health National Cancer Institute and Biomed Valley Discoveries, Inc.

FIELD OF THE DISCLOSURE

This application relates to the field of cancer, particularly to antibodies, antigen binding fragments, and conjugates, that specifically bind TEM8 and their use.

BACKGROUND

Angiogenesis, the process of developing a hemovascular network from pre-existing blood vessels, is essential for the growth of solid tumors and is a component of normal wound healing and growth processes. It also has been implicated in the pathophysiology of many diseases and conditions, including atherogenesis, arthritis, psoriasis, corneal neovascularization, and diabetic retinopathy. Angiogenesis factors play an important role in the development of malignancies.

Tumor Endothelial Marker 8 (TEM8), also known as Anthrax Toxin Receptor 1 (ANTXR1), is a single pass, cell surface glycoprotein originally identified, along with a number of other unrelated Tumor Endothelial Markers, based on its over-expression in the endothelial cells that line the tumor vasculature of human colorectal cancer. TEM8 also functions as a cell surface receptor for Anthrax toxin, and shares 58% amino acid identity with CMG2 (also known as ANTXR2), a second receptor for Anthrax toxin protein. Unlike VEGF, VEGFRs, and many other key angiogenesis regulators, TEM8 is not required for developmental angiogenesis, wound healing or normal physiological angiogenesis of the corpus luteum. TEM8 is up-regulated on tumor vessels of various tumor types in both mice and humans, and, in some tumors, is also expressed by the tumor cells. A need exists for chemotherapeutic agents that target TEM8, and for high affinity antibodies that specifically bind TEM8 on the cell surface.

SUMMARY

Isolated human monoclonal neutralizing antibodies that specifically bind to TEM8 on the cell surface, antigen binding fragments of such antibodies, conjugates thereof, chimeric antigen receptor (CAR) T cells expressing a CAR including an extracellular domain including a disclosed antibody or antigen binding fragment thereof, and methods of using these molecules, are provided. In some embodiments, the conjugates include an effector molecule or detectable marker covalently linked to a monoclonal antibody, or an antigen binding fragment thereof, that specifically binds TEM8. In some embodiments, the antibodies or conjugates are used in methods for the detection of an endothelial cell from a subject that expresses TEM8. In some embodiments, detection of an endothelial cell from a subject that expresses TEM8 detects pathological angiogenesis in a subject. In other embodiments, the antibodies and conjugates are used in methods of detecting and/or treating a tumor, for example a carcinoma. In still other embodiments, the antibodies and conjugates are used in methods of decreasing Anthrax protective antigen (PA) binding to a cell.

It will be understood that the antibodies, conjugates, and CAR T cells and methods of their use are useful beyond the specific circumstances that are described in detail herein. For instance, the methods are expected to be useful for a variety of situations, for example to detect an endothelial cell expressing TEM8 in a subject, treat a tumor in a subject or to decrease binding of Anthrax PA to a cell.

The foregoing and features and advantages of the disclosure will become more apparent from the following detailed description, which proceeds with reference to the accompanying figures.

BRIEF DESCRIPTION OF THE FIGURES

FIG. 6A shows bioluminescence imaging of athymic nude mice administered intrasplenic injection of human colon cancer cells. The bioluminescence signal was quantified (FIG. 6B).

SEQUENCE LISTING

Figure 1A:
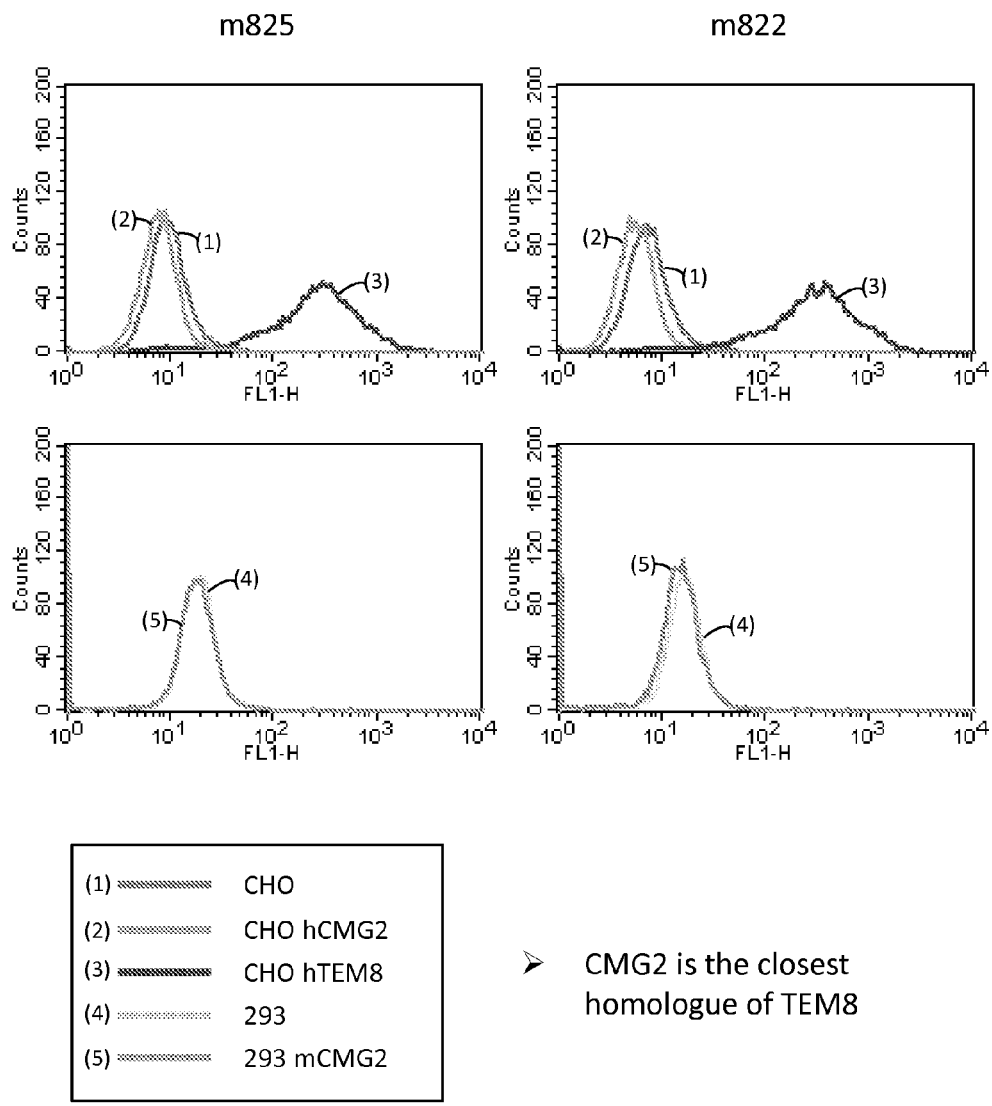
FIGS. 1A and 1B are a series of graphs illustrating the results of flow cytometry assays of the binding of human TEM8 antibodies m825, m822, m830, and m863 to cells expressing TEM8 or CMG2. CMG2 is the closest human homologue of TEM8.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~28 kb), which was created on Mar. 14, 2016, which is incorporated by reference herein. In the accompanying sequence listing:

```
SEQ ID NO: 1 is the amino acid sequence of the heavy chain variable
region of the m825 mAb.
QVQLVQSGAEVKKPGTSVKVSCKVPGYTFSSYAISWVRQAPGQGLEWMGGIIPIFGTTNYAQKFQGRVTI

TGEESTSTVYMELSSLRSEDTAVYYCARDTDYMFDYWGQGTLVTVSS

SEQ ID NO: 2 is the amino acid sequence of the light chain variable
region of the m825 mAb.
SSELTQDPVVSVALGETVSITCQGDNLRDFYASWYQQKPGQAPLLVMYGKNRRPSGIPDRFSGSTSGNTL

SLTITGAQAEDEADYYCSSRDNSKHVVFGGGTKVTVL

SEQ ID NO: 3 is the amino acid sequence of the heavy chain variable
region of the m822 mAb.
QVQLVQSGAEVKKPGASVKVSCKVSGYTFSSYAISWVRQAPGQGLEWMGGIIPIFGTANYAQKFQGRVTI

TADESTSTAYMELSSLRSEDTAVYYCARDTDYMFDYWGQGTLVTVSS

SEQ ID NO: 4 is the amino acid sequence of the light chain variable
region of the m822 mAb.
SSELTQDPVVSVALGETVSITCQGDNLRDFYASWYQQKPGQAPLLVMYGKNRRPSGIPDRFSGSTSGNTL

SLTITGAQAEDEADYYCSSRDNSKHVVFGGGTKVTVL

SEQ ID NO: 5 is the amino acid sequence of the heavy chain variable
region of the m830 mAb.
EVQLVESGGGVVQPGRSVRLSCAASGFTFSTYTMHWVRQAPGKGLEWVAIISNDGSNKYYADPVRGRFTI

SRDNSKNTLYLQMNSLRAEDTAVYYCVRGSSWYRGNWFDPWGQGTLVTVSS

SEQ ID NO: 6 is the amino acid sequence of the light chain variable
region of the m830 mAb.
DIQMTQSPSSLSASVGDRVTIACRASQTISRYLNWYQQKPGKAPKLLIYAASSLQSGVSSRFSGSGSGTE

FTLTISSLQPEDFATYFCQQTYSPPITFGQGTRLEIKR

SEQ ID NO: 7 is the amino acid sequence of the heavy chain variable
region of the m863 mAb.
EVQLVETGAEVKKPGASVKVSCKASGYTFTGYYMHWVRQAPGQGLEWMGWINPTSGSTNYAQKFQGRVTM

TRDTSISTAYMELSGLRSDDTAVYYCVRDPGSPKWLAFDPWGQGTLVTVSS

SEQ ID NO: 8 is the amino acid sequence of the light chain variable
region of the m863 mAb.
DIQLTQSPSSLSASVGDRVTITCRASRAISRYLNWYQQKPGKAPKLLIYAASSLQSGVSSRFSGSGSGTE

FTLTISSLQPEDFATYFCQQTYSPPITFGQGTRLEIKR
```

-continued

SEQ ID NO: 9 is an exemplary cDNA sequence encoding human TEM8 protein (GENBANK ® Accession No. NM_032208.2, incorporated by reference herein as present in the database on Sep. 10, 2013).

SEQ ID NO: 10 is the protein sequence of human TEM8 (GENBANK ® Accession No. NP_115584.1, incorporated by reference herein as present in the database on Sep. 10, 2013).

SEQ ID NO: 11 is an exemplary cDNA sequence encoding the heavy chain variable region of the m825 mAb.
caggtccagctggtgcagtctggggctgaggtgaagaagcctggggacctcagtgaaggtctcctgcaagg ttcctggatacaccttcagcagctatgctatcagctgggtgcgacaggcccctggacaagggcttgagtg gatgggagggatcatccctatctttggtacaacaaactacgcacagaagttccagggcagagtcacgatt accggggaggaatccacgagcacagtctacatggagctgagcagcctgagatctgaggacacggccgtgt attactgtgcgagagatacggactacatgtttgactactggggccagggaacccctggtcaccgtgagctc a SEQ ID NO: 12 is an exemplary cDNA sequence encoding the light chain variable region of the m825 mAb.
tcttctgagctgactcaggaccctgttgtgtctgtggccttgggagagacagtcagtatcacatgccaag gagacaaccctcagagacttttatgcaagctggtaccaacagaagccaggacaggcccctctactagtcat gtatggtaaaaacaggcggccctcagggatcccagaccgattctctggctccacctcaggaaacacactt tccttgaccatcactggggctcaggcggaagatgaggctgactattactgtagctcccgggacaacagta agcatgtggtgttcggcggggggaccaaggtcaccgtccta SEQ ID NO: 13 is an exemplary cDNA sequence encoding the heavy chain variable region of the m822 mAb.
caggtccagctggtgcagtctggggctgaggtgaagaagcctggggcctcagtgaaggtctcctgcaagg tttctggatacaccttcagcagctatgctatcagctgggtgcgacaggcccctggacaagggcttgagtg gatgggagggatcatccctatctttggtacagcaaactacgcacagaagttccagggcagagtcacgatt accgcggacgaatccacgagcacagcctacatggagctgagcagcctgagatctgaggacacggccgtgt attactgtgcgagagatacggactacatgtttgactactggggccagggaacccctggtcaccgtgagctc a SEQ ID NO: 14 is an exemplary cDNA sequence encoding the light chain variable region of the m822 mAb.
tcttctgagctgactcaggaccctgttgtgtctgtggccttgggagagacagtcagtatcacatgccaag gagacaaccctcagagacttttatgcaagctggtaccaacagaagccaggacaggcccctctactagtcat gtatggtaaaaacaggcggccctcagggatcccagaccgattctctggctccacctcaggaaacacactt tccttgaccatcactggggctcaggcggaagatgaggctgactattactgtagctcccgggacaacagta agcatgtggtgttcggcggggggaccaaggtcaccgtccta SEQ ID NO: 15 is an exemplary cDNA sequence encoding the heavy chain variable region of the m830 mAb.
gaggtgcagctggtggagtctgggggaggcgtggtccagcctggggaggtccgtgagactctcctgtgcag cctctggattcaccttcagtacctatactatgcactgggtccgccaggctccaggcaaggggctggagtg ggtggcaattatctcaaatgatggaagcaataagtactacgcagaccccgtgaggggccgattcaccatc tccagagacaattccaagaacacgctgtatctgcaaatgaacagcctgagagctgaggacacggctgtgt attactgtgtacgtggcagcagctggtatcgcggaaattggttcgaccctgggccagggaaccctggt caccgtgagctca SEQ ID NO: 16 is an exemplary cDNA sequence encoding the light chain variable region of the m830 mAb.
gacatccagatgacccagtctccatcctccctgtctgcatctgtaggagacagagtcaccatcgcttgcc gggcaagtcagaccattagtaggtatttaaattggtatcagcagaaaccagggaaagcccctaagctcct -continued
gatctatgctgcatccagtttgcaaagtggggtctcatcaaggttcagtggcagtggatctgggacagag ttcactctcaccatcagcagtctgcagcctgaagattttgcaacttatttctgtcaacagacttacagtc ccccgatcaccttcggccaagggacacgactggagattaaacga SEQ ID NO: 17 is an exemplary cDNA sequence encoding the heavy chain
variable region of the m863 mAb.
gaggtgcagctggtggagaccggggctgaggtgaagaagcctggggcctcagtgaaggtctcctgcaagg cttctggatacaccttcaccggctactatatgcactgggtgcgacaggcccctggacaagggcttgagtg gatgggatggatcaaccctaccagtggtagcacaaactatgcacagaagtttcagggcagggtcaccatg accagggacacgtccatcagcacagcctacatggagctgagcgggctgagatctgacgacactgccgtgt attactgtgtgagagatccgggttctcctaagtggctggccttcgacccctggggccagggcaccctggt caccgtgagctca SEQ ID NO: 18 is an exemplary cDNA sequence encoding the light chain
variable region of the m863 mAb.
gacatccagttgacccagtctccatcctccttgtctgcttctgtaggagacagagtcaccatcacttgcc gggcaagtcgggccattagtaggtatttaaattggtatcagcagaaaccagggaaagcccctaagctcct gatctatgctgcatccagtttgcaaagtggggtctcatcaaggttcagtggcagtggatctgggacagag ttcactctcaccatcagcagtctgcagcctgaagattttgcaacttatttctgtcaacagacttacagtc ccccgatcaccttcggccaagggacacgactggagattaaacgt

DETAILED DESCRIPTION

I. Summary of Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Administration: To provide or give to a subject an agent, for example, a composition that includes a monoclonal antibody that specifically binds TEM8, such as a conjugate, by any effective route. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for decreasing or reducing pathological angiogenesis in a subject. Agents include effector molecules and detectable markers. In some embodiments, the agent is a detectable marker, chemotherapeutic agent, toxin or anti-angiogenic agent. The skilled artisan will understand that particular agents may be useful to achieve more than one result; for example, an agent may be useful as both a detectable marker and an anti-angiogenic agent.

Angiogenesis: A biological process leading to the generation of new blood vessels through sprouting or growth from pre-existing blood vessels. The process involves the migration and proliferation of endothelial cells from preexisting vessels. Angiogenesis occurs during pre- and post-natal development, and in the adult. Angiogenesis occurs during the normal cycle of the female reproductive system, wound healing, and during pathological processes such as cancer, where it is essential for the growth of solid tumors (for review, see Battegay, *J. Molec. Med.*, 73(7): 333-346, 1995; Shchors and Evan, *Cancer Res.*, 67:1630-1633. 2007).

Anthrax: An acute disease caused by the bacterium *Bacillus anthracis*, and in particular the toxin it produces. Anthrax toxin is a mixture of three protein components: (i) protective antigen (PA), (ii) edema factor (EF), and (iii) lethal factor (LF). Cellular entry of Anthrax toxin requires PA binding to one of its two cell-surface receptors, ANTXR1 (aka TEM8) or ANTXR2 (also known as CMG2 receptor), on the host cell (see, for example, Van der Goot and Young, *Mol. Aspects Med.*, 30(6):406-412, 2009; Moayeri and Leppla, *Curr Opin Microbiol* 7(1):19-24, 2004).

Anthrax protective antigen (PA): The protein secreted by *Bacillus anthracis* that forms the Anthrax toxin with edema factor (EF) and lethal factor (LF). Cellular entry of Anthrax toxin requires PA binding to one of its two cell-surface receptors, ANTXR1 (also known as TEM8) or ANTXR2 (also known as CMG2 receptor), on the host cell (see, for example, Van der Goot and Young, *Mol. Aspects Med.*, 30(6):406-412, 2009; Moayeri and Leppla, *Curr Opin Microbiol* 7(1):19-24, 2004). After protease cleavage, PA binds to the two toxic enzymes (EF and LF) and mediates their transportation into the cytosol where they exert their pathogenic effects (Bradley et al., *Nature* 414:225, 2001). The smaller cleaved 63 kD PA remnant ($PA_{63}$) oligomerizes, exposing a second binding domain and binds to either EF, an 89 kD protein, to form edema toxin, or LF, a 90 kD protein, to form lethal toxin (LeTx) (Leppla et al., *Salisbury Med. Bull. Suppl.* 68:41-43, 1990), and the complex is internalized into the cell where it enters the endosomal system (Singh et al., *Infect. Immun.* 67:1853, 1999; Friedlander, *J. Biol. Chem.* 261:7123, 1986). From these endosomes, the $PA_{63}$ channel enables translocation of LF and EF to the cytosol by a pH- and voltage-dependent mechanism (Zhao et al., *J. Biol. Chem.*, 270:18626, 1995). In some embodiments, the TEM8 specific antibodies or conjugates including TEM8 specific antibodies disclosed herein are capable of blocking PA binding to TEM8. In one example, PA includes an amino acid sequence set forth in GENBANK® Accession No. AAF86457, as accessed on Sep. 19, 2013.

Anti-angiogenic agent: A molecule that decreases or reduces angiogenesis, for example, a molecule that decreases pathological angiogenesis. In some examples, antibodies that specifically bind TEM8 or conjugates including such antibodies are anti-angiogenic agents that decrease pathological angiogenesis. Additional anti-angiogenic agents include, but are not limited to, vascular endothelial growth factor (VEGF) antibodies (e.g., bevacizumab) and vascular endothelial growth factor receptor (VEGFR) antibodies (e.g., such as DC101, produced by the DC101 hybridoma (ATCC No. HB-11534)) or small molecules (such as DMXAA (also known as Vadimezan or 5,6-Dimethyl-9-oxo-9H-xanthen-4-yl)-acetic acid, available from Novartis International AG, Basal, CH, and Sigma Corp., St. Louis, Mo.). (See also, Albini et al., *Nat. Rev. Clin. Oncol.*, 9:498-509, 2012).

Antibody: A polypeptide that specifically binds and recognizes an analyte (antigen) such as TEM8 protein or an antigenic fragment of TEM8. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin.* *Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the heavy and light chain variable chains have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, $3^{rd}$ Ed., W.H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the variable domain of the heavy chain of the antibody in which it is found, whereas a $V_L$ CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

A "monoclonal antibody" is an antibody produced by a single clone of B-lymphocytes or by a cell into which nucleic acid encoding the light and heavy variable regions of the antibody of a single antibody (or an antigen binding fragment thereof) have been transfected, or a progeny thereof. Monoclonal antibodies are produced by methods known to those of skill in the art, for instance by making hybrid antibody-forming cells from a fusion of myeloma cells with immune spleen cells. These fused cells and their progeny are termed "hybridomas." In some examples monoclonal antibodies are isolated from a subject. Monoclonal antibodies can have conservative amino acid substitutions which have substantially no effect on antigen binding or other immunoglobulin functions. (See, for example, Harlow & Lane, *Antibodies, A Laboratory Manual*, 2$^{nd}$ ed. Cold Spring Harbor Publications, New York (2013).)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes that are based on sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel*. 1$^{st}$ Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008)

Binding affinity: Affinity of an antibody or antigen binding fragment thereof for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.0 \times 10^{-9}$, at least about $5.0 \times 10^{-9}$, at least about $1.0 \times 10^{-10}$, at least about $5.0 \times 10^{-10}$, or at least about $1.0 \times 10^{-11}$.

Biological sample: A sample obtained from a subject. Biological samples include all clinical samples useful for detection of disease or infection (for example, cancer or Anthrax infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a tumor; for example, a subject having or suspected of having breast, colorectal, lung, or skin cancer. In some examples, the subject has or is suspected of having a carcinoma.

Bispecific antibody: A recombinant molecule composed of two different antigen binding domains that consequently bind to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), eAds, bispecific single chain antibodies or combinations thereof. A bispecific antibody can include one or more constant domains, but does not necessarily include a constant domain. An example of a bispecific antibody is a bispecific single chain antibody including a scFv that specifically binds to TEM8 joined (via a peptide linker) to a scFv that specifically binds to an antigen other than TEM8. Another example is a bispecific antibody including a Fab that specifically binds to TEM8 joined to a scFv that specifically binds to an antigen other than TEM8.

Breast cancer: A neoplastic tumor of breast tissue that is or has potential to be malignant. The most common type of breast cancer is breast carcinoma, such as ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV). See, for example, Bonadonna et al., (eds), *Textbook of Breast Cancer: A clinical Guide the Therapy*. 3$^{rd}$; London, Tayloy & Francis, 2006.

Carcinoma: A malignant tumor including transformed epithelial cells. Non-limiting examples of carcinomas include adenocarcinoma, squamous cell carcinoma, anaplastic carcinoma and large and small cell carcinoma. In some examples, a carcinoma is a breast carcinoma, colorectal carcinoma, lung carcinoma or melanoma.

Chemotherapeutic agent: Any chemical agent with therapeutic usefulness in the treatment of diseases characterized by abnormal cell growth. For example, chemotherapeutic agents are useful for the treatment of cancer, including breast, colorectal, lung, and skin cancer. In one embodiment, a chemotherapeutic agent is an agent of use in treating a carcinoma. Particular examples of additional therapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. In one embodiment, a chemotherapeutic agent is a radioactive compound. Other examples include the anti-neoplastic drugs 5-fluorouracil (5-FU) and IRT. In particular examples, such chemotherapeutic agents are administered in combination with a treatment that decreases or reduces angiogenesis (for example before, during, or after administration of a therapeutically effective amount of one or more antibodies that specifically bind to TEM8 or a conjugate thereof). One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., Chemotherapy, Ch. 17 in Abeloff, Clinical Oncology 2$^{nd}$ ed., © 2000 Churchill Livingstone, Inc; Baltzer, L., Berkery, R. (eds): *Oncology Pocket Guide to Chemotherapy*, 2$^{nd}$ ed. St. Louis, Mosby-Year Book, 1995; Fischer, D. S., Knobf, M. F., Durivage, H J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Willians & Wilkins, 2005; Skeel, *Handbook of Cancer Chemotherapy* (6th ed.). Lippincott Williams & Wilkins, 2003). Combination chemotherapy is the administration of more than one agent to treat cancer.

Chimeric antibody: An antibody which includes sequences derived from two different antibodies, such as from different species. In some examples, a chimeric antibody includes one or more CDRs and/or framework regions from one human antibody and CDRs and/or framework regions from another human antibody.

Chimeric Antigen Receptor (CAR): An engineered T cell receptor having an extracellular antibody-derived targeting domain (such as an scFv) joined to one or more intracellular signaling domains of a T cell receptor. A "chimeric antigen receptor T cell" is a T cell expressing a CAR, and has antigen specificity determined by the antibody-derived targeting domain of the CAR. Methods of making CARs (e.g., for treatment of cancer) are available (see, e.g., Park et al., *Trends Biotechnol.*, 29:550-557, 2011; Grupp et al., N Engl J Med., 368:1509-1518, 2013; Han et al., J. Hematol Oncol., 6:47, 2013; PCT Pubs. WO2012/079000, WO2013/059593; and U.S. Pub. 2012/0213783, each of which is incorporated by reference herein in its entirety.)

Colorectal cancer: A neoplastic tumor of colon, rectum or anus tissue that is or has the potential to be malignant. The main types of colorectal cancer include colorectal carcinomas such as adenocarcinoma and squamous cell carcinoma. Infiltrating (malignant) carcinoma of the colon can be divided into stages (I, II, III and IV). See, for example, Blake et al. (eds.), *Gastrointestinal Oncology: A practical Guide*, Berlin: Springer-Verlag, 2011.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, infra, for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Conjugate: A complex of two molecules linked together, for example, linked together by a covalent bond. In one embodiment, an antibody is linked to an effector molecule; for example, an antibody that specifically binds to TEM8 covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variant: "Conservative" amino acid substitutions are those substitutions that do not substantially decrease the binding affinity of an antibody for an antigen (for example, the binding affinity of an antibody for TEM8). For example, a human antibody that specifically binds TEM8 can include at most about 1, at most about 2, at most about 5, at most about 10, or at most about 15 conservative substitutions and specifically bind the TEM8 polypeptide. The term conservative variation also includes the use of a substituted amino acid in place of an unsubstituted parent amino acid, provided that antibody retains binding affinity for TEM8. Non-conservative substitutions are those that reduce an activity or binding to TEM8.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as tissue sample obtained from a patient that does not have cancer, or a tissue sample from a tissue that is non-cancerous. In other embodiments, the control is a positive control, such as a tissue sample obtained from a patient diagnosed with cancer, or a tissue sample from a cancerous tissue. In still other embodiments, the control is a historical control or standard reference value or range of values (such as a previously tested control sample, such as a group of cancer patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Decrease or Reduce: To reduce the quality, amount, or strength of something; for example a reduction in tumor burden. In one example, a therapy reduces a tumor (such as the size of a tumor, the number of tumors, the metastasis of a tumor, or combinations thereof), or one or more symptoms associated with a tumor (such as pathological angiogenesis of the tumor or tumors), for example as compared to the response in the absence of the therapy. In a particular example, a therapy decreases the size of a tumor, the number of tumors, the metastasis of a tumor, or combinations thereof, subsequent to the therapy, such as a decrease of at least 10%, at least 20%, at least 30%, at least 40%, at least 50%, at least 60%, at least 70%, at least 80%, or at least 90%. Such decreases can be measured using the methods disclosed herein.

Degenerate variant: In the context of the present disclosure, a "degenerate variant" refers to a polynucleotide encoding a protein (for example, an antibody that specifically binds TEM8) that includes a sequence that is degenerate as a result of the genetic code. There are twenty natural amino acids, most of which are specified by more than one codon. Therefore, all degenerate nucleotide sequences are included as long as the amino acid sequence of the antibody that binds TEM8 encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI).

In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, Cold Spring Harbor, N.Y., 2012) and Ausubel et al. (In Current Protocols in Molecular Biology, John Wiley & Sons, New York, through supplement 104, 2013).

Detecting: To identify the existence, presence, or fact of something. General methods of detecting are known to the skilled artisan and may be supplemented with the protocols and reagents disclosed herein. For example, included herein are methods of detecting an endothelial cell that expresses TEM8 in a subject. In some examples, detecting an endothelial cell that expresses TEM8 detects pathological angiogenesis in the subject.

Effective amount: The amount of an agent (such as a TEM8 specific antibody or a conjugate including a TEM8 specific antibody) that alone, or together with one or more additional agents, induces the desired response, such as, for example formation of a detectable immune complex with TEM8.

Effector molecule: A molecule intended to have or produce a desired effect; for example, a desired effect on a cell to which the effector molecule is targeted. Effector molecules include such molecules as polypeptides, radioisotopes and small molecules. Non-limiting examples of effector molecules include toxins, chemotherapeutic agents and anti-angiogenic agents. The skilled artisan will understand that some effector molecules may have or produce more than one desired effect. In one example, an effector molecule is the portion of a chimeric molecule, for example a chimeric molecule that includes a disclosed antibody or fragment thereof, that is intended to have a desired effect on a cell to which the chimeric molecule is targeted.

Endothelial cell: A cell from the endothelium, which is the thin layer of cells that line the interior surface of blood vessels.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on TEM8.

Expressed: Translation of a nucleic acid into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Framework Region: Amino acid sequences interposed between CDRs in a heavy or light variable region of an antibody. Includes variable light and variable heavy framework regions. The framework regions serve to hold the CDRs in an appropriate orientation.

IgA: A polypeptide belonging to the class of antibodies that are substantially encoded by a recognized immunoglobulin alpha gene. In humans, this class or isotype includes $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class includes $IgG_1$, $IgG_2$, $IgG_3$, and IgG. In mice, this class includes $IgG_1$, $IgG_{2a}$, $IgG_{2b}$, and $IgG_3$.

Immune complex: The binding of antibody or antigen binding fragment (such as a scFv) to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Inhibiting or Treating a Disease: A therapeutic intervention (for example, administration of a therapeutically effective amount of an antibody that specifically binds TEM8 or a conjugate thereof) that reduces a sign or symptom of a disease or pathological condition related to a disease (such as a tumor or Anthrax infection). Treatment can also induce remission or cure of a condition, such as a tumor or Anthrax infection. In particular examples, treatment includes preventing a tumor, for example by inhibiting the full development of a tumor, such as preventing development of a metastasis or the development of a primary tumor. Prevention does not require a total absence of a tumor.

Reducing a sign or symptom of a disease or pathological condition related to a disease, refers to any observable beneficial effect of the treatment. Reducing a sign or symptom associated with a tumor (such as pathological angiogenesis) can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having tumor), a reduction in the number of relapses of the disease, an improvement in the overall health or well-being of the subject, or by other parameters well known in the art that are specific to the particular tumor. A "prophylactic" treatment is a treatment administered to a subject who does not exhibit signs of a disease or exhibits only early signs for the purpose of decreasing the risk of developing pathology.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

$K_d$: The dissociation constant for a given interaction, such as a polypeptide ligand interaction or an antibody antigen interaction. For example, for the bimolecular interaction of an antibody or antigen binding fragment (such as 35022 or an antigen binding fragment thereof) and an antigen (such as TWM8 protein) it is the concentration of the individual components of the bimolecular interaction divided by the concentration of the complex.

Linker: A bi-functional molecule that can be used to link two molecules into one contiguous molecule, for example, to link an effector molecule to an antibody. In some embodiments, the provided conjugates include a linker between the effector molecule or detectable marker and an antibody. In some embodiments, the linker is selectively cleavable, for example, cleavable under intracellular conditions, such that cleavage of the linker releases the effector molecule or detectable marker from the antibody in the intracellular environment. Selectively cleavable refers to cleaving in response to a preselected condition or stimulus. In yet other embodiments, the linker is not cleavable and the effector molecule or detectable marker can be released, for example, by antibody degradation. In some cases, a linker is a peptide within an antigen binding fragment (such as an Fv fragment) which serves to indirectly bond the variable heavy chain to the variable light chain.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Lung cancer: A neoplastic tumor of lung tissue that is or has the potential to be malignant. The main types of lung cancer are lung carcinomas: adenocarcinoma, small cell carcinoma, squamous cell carcinoma, or non-small cell carcinoma. Lung cancer is typically staged from I to IV; other classifications are also used, for example small-cell lung carcinoma can be classified as limited stage if it is confined to one half of the chest and within the scope of a single radiotherapy field; otherwise, it is extensive stage. See, for example, Hansen (ed.), Textbook of Lung Cancer, 2$^{nd}$, London: Informa Healthcare, 2008.

Neutralizing antibody: An antibody that is able to specifically bind to a target protein in such a way as to inhibit a biological function associated with that target protein. In general, any protein that can perform this type of specific blocking activity is considered a neutralizing protein; neutralizing antibodies are therefore a specific class of neutralizing protein.

Neoplasia, cancer, or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue or can metastasize (or both) is referred to as "malignant."

Tumors of the same tissue type are primary tumors originating in a particular organ (such as colon, skin, breast, prostate, bladder or lung). Tumors of the same tissue type may be divided into tumors of different sub-types. For examples, lung carcinomas can be divided into an adenocarcinoma, small cell, squamous cell, or non-small cell tumors.

Examples of solid tumors, such as sarcomas (connective tissue cancer) and carcinomas (epithelial cell cancer), include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colorectal carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pathological angiogenesis: Angiogenesis that is medically undesired or harmful to a subject, such as angiogenesis associated with a tumor or the generation of blood vessels in or surrounding a tumor. Tumor vasculature can be distinct from normal vasculature in that several genes can be differentially expressed in tumor-associated blood vessels (St. Croix et al., *Science*, 289, 1197-1202, 2000). One of these genes, tumor endothelial marker 8 (TEM 8), is upregulated in the vasculature of malignant solid tumors, with limited expression in healthy tissues. Other examples of pathological angiogenesis include corneal or retinal angiogenesis (as in a corneal transplant or the retina of a subject with macular degeneration or diabetes).

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed antibodies.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended in a unit dosage form containing one or more measured doses of the composition suitable to induce the desired response. It may also be accompanied by medications for its use for treatment purposes. The unit dosage form may be, for example, in a sealed vial that contains sterile contents or a syringe for injection into a subject.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Polypeptide modifications: Polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation, such as at least 80%, at least 90%, at least 95% or greater of the total peptide or protein content.

Sequence identity: The similarity between amino acid sequences is expressed in terms of the similarity between the sequences, otherwise referred to as sequence identity.

Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Skin cancer: A neoplastic tumor of skin tissue that is or has the potential to be malignant. Melanoma is a skin cancer of transformed melanocytes (cells that make the pigment melanin). Melanocytes are found primary in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism), which is a marker of aggressive behavior and a tendency for local recurrence. Other melanomas include clear cell sarcoma, mucosal melanoma and uveal melanoma. Melanoma is staged from I to IV. See, for example, Thompson et al. (eds), *Textbook of Melanoma: Pathology, Diagnosis and Management*, London: Taylor & Francis, 2004.

Specifically bind: When referring to an antibody, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an epitope of TEM8) and does not bind in a significant amount to other proteins or polysaccharides present in the sample or subject. Specific binding can be determined by methods known in the art. With reference to an antibody antigen complex, specific binding of the antigen and antibody has a $K_d$ of less than about $10^{-7}$ Molar (M), such as less than about $10^{-8}$ M, $10^{-9}$ M, $10^{-10}$ M, or even less than about $10^{-11}$ M.

The antibodies disclosed herein specifically bind only to a defined target (or multiple targets, in the case of a bispecific antibody). Thus, an antibody that specifically binds to TEM8 is an antibody that binds substantially to TEM8, including cells or tissue expressing TEM8, substrate to which the TEM8 is attached, or TEM8 in a biological specimen. It is, of course, recognized that a certain degree of non-specific interaction may occur between an antibody or conjugate including an antibody (such as an antibody that specifically binds TEM8 or conjugate including such antibody) and a non-target (such as a cell that does not express TEM8). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, Antibodies, *A Laboratory Manual*, $2^{nd}$ ed., Cold Spring Harbor Publications, New York (2013), for a description of immunoassay formats and conditions that can be used to determine specific immunoreactivity.

Subject: Any mammal, such as humans, non-human primates, pigs, sheep, cows, rodents, and the like. In two non-limiting examples, a subject is a human subject or a murine subject. Thus, the term "subject" includes both human and veterinary subjects.

T Cell: A white blood cell critical to the immune response. T cells include, but are not limited to, CD4$^+$ T cells and CD8$^+$ T cells. A CD4$^+$ T lymphocyte is an immune cell that expresses CD4 on its surface. These cells, also known as helper T cells, help orchestrate the immune response, including antibody responses as well as killer T cell responses. Th1 and Th2 cells are functional subsets of helper T cells. Th1 cells secrete a set of cytokines, including interferon-gamma, and whose principal function is to stimulate phagocyte-mediated defense against infections, especially related to intracellular microbes. Th2 cells secrete a set of cytokines, including interleukin (IL)-4 and IL-5, and whose principal functions are to stimulate IgE and eosinophil/mast cell-mediated immune reactions and to downregulate Th1 responses.

Therapeutic agent: Used in a generic sense, it includes treating agents, prophylactic agents, and replacement agents. A therapeutic agent is used to ameliorate a specific set of conditions in a subject with a disease or a disorder.

Therapeutically effective amount: The amount of an agent (such as a TEM8 specific antibody or a conjugate including a TEM8 specific antibody) that alone, or together with one or more additional agents, induces the desired response, such as, for example treatment of a tumor, or treatment of Anthrax, in a subject. When administered to a subject, a dosage will generally be used that will achieve target tissue concentrations that has been shown to achieve a desired in vitro effect. Ideally, a therapeutically effective amount provides a therapeutic effect without causing a substantial cytotoxic effect in the subject.

In one example, a desired response is to decrease the size, volume, or number (such as metastases) of a tumor in a subject. For example, the agent or agents can decrease the size, volume, or number of tumors by a desired amount, for example by at least 5%, at least 10%, at least 15%, at least 20%, at least 25%, at least 30%, at least 50%, at least 75%, at least 90%, or at least 95% as compared to a response in the absence of the agent.

Several preparations disclosed herein are administered in therapeutically effective amounts. A therapeutically effective amount of an antibody that specifically binds TEM8 or antigen binding fragment thereof, or conjugate thereof (or a composition including one or more of these molecules) that is administered to a human or veterinary subject will vary depending upon a number of factors associated with that subject, for example the overall health of the subject. A therapeutically effective amount can be determined by varying the dosage and measuring the resulting therapeutic response, such as the regression of a tumor. Therapeutically effective amounts also can be determined through various in vitro, in vivo or in situ immunoassays. The disclosed agents can be administered in a single dose, or in several doses, as needed to obtain the desired response. However, the therapeutically effective amount of can be dependent on the source applied, the subject being treated, the severity and type of the condition being treated, and the manner of administration.

Toxin: An effector molecule that induces cytotoxicity when it contacts a cell. Specific, non-limiting examples of toxins include, but are not limited to, abrin, ricin, auristatins (such as monomethyl auristatin E (MMAE; see for example, Francisco et al., Blood, 102: 1458-1465, 2003)) and monomethyl auristatin F (MMAF; see, for example, Doronina et al., BioConjugate Chem., 17: 114-124, 2006), maytansinoids (such as DM1; see, for example, Phillips et al., Cancer Res., 68:9280-9290, 2008), *Pseudomonas* exotoxin (PE, such as PE35, PE37, PE38, and PE40), diphtheria toxin (DT), botulinum toxin, saporin, restrictocin or gelonin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody.

Transformed: A transformed cell is a cell into which a nucleic acid molecule has been introduced by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Tumor burden: The total volume, number, metastasis, or combinations thereof of tumor or tumors in a subject.

Tumor Endothelial Marker 8 (TEM8): A protein also known as Anthrax Toxin Receptor 1 (ANTXR1). TEM8 is a cell-surface glycoprotein originally identified based on its over-expression in the endothelial cells that line the tumor vasculature of human colorectal cancer (St Croix et al., Science, 289(5482): 1197-1202, 2000). Unlike vascular endothelial growth factor (VEGF), VEGF receptor (VEGFR), and many other key angiogenesis regulators, TEM8 is not required for developmental angiogenesis, wound healing, or normal physiological angiogenesis of the corpus luteum (St Croix et al., Science, 289(5482):1197-1202, 2000; Nanda et al., Cancer Res., 64(3):817-820, 2004). TEM8 is up-regulated on tumor vessels of various tumor types in both mice and humans (Nanda et al., Cancer Res., 64(3):817-820, 2004; Carson-Walter et al., Cancer Res., 61(18):6649-6655, 2001), and in some tumors is also expressed by the tumor cells themselves (Carson-Walter et al. Cancer Res., 61(18):6649-6655, 2001; Yang et al., Biochim Biophys Acta, 1813(1):39-49, 2011). TEM8 also functions as a cell-surface receptor for Anthrax toxin, and shares 58% amino acid identify with CMG2 (also known as ANTXR2), which is a second receptor for Anthrax toxin protein (Scobie et al., Proc. Natl. Acad. Sci. U.S.A., 100(9): 5170-5174, 2003).

TEM8 protein sequence is known (see, for example, GENBANK® Accession No. NP_115584.1, incorporated by reference herein as present in the database on Sep. 10, 2013). Additionally, exemplary nucleic acid sequences encoding TEM8 protein are known (see, for example, GENBANK® Accession No. NM_032208.2, incorporated by reference herein as present in the database on Sep. 10, 2013). In one example, TEM8 is a polypeptide having an amino acid sequence set forth as SEQ ID NO: 10.

Tumor microenvironment: The cellular environment in which a tumor exists, including surrounding blood vessels, immune cells, fibroblasts, signaling molecules, and the extracellular matrix (ECM), including stromal cells. Tumors can influence the microenvironment by releasing extracellular signals, promoting pathological angiogenesis and inducing peripheral immune tolerance, while the immune cells in the microenvironment can affect the growth and evolution of cancerous cells, such as in immuno-editing.

Under conditions sufficient for: A phrase that is used to describe any environment that permits a desired activity. In one example the desired activity is formation of an immune complex. In particular examples the desired activity is treatment of a tumor.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

II. Description of Several Embodiments

Isolated monoclonal antibodies and antigen binding fragments thereof that specifically bind an epitope on TEM8 protein are provided. The antibodies and antigen binding fragments can be fully human. In several embodiments, the antibodies and antigen binding fragments can be used to neutralize HIV-1 infection. Also disclosed herein are compositions including the antibodies and antigen binding fragments and a pharmaceutically acceptable carrier. Nucleic acids encoding the antibodies or antigen binding fragments, expression vectors including these nucleic acids, and isolated host cells that express the nucleic acids are also provided.

Compositions comprising the monoclonal antibodies specific for TEM8 can be used for research, diagnostic and therapeutic purposes. For example, the monoclonal antibodies can be used to diagnose or treat a subject having pathogenic angiogenesis.

A. Antibodies and Antigen Binding Fragments

Isolated monoclonal antibodies and antigen binding fragments that specifically bind an epitope on TEM8 protein and are neutralizing are provided. In several embodiments, the antibodies and antigen binding fragments can neutralize a biological function or property of TEM8 protein in vivo, including, but not limited to, a reduction and/or inhibition of pathological angiogenesis, a reduction and/or inhibition of tumor growth, or a reduction and/or inhibition of tumor metastasis.

In several embodiments, the monoclonal antibodies include a heavy chain comprising a heavy chain complementarity determining region (HCDR)1, a HCDR2 and an HCDR3, and a light chain comprising a light chain complementarity determining region (LCDR) 1, LCDR2 and LCDR3. The disclosed antibodies specifically bind to an epitope of TEM8 and are neutralizing. In some embodiments, the TEM8 specific antibodies include a variable heavy ($V_H$) and a variable light ($V_L$) chain and specifically bind TEM8. In several embodiments, the antibody or antigen binding fragment thereof includes heavy and light chain variable regions including the HCDR1, HCDR2, and HCDR3, and LCDR1, LCDR2, and LCDR3, respectively, of one of the m825, m822, m830, or m863 antibodies.

The discussion of monoclonal antibodies below refers to isolated monoclonal antibodies that include heavy and light chain variable domains including at least one complementarity determining region (CDR), such as a CDR1, CDR2 and CDR3. The person of ordinary skill in the art will understand that various CDR numbering schemes (such as the Kabat, Chothia or IMGT numbering schemes) can be used to determine CDR positions. The amino acid sequence and the CDR positions of the heavy and light chain of the m825, m822, m830, and m863 monoclonal antibodies according to the IMGT and Kabat numbering schemes are shown in Table 1 (IMGT) and Table 2 (Kabat). The person of skill in the art will readily understand use of various CDR numbering schemes when referencing particular amino acids of the antibodies disclosed herein.

TABLE 1

IMGT CDR sequences of TEM8 specific antibodies m825

| | SEQ ID NO: 1 | A.A. Sequence | | SEQ ID NO: 2 | A.A. Sequence |
|---|---|---|---|---|---|
| HCDR1 | 26-33 | GYTFSSYA | LCDR1 | 26-31 | NLRDFY |
| HCDR2 | 51-58 | IIPIFGTT | LCDR2 | 49-51 | GKN |
| HCDR3 | 97-106 | ARDTDYMFDY | LCDR3 | 88-97 | SSRDNSKHVV |

TABLE 1-continued

IMGT CDR sequences of TEM8 specific antibodies m822

| | SEQ ID NO: 3 | A.A. Sequence | | SEQ ID NO: 4 | A.A. Sequence |
|---|---|---|---|---|---|
| HCDR1 | 26-33 | GYTFSSYA | LCDR1 | 26-31 | NLRDFY |
| HCDR2 | 51-58 | IIPIFGTA | LCDR2 | 49-51 | GKN |
| HCDR3 | 97-106 | ARDTDYMFDY | LCDR3 | 88-97 | SSRDNSKHVV | m830

| | SEQ ID NO: 5 | A.A. Sequence | | SEQ ID NO: 6 | A.A. Sequence |
|---|---|---|---|---|---|
| HCDR1 | 26-33 | GFTFSTYT | LCDR1 | 27-32 | QTISRY |
| HCDR2 | 51-58 | ISNDGSNK | LCDR2 | 50-52 | AAS |
| HCDR3 | 97-110 | VRGSSWYRGNWFDP | LCDR3 | 89-97 | QQTYSPPIT | m863

| | SEQ ID NO: 7 | A.A. Sequence | | SEQ ID NO: 8 | A.A. Sequence |
|---|---|---|---|---|---|
| HCDR1 | 26-33 | GYTFTGYY | LCDR1 | 27-32 | RAISRY |
| HCDR2 | 51-58 | INPTSGST | LCDR2 | 50-52 | AAS |
| HCDR3 | 97-110 | VRDPGSPKWLAFDP | LCDR3 | 89-97 | QQTYSPPIT |

In some embodiments, the antibody includes IMGT CDRs, such as those listed in Table 1. For example, in some embodiments, the antibody includes a heavy chain variable region including a HCDR1, HCDR2, and/or HCDR3 including amino acids 26-33, 51-58, and 97-106 of SEQ ID NO: 1, respectively. In further embodiments, the antibody includes a heavy chain variable region including a HCDR1, HCDR2, and/or HCDR3 including amino acids 26-33, 51-58, and 97-106 of SEQ ID NO: 3, respectively. In additional embodiments, the antibody includes a heavy chain variable region including a HCDR1, HCDR2, and/or HCDR3 including amino acids 26-33, 51-58, and 97-110 of SEQ ID NO: 5, respectively. In more embodiments, the antibody includes a heavy chain variable region including a HCDR1, HCDR2, and/or HCDR3 including amino acids 26-33, 51-58, and 97-110 of SEQ ID NO: 7, respectively.

In some embodiments, the antibody includes a light chain variable region including a LCDR1, LCDR2, and/or LCDR3 including amino acids 26-31, 49-51, and 88-97 of SEQ ID NO: 2, respectively. In further embodiments, the antibody includes a light chain variable region including a LCDR1, LCDR2, and/or LCDR3 including amino acids 26-31, 49-51, and 88-97 of SEQ ID NO: 4, respectively. In additional embodiments, the antibody includes a light chain variable region including a LCDR1, LCDR2, and/or LCDR3 including amino acids 27-32, 50-52, and 89-97 of SEQ ID NO: 6, respectively. In more embodiments, the antibody includes a light chain variable region including a LCDR1, LCDR2, and/or LCDR3 including amino acids 27-32, 50-52, and 89-97 of SEQ ID NO: 8, respectively.

In some embodiments, the antibody includes a heavy chain variable region including a HCDR1, HCDR2, and HCDR3 including amino acids 26-33, 51-58, and 97-106 of SEQ ID NO: 1, respectively, and a light chain variable region including a LCDR1, LCDR2, and LCDR3 including amino acids 26-31, 49-51, and 88-97 of SEQ ID NO: 2, respectively. In further embodiments, the antibody includes a heavy chain variable region including a HCDR1, HCDR2, and HCDR3 including amino acids 26-33, 51-58, and 97-106 of SEQ ID NO: 3, respectively, and a light chain variable region including a LCDR1, LCDR2, and LCDR3 including amino acids 26-31, 49-51, and 88-97 of SEQ ID NO: 4, respectively. In additional embodiments, the antibody includes a heavy chain variable region including a HCDR1, HCDR2, and HCDR3 including amino acids 26-33, 51-58, and 97-110 of SEQ ID NO: 5, respectively, and a light chain variable region including a LCDR1, LCDR2, and LCDR3 including amino acids 27-32, 50-52, and 89-97 of SEQ ID NO: 6, respectively. In more embodiments, the antibody includes a heavy chain variable region including a HCDR1, HCDR2, and HCDR3 including amino acids 26-33, 51-58, and 97-110 of SEQ ID NO: 7, respectively, and a light chain variable region including a LCDR1, LCDR2, and LCDR3 including amino acids 27-32, 50-52, and 89-97 of SEQ ID NO: 8, respectively.

TABLE 2

Kabat CDR sequences of TEM8 specific antibodies m825

| | SEQ ID NO: 1 | A.A. Sequence | | SEQ ID NO: 2 | A.A. Sequence |
|---|---|---|---|---|---|
| HCDR1 | 26-32 | GYTFSSY | LCDR1 | 23-33 | QGDNLRDFYAS |
| HCDR2 | 52-57 | IPIFGT | LCDR2 | 49-55 | GKNRRPS |
| HCDR3 | 99-106 | DTDYMFDY | LCDR3 | 88-97 | SSRDNSKHVV |

TABLE 2-continued

Kabat CDR sequences of TEM8 specific antibodies m822

| | SEQ ID NO: 3 | A.A. Sequence | | SEQ ID NO: 4 | A.A. Sequence |
|---|---|---|---|---|---|
| HCDR1 | 26-32 | GYTFSSY | LCDR1 | 23-33 | QGDNLRDFYAS |
| HCDR2 | 52-57 | IPIFGT | LCDR2 | 49-55 | GKNRRPS |
| HCDR3 | 99-106 | DTDYMFDY | LCDR3 | 88-97 | SSRDNSKHVV | m830

| | SEQ ID NO: 5 | A.A. Sequence | | SEQ ID NO: 6 | A.A. Sequence |
|---|---|---|---|---|---|
| HCDR1 | 26-32 | GFTFSTY | LCDR1 | 24-34 | RASQTISRYLN |
| HCDR2 | 52-57 | SNDGSN | LCDR2 | 50-56 | AASSLQS |
| HCDR3 | 99-110 | GSSWYRGNWFDP | LCDR3 | 89-97 | QQTYSPPIT | m863

| | SEQ ID NO: 7 | A.A. Sequence | | SEQ ID NO: 8 | A.A. Sequence |
|---|---|---|---|---|---|
| HCDR1 | 26-32 | GYTFTGY | LCDR1 | 24-34 | RASRAISRYLN |
| HCDR2 | 52-57 | NPTSGS | LCDR2 | 50-56 | AASSLQS |
| HCDR3 | 99-110 | DPGSPKWLAFDP | LCDR3 | 89-97 | QQTYSPPIT |

In some embodiments, the antibody includes Kabat CDRs, such as those listed in Table 2. In some embodiments, the antibody includes a heavy chain variable region including a HCDR1, HCDR2, and/or HCDR3 including amino acids 26-32, 52-57, and 99-106 of SEQ ID NO: 1, respectively. In further embodiments, the antibody includes a heavy chain variable region including a HCDR1, HCDR2, and/or HCDR3 including amino acids 26-32, 52-57, and 99-106 of SEQ ID NO: 3, respectively. In additional embodiments, the antibody includes a heavy chain variable region including a HCDR1, HCDR2, and/or HCDR3 including amino acids 26-32, 52-57, and 99-110 of SEQ ID NO: 5, respectively. In more embodiments, the antibody includes a heavy chain variable region including a HCDR1, HCDR2, and/or HCDR3 including amino acids 26-32, 52-57, and 99-110 of SEQ ID NO: 7, respectively.

In some embodiments, the antibody includes a light chain variable region including a LCDR1, LCDR2, and/or LCDR3 including amino acids 23-33, 49-55, and 88-97 of SEQ ID NO: 2, respectively. In further embodiments, the antibody includes a light chain variable region including a LCDR1, LCDR2, and/or LCDR3 including amino acids 23-33, 49-55, and 88-97 of SEQ ID NO: 4, respectively. In additional embodiments, the antibody includes a light chain variable region including a LCDR1, LCDR2, and/or LCDR3 including amino acids 24-34, 50-56, and 89-97 of SEQ ID NO: 6, respectively. In more embodiments, the antibody includes a light chain variable region including a LCDR1, LCDR2, and/or LCDR3 including amino acids 24-34, 50-56, and 89-97 of SEQ ID NO: 8, respectively.

In some embodiments, the antibody includes a heavy chain variable region including a HCDR1, HCDR2, and HCDR3 including amino acids 26-32, 52-57, and 99-106 of SEQ ID NO: 1, respectively, and a light chain variable region including a LCDR1, LCDR2, and LCDR3 including amino acids 23-33, 49-55, and 88-97 of SEQ ID NO: 2, respectively. In further embodiments, the antibody includes a heavy chain variable region including a HCDR1, HCDR2, and HCDR3 including amino acids 26-32, 52-57, and 99-106 of SEQ ID NO: 3, respectively, and a light chain variable region including a LCDR1, LCDR2, and LCDR3 including amino acids 23-33, 49-55, and 88-97 of SEQ ID NO: 4, respectively. In additional embodiments, the antibody includes a heavy chain variable region including a HCDR1, HCDR2, and HCDR3 including amino acids 26-32, 52-57, and 99-110 of SEQ ID NO: 5, respectively, and a light chain variable region including a LCDR1, LCDR2, and LCDR3 including amino acids 24-34, 50-56, and 89-97 of SEQ ID NO: 6, respectively. In more embodiments, the antibody includes a heavy chain variable region including a HCDR1, HCDR2, and HCDR3 including amino acids 26-32, 52-57, and 99-110 of SEQ ID NO: 7, respectively, and a light chain variable region including a LCDR1, LCDR2, and LCDR3 including amino acids 24-34, 50-56, and 89-97 of SEQ ID NO: 8, respectively.

In some embodiments, the antibody includes a heavy chain variable region including an amino acid sequence at least 95%, 96%, 97%, 98%, or 99% identical to the amino acid sequence set forth as one of SEQ ID NO: 1 (m825 VH), SEQ ID NO: 3 (m822 VH), SEQ ID NO: 5 (m830 VH), or SEQ ID NO: 7 (m863 VH). In more embodiments, the antibody includes a light chain variable region including an amino acid sequence at least 95%, 96%, 97%, 98%, or 99% identical to the amino acid sequence set forth as one of SEQ ID NO: 2 (m825 VL), SEQ ID NO: 4 (m822 VL), SEQ ID NO: 6 (m830 VL), or SEQ ID NO: 8 (m863 VL).

In additional embodiments, the antibody includes a heavy chain variable region including an amino acid sequence at least 95%, 96%, 97%, 98%, or 99% identical to the amino acid sequence set forth as SEQ ID NO: 1 (m825 VH), and a light chain variable region including an amino acid sequence at least 95%, 96%, 97%, 98%, or 99% identical to the amino acid sequence set forth as SEQ ID NO: 2 (m825 VL). In further embodiments, the antibody includes a heavy chain variable region including an amino acid sequence at least 95%, 96%, 97%, 98%, or 99% identical to the amino acid sequence set forth as SEQ ID NO: 3 (m822 VH), and a light chain variable region including an amino acid sequence at least 95%, 96%, 97%, 98%, or 99% identical to the amino acid sequence set forth as SEQ ID NO: 4 (m822 VL). In additional embodiments, the antibody includes a heavy chain variable region including an amino acid sequence at least 95%, 96%, 97%, 98%, or 99% identical to the amino acid sequence set forth as SEQ ID NO: 5 (m830

VH), and a light chain variable region including an amino acid sequence at least 95%, 96%, 97%, 98%, or 99% identical to the amino acid sequence set forth as SEQ ID NO: 6 (m830 VL). In more embodiments, the antibody includes a heavy chain variable region including an amino acid sequence at least 95%, 96%, 97%, 98%, or 99% identical to the amino acid sequence set forth as SEQ ID NO: 7 (m863 VH), and a light chain variable region including an amino acid sequence at least 95%, 96%, 97%, 98%, or 99% identical to the amino acid sequence set forth as SEQ ID NO: 8 (m863 VL).

In additional embodiments, the antibody includes a heavy chain variable region including the amino acid sequence set forth as one of SEQ ID NO: 1 (m825 VH), SEQ ID NO: 3 (m822 VH), SEQ ID NO: 5 (m830 VH), or SEQ ID NO: 7 (m863 VH). In more embodiments, the antibody includes a light chain variable region including the amino acid sequence set forth as one of SEQ ID NO: 2 (m825 VL), SEQ ID NO: 4 (m822 VL), SEQ ID NO: 6 (m830 VL), or SEQ ID NO: 8 (m863 VL).

In some embodiments, the antibody includes a heavy chain variable region including the amino acid sequence set forth as SEQ ID NO: 1 (m825 VH), and a light chain variable region including the amino acid sequence set forth as SEQ ID NO: 2 (m825 VL). In further embodiments, the antibody includes a heavy chain variable region including the amino acid sequence set forth as SEQ ID NO: 3 (m822 VH), and a light chain variable region including the amino acid sequence set forth as SEQ ID NO: 4 (m822 VL). In additional embodiments, the antibody includes a heavy chain variable region including the amino acid sequence set forth as SEQ ID NO: 5 (m830 VH), and a light chain variable region including the amino acid sequence set forth as SEQ ID NO: 6 (m830 VL). In more embodiments, the antibody includes a heavy chain variable region including the amino acid sequence set forth as SEQ ID NO: 7 (m863 VH), and a light chain variable region including the amino acid sequence set forth as SEQ ID NO: 8 (m863 VL).

1. Additional Description of Antibodies and Antigen Binding Fragments

The antibody or antigen binding fragment can be a human antibody or fragment thereof. Chimeric antibodies are also provided. The antibody or antigen binding fragment can include any suitable framework region, such as (but not limited to) a human framework region. Human framework regions, and mutations that can be made in a human antibody framework regions, are known in the art (see, for example, in U.S. Pat. No. 5,585,089, which is incorporated herein by reference). Alternatively, a heterologous framework region, such as, but not limited to a mouse framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

The antibody can be of any isotype. The antibody can be, for example, an IgM or an IgG antibody, such as $IgG_1$, $IgG_2$, $IgG_3$, or $IgG_4$. The class of an antibody that specifically binds TEM8 can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. In particular examples, the $V_H$ amino acid sequence is set forth as one of SEQ ID NOs: 1, 3, 5, 7. In other examples, the $V_L$ amino acid sequence is set forth as one of SEQ ID NOs: 2, 4, 6, 8. In a non-limiting example, the $V_H$ amino acid sequence is set forth as SEQ ID NO: 1, and the $V_L$ amino acid sequence is set forth as SEQ ID NO: 2. A nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds TEM8, that was originally IgM may be class switched to an IgG. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on.

(a) Binding Affinity

In several embodiments, the antibody or antigen binding fragment can specifically bind TEM8 protein with an affinity (e.g., measured by $K_d$) of no more than $1.0\times10^{-8}$ M, no more than $5.0\times10^{-8}$ M, no more than $1.0\times10^{-9}$ M, no more than $5.0\times10^{-9}$ M, no more than $1.0\times10^{-10}$ M, no more than $5.0\times10^{-10}$ M, or no more than $1.0\times10^{-11}$ M. $K_d$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620). 100 µM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

In another assay, $K_d$ can be measured using surface plasmon resonance assays using a BIACORE®-2000 or a BIACORE®-3000 (BIAcore. Inc., Piscataway. N.J.) at 25° C. with immobilized antigen CM5 chips at ~10 response units (RU). Briefly, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

(b) Multispecific Antibodies

In some embodiments, the antibody or antigen binding fragment is included on a multispecific antibody, such as a bi-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

In some embodiments, the antibody or antigen binding fragment is included on a bispecific antibody that that specifically binds to TEM8 protein and further specifically binds to CD3. Examples of CD3 binding domains that can be included on the bispecific antibody or antigen binding fragment are known and include those disclosed in PCT Pub. No. WO2013/163427, which is incorporated by reference herein in its entirety.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack, *J. Immunol.*, 158:3965-3970, 1997; Mack, *PNAS*, 92:7021-7025, 1995; Kufer, *Cancer Immunol. Immunother.*, 45:193-197, 1997; Loffler, *Blood*, 95:2098-2103, 2000; and Bruhl, *J. Immunol.*, 166:2420-2426, 2001. Production of bispecific Fab-scFv ("bibody") molecules are described, for example, in Schoonjans et al. (J. Immunol. 165:7050-57, 2000) and Willems et al. (J Chromatogr B Analyt Technol Biomed Life Sci. 786:161-76, 2003). For bibodies, a scFv molecule can be fused to one of the VL-CL (L) or VH-CH1 chains, e.g., to produce a bibody one scFv is fused to the C-term of a Fab chain.

(c) Fragments

Antigen binding fragments are encompassed by the present disclosure, such as Fab, F(ab')$_2$, and Fv which include a heavy chain and light chain variable region and specifically bind TEM8 protein.

These antibody fragments retain the ability to selectively bind with the antigen and are "antigen-binding" fragments. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule. A scFv is a fusion protein in which a light chain variable region of an immunoglobulin and a heavy chain variable region of an immunoglobulin are bound by a linker (see, e.g., Ahmad et al., Clin. Dev. Immunol., 2012, doi:10.1155/2012/980250; Marbry, IDrugs, 13:543-549, 2010). The intramolecular orientation of the $V_H$-domain and the $V_L$-domain in a scFv, is not decisive for the provided antibodies (e.g., for the provided multispecific antibodies). Thus, scFvs with both possible arrangements ($V_H$-domain-linker domain-$V_L$-domain; $V_L$-domain-linker domain-$V_H$-domain) may be used.

(6) A dimer of a single chain antibody (scFV$_2$), defined as a dimer of a scFV. This has also been termed a "miniantibody."

Methods of making these fragments are known in the art (see for example, Harlow and Lane, *Antibodies: A Laboratory Manual*, 2$^{nd}$, Cold Spring Harbor Laboratory, New York, 2013).

In a further group of embodiments, the antibody binding fragment can be an Fv antibody, which is typically about 25 kDa and contain a complete antigen-binding site with three CDRs per each heavy chain and each light chain. To produce Fv antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a nucleic acid molecule encoding the $V_H$ and $V_L$ domains connected by an oligonucleotide. The nucleic acid molecule is inserted into an expression vector, which is subsequently introduced into a host cell such as a mammalian cell. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; Ahmad et al., *Clin. Dev. Immunol.*, 2012, doi: 10.1155/2012/980250; Marbry, *IDrugs*, 13:543-549, 2010). Dimers of a single chain antibody (scFV$_2$), are also contemplated.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Antigen binding single V$_H$ domains, called domain antibodies (dAb), have also been identified from a library of murine V$_H$ genes amplified from genomic DNA of immunized mice (Ward et al. *Nature* 341:544-546, 1989). Human single immunoglobulin variable domain polypeptides capable of binding antigen with high affinity have also been described (see, for example, PCT Publication Nos. WO 2005/035572 and WO 2003/002609). The CDRs disclosed herein can also be included in a dAb.

In some embodiments, one or more of the heavy and/or light chain complementarity determining regions (CDRs) from a disclosed antibody is expressed on the surface of another protein, such as a scaffold protein. The expression of domains of antibodies on the surface of a scaffolding protein are known in the art (see e.g. Liu et al., *J. Virology* 85(17): 8467-8476, 2011). Such expression creates a chimeric protein that retains the binding for TEM8. In some specific embodiments, one or more of the heavy chain CDRs is grafted onto a scaffold protein, such as one or more of heavy chain CDR1, CDR2, and/or CDR3. One or more CDRs can also be included in a diabody or another type of single chain antibody molecule.

(d) Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, decreased immunogenicity, or improved ADCC or CDC.

The variants typically retain amino acid residues necessary for correct folding and stabilizing between the V$_H$ and the V$_L$ regions, and will retain the charge characteristics of the residues in order to preserve the low pI and low toxicity of the molecules. Amino acid substitutions can be made in the V$_H$ and the V$_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some embodiments, the heavy chain of the antibody includes up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NOs: 1, 3, 5, or 7. In some embodiments, the light chain of the antibody includes up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NOs: 2, 4, 6, or 8.

In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework regions of the heavy chain of the antibody, or the light chain of the antibody, or the heavy and light chains of the antibody, compared to a known framework region, or compared to the framework regions of the m825, m822, m830, or m863 antibodies as disclosed herein, and maintain the specific binding activity for TEM8 protein.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In certain embodiments of the variant VH and VL sequences provided above, each CDR either is unaltered, or contains no more than one, two or three amino acid substitutions.

To increase binding affinity of the antibody, the V$_L$ and V$_H$ segments can be randomly mutated, such as within H-CDR3 region or the L-CDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the H-CDR3 or L-CDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for TEM8 protein. In particular examples, the $V_H$ amino acid sequence is one of SEQ ID NOs: 1, 3, 5, or 7. In other examples, the $V_L$ amino acid sequence is SEQ ID NOs: 2, 4, 6, or 8. Methods of in vitro affinity maturation are known (see, e.g., Chowdhury, *Methods Mol. Biol.* 207:179-196 (2008)), and Hoogenboom et al. in *Methods in Molecular Biology* 178:1-37 (O'Brien et al., ed., Human Press, Totowa, N.J., (2001).)

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

In certain embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta. L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140: US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec 13 CHO cells deficient in protein fucosylation (Ripka et al. *Arch. Biochem. Biophys.* 249:533-545 (1986); US Pat Appl No US 2003/0157108 A1, Presta. L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda. Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.): and WO 1999/22764 (Raju. S.).

In several embodiments, the constant region of the antibody includes one or more amino acid substitutions to optimize in vivo half-life of the antibody. The serum half-life of IgG Abs is regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al., *J Immunol.,* 176:346-356, 2006); M428L and N434S (the "LS" mutation, see, e.g., Zalevsky, et al., *Nature Biotechnology,* 28:157-159, 2010); N434A (see, e.g., Petkova et al., *Int. Immunol.,* 18:1759-1769, 2006); T307A, E380A, and N434A (see, e.g., Petkova et al., *Int. Immunol.,* 18:1759-1769, 2006); and M252Y, S254T, and T256E (see, e.g., Dall'Acqua et al., *J. Biol. Chem.,* 281:23514-23524, 2006).

In some embodiments, the constant region of the antibody includes one of more amino acid substitutions to optimize Antibody-dependent cell-mediated cytotoxicity (ADCC). ADCC is mediated primarily through a set of closely related Fcγ receptors. In some embodiments, the antibody includes one or more amino acid substitutions that increase binding to FcγRIIIa. Several such substitutions are known to the person of ordinary skill in the art, such as substitutions at IgG constant regions S239D and 1332E (see, e.g., Lazar et al., *Proc. Natl., Acad. Sci. U.S.A.,* 103:4005-4010, 2006); and S239D, A330L, and 1332E (see, e.g., Lazar et al., *Proc. Natl., Acad. Sci. U.S.A.,* 103:4005-4010, 2006).

Combinations of the above substitutions are also included, to generate an IgG constant region with increased binding to FcRn and FcγRIIIa. The combinations increase antibody half-life and ADCC. For example, such combination include antibodies with the following amino acid substitution in the Fc region:

(1) S239D/I332E and T250Q/M428L;
(2) S239D/I332E and M4281L/N434S;
(3) S239D/I332E and N434A;
(4) S239D/I332E and T307A/E380A/N434A;
(5) S239D/I332E and M252Y/S254T/T256E;
(6) S239D/A330L/332E and T250Q/M428L;
(7) S239D/A330L/332E and M428L/N434S;
(8) S239D/A330L/332E and N434A;
(9) S239D/A330L/332E and T307A/E380A/N434A; or
(10) S239D/A330L/332E and M252Y/S254T/T256E.

In some examples, the antibodies, or an antigen binding fragment thereof is modified such that it is directly cytotoxic to infected cells, or uses natural defenses such as complement, antibody dependent cellular cytotoxicity (ADCC), or phagocytosis by macrophages.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The antibody or antigen binding fragment can be derivatized or linked to another molecule (such as another peptide or protein). In general, the antibody or antigen binding fragment is derivatized such that the binding to TEM8 is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

Also included are antibodies that bind to the same epitope on TEM8 to which the TEM8 specific antibodies provided herein bind. Antibodies that bind to such an epitope can be identified based on their ability to cross-compete (for example, to competitively inhibit the binding of, in a statistically significant manner) with the TEM8 specific antibodies provided herein in TEM8 binding assays (such as those described in the Examples). An antibody "competes" for binding when the competing antibody inhibits TEM8 binding of an antibody of the invention by more than 50%, in the presence of competing antibody concentrations higher than $10^6 \times K_D$ of the competing antibody. In a certain embodiment, the antibody that binds to the same epitope on TEM8 as the antibodies of the present invention is a human monoclonal antibody. Such human monoclonal antibodies can be prepared and isolated as described herein.

B. Conjugates

Human monoclonal antibodies specific for TEM8, or antigen binding fragments thereof, can be conjugated to an agent, such as an effector molecule or detectable marker, using any number of means known to those of skill in the art. Both covalent and non-covalent attachment means may be used. Conjugates include, but are not limited to, molecules in which there is a covalent linkage of an effector molecule or a detectable marker to an antibody or antigen binding fragment that specifically binds TEM8. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^3H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

Effector molecules and detectable markers can be linked to an antibody or antigen binding fragment of interest using any number of means known to those of skill in the art. Both covalent and non-covalent attachment means may be used. The procedure for attaching an effector molecule or detectable marker to an antibody or antigen binding fragment varies according to the chemical structure of the effector. Polypeptides typically contain a variety of functional groups; such as carboxylic acid (COOH), free amine (—$NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

Additionally, in several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

Thus, in several embodiments, the conjugate includes a linker that connects the effector molecule or detectable marker to the TEM8-specific antibody or antigen binding fragment thereof. In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15, amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

The antibodies or antigen binding fragments disclosed herein can be derivatized, for example, by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

In view of the large number of methods that have been reported for attaching a variety of radiodiagnostic compounds, radiotherapeutic compounds, labels (such as enzymes or fluorescent molecules), toxins, and other agents to antibodies one skilled in the art will be able to determine a suitable method for attaching a given agent to an antibody or antigen binding fragment or other polypeptide. For example, the antibody or antigen binding fragment can be conjugated with small molecular weight drugs such as Monomethyl Auristatin E (MMAE), Monomethyl Auristatin F (MMAF), maytansine, maytansine derivatives, including the derivative of maytansine known as DM1 (also known as mertansine), or other chemotherapeutic agents to make an antibody drug conjugate (ADC). In several embodiments, various chemotherapeutic agents described herein can be conjugated to the provided antibodies to generate a conjugate.

In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

In one example, the conjugate includes a monoclonal antibody that specifically binds TEM8 (or antigen binding fragment thereof), a non-reducible thioester linker and the maytansinoid toxin DM1; for example the conjugate can include the structure set forth as (wherein "mAb" refers to the monoclonal antibody or antigen binding fragment thereof):

keto acid. For example, auristatin E can be reacted with paraacetyl benzoic acid or benzoylvaleric acid to produce AEB and AEVB, respectively. Other exemplary auristatins include AFP, MMAF, and MMAE. The synthesis and structure of exemplary auristatins are described in U.S. Patent Application Publication No. 2003/0083263; International Patent Publication No. WO 04/010957, International Patent Publication No. WO 02/088172, and U.S. Pat. Nos. 7,498,298, 6,884,869, 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety. Additional description of antibody drug conjugates including the auristatin MMAE, and methods of making such conjugates, is provided in, e.g., U.S. Pub. Nos. 2011/0268751, 2008/0305044, 2007/0258987, each of which is incorporated by reference herein in its entirety). Auristatins have been shown to interfere with microtubule dynamics and nuclear and cellular division and have anticancer activity. Auristatins bind tubulin and can exert a cytotoxic or cytostatic effect on cells. There are a number of different assays, known in the art, which can be used for determining whether an auristatin or resultant conjugate exerts a cytostatic or cytotoxic effect on a desired cell line.

In one example, the conjugate includes a monoclonal antibody that specifically binds TEM8 (or antigen binding fragment thereof), a cleavable linker including a Valine-

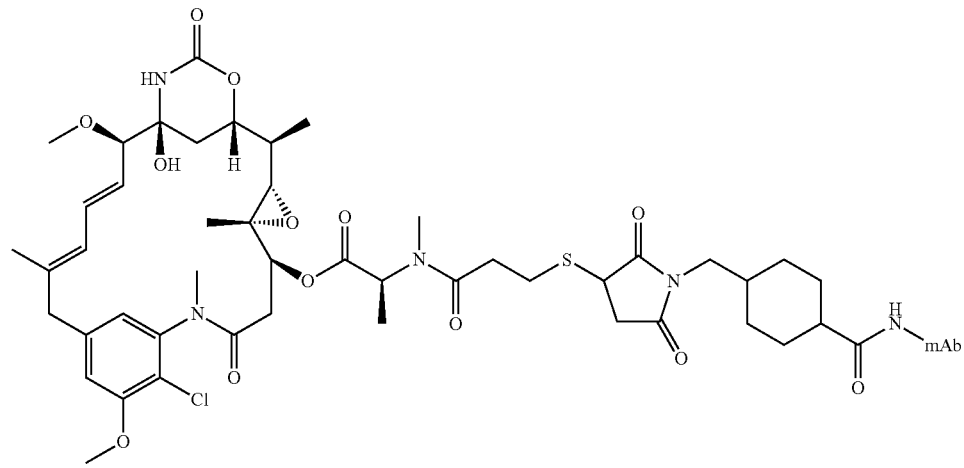

In some embodiments, the effector molecule is an auristatin, such as auristatin E (also known in the art as a derivative of dolastatin-10) or a derivative thereof. The auristatin can be, for example, an ester formed between auristatin E and a Citruline (Val-Cit) peptide cleavage site, a spacer, and the toxin MMAE; for example the conjugate can include the structure set forth as (wherein "mAb" refers to the monoclonal antibody or antigen binding fragment thereof):

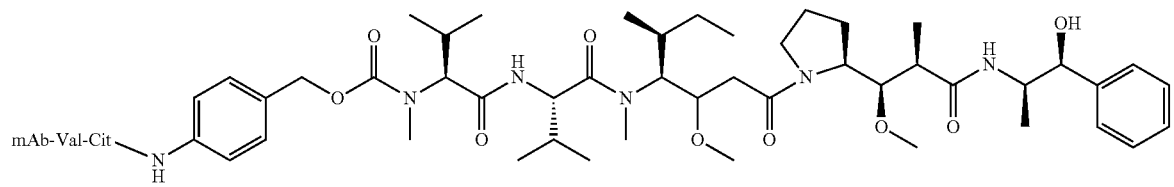

In one preferred embodiment, the conjugate may be

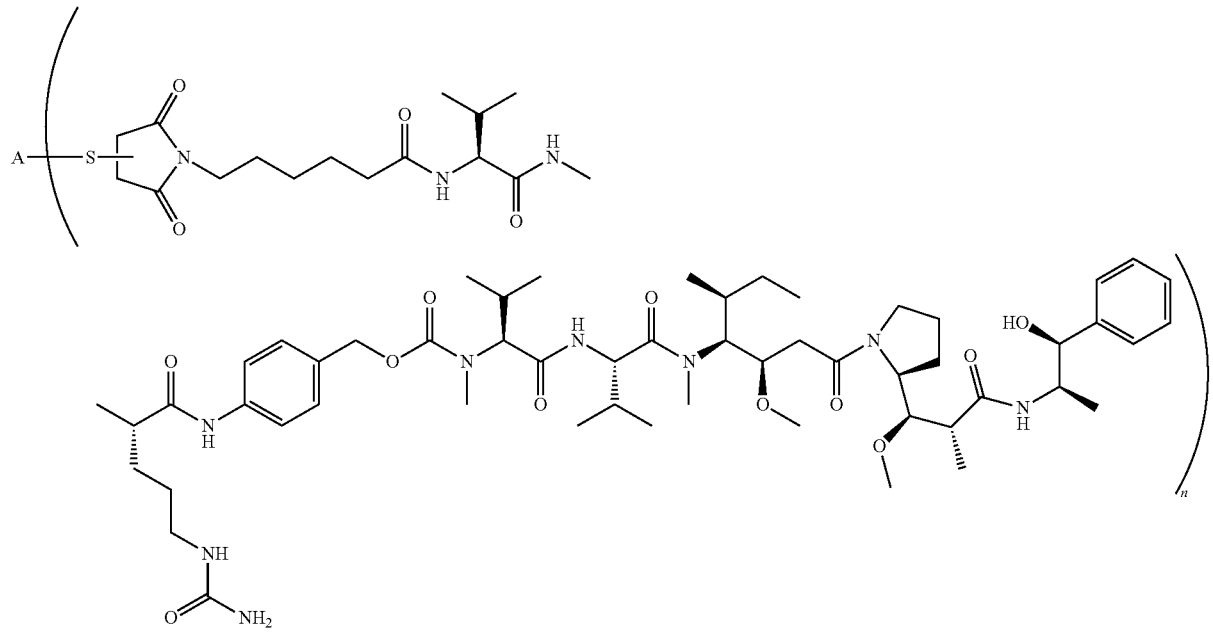

where n is an integer (such as an even integer) from 0 to 10 (such as 0 to 8, 0 to 4, 2 to 4, 2 to 8, 1 to 10, 1 to 8, or 1 to 4, or 2, 4, 6, or 8), A is a monoclonal antibody or antigen binding fragment thereof comprising a heavy chain variable region comprising a heavy chain complementarity determining region (H-CDR)1, a H-CDR2, and a H-CDR3 comprising amino acids 26-33, 51-58, and 97-106 of SEQ ID NO: 1, respectively, and a light chain variable region comprising a light chain complementarity determining region (L-CDR) 1, a L-CDR2, and a L-CDR3 comprising amino acids 26-31, 49-51, and 88-97 of SEQ ID NO: 2, respectively, wherein the antibody or antigen binding fragment specifically binds to TEM8, and S is a sulfur atom from the antibody. In one embodiment, preferably n is an even integer from 0 to 8, preferably from 0 to 4. The S moiety can be exposed by reduction or partial reduction of the inter-chain disulfides of the antibody (e.g., by treatment with a reducing agent such as DTT or TCEP).

In one non-limiting embodiment, the conjugate may be

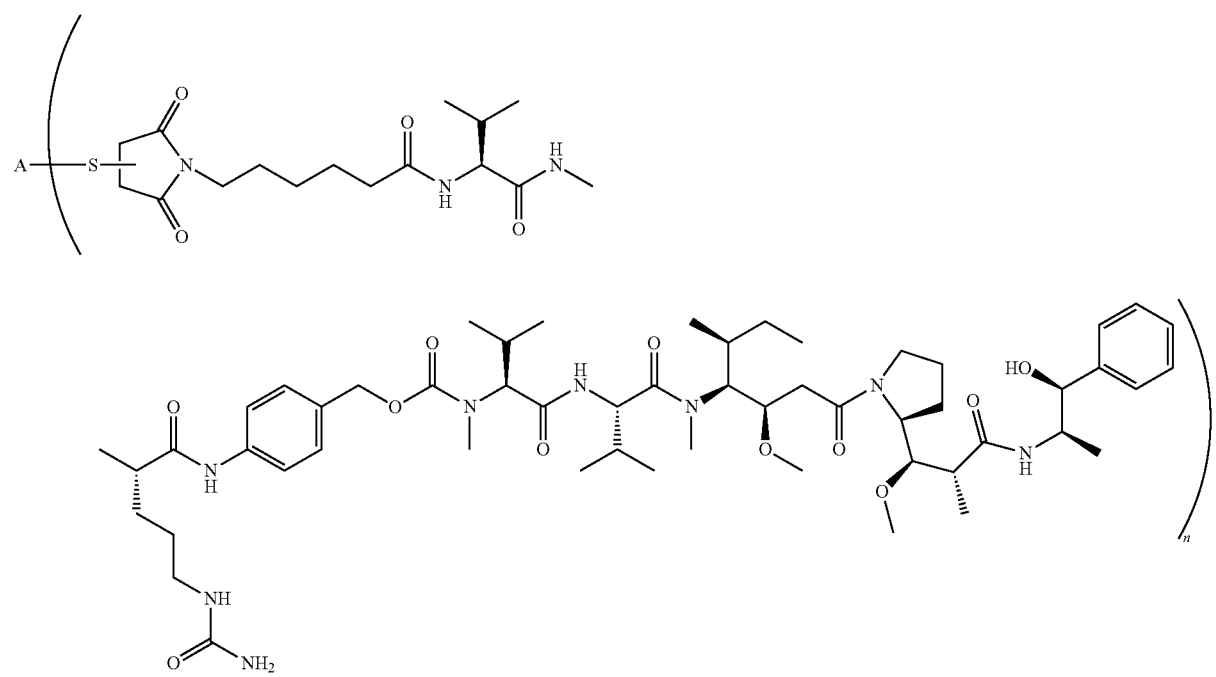

where n is 4, and A is a monoclonal antibody or antigen binding fragment thereof comprising a heavy chain variable region comprising a heavy chain complementarity determining region (H-CDR)1, a H-CDR2, and a H-CDR3 comprising amino acids 26-33, 51-58, and 97-106 of SEQ ID NO: 1, respectively, and a light chain variable region comprising a light chain complementarity determining region (L-CDR) 1, a L-CDR2, and a L-CDR3 comprising amino acids 26-31, 49-51, and 88-97 of SEQ ID NO: 2, respectively, wherein the antibody or antigen binding fragment specifically binds to TEM8. In some such embodiments, the heavy chain variable region comprises the amino acid sequence set forth as SEQ ID NO: 1 and the light chain variable region comprises the amino acid sequence set forth as SEQ ID NO: 2, and S is a sulfur atom from the antibody or antigen binding fragment thereof.

Additional toxins can be employed with antibodies that specifically bind TEM8, and antigen binding fragment of these antibodies. Exemplary toxins include Pseudomonas exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401). In some embodiments, these conjugates are of use for the treatment of a carcinoma, for example a breast carcinoma, colorectal carcinoma, lung carcinoma and melanoma.

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. No. 5,792,458 and U.S. Pat. No. 5,208,021.

Ricin is the lectin RCA60 from *Ricinus communis* (Castor bean). For examples of ricin, see, U.S. Pat. No. 5,079,163 and U.S. Pat. No. 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

In one embodiment, the toxin is *Pseudomonas* exotoxin (PE) (U.S. Pat. No. 5,602,095). As used herein, PE includes full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., J. Biol. Chem. 264:14256-14261, 1989). PE employed with the provided antibodies can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., Proc. Natl. Acad. Sci. USA, 88:3358-3362, 1991; Kondo et al., J. Biol. Chem., 263:9470-9475, 1988; Pastan et al., Biochim. Biophys. Acta, 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., Blood 113(16): 3792-3800, 2009; Onda et al., Proc. Natl. Acad. Sci. USA, 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., Blood 113(16):3792-3800, 2009; PCT Publication No. WO 2009/032954). In other examples, the PE is a variant designated PE-LR/6X (PCT Publication No. WO 2011/032022). In other examples, the PE is a variant designated PE-LR/8M (PCT Publication No. WO 2011/032022).

A monoclonal antibody that specifically binds TEM8 (or antigen binding fragment thereof) can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody or antigen binding fragment may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

An antibody or antigen binding fragment can also be conjugated with a radiolabeled amino acid. The radiolabel may be used for both diagnostic and therapeutic purposes. For instance, the radiolabel may be used to detect TEM8 and TEM8 expressing cells by x-ray, emission spectra, or other diagnostic techniques. Further, the radiolabel may be used therapeutically as a toxin for treatment of tumors in a subject, for example for treatment of breast carcinoma, lung carcinoma, colorectal carcinoma or melanoma. Examples of labels for polypeptides include, but are not limited to, the following radioisotopes or radionuclides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

An antibody or antigen binding fragment can also be derivatized with a chemical group such as polyethylene glycol (PEG), a methyl or ethyl group, or a carbohydrate group. These groups may be useful to improve the biological characteristics of the antibody or antigen binding fragment, such as to increase serum half-life or to increase tissue binding.

The average number of effector molecule or detectable marker moieties per antibody or antigen binding fragment in a conjugate can range, for example, from 1 to 20 moieties per antibody or antigen binding fragment. For some conjugates, the average number of effector molecule or detectable marker moieties per antibody or antigen binding fragment may be limited by the number of attachment sites on the antibody or antigen binding fragment. For example, where the attachment is a cysteine thiol, an antibody or antigen binding fragment may have only one or several cysteine thiol groups, or may have only one or several sufficiently reactive thiol groups through which a linker may be attached. In certain embodiments, the average number of effector molecule or detectable marker moieties per antibody or antigen binding fragment in a conjugate range from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. See, for example, U.S. Pat. No. 7,498,298, incorporated by reference herein in its entirety. The average number of effector molecule or detectable marker moieties per antibody or antigen binding fragment in preparations of conjugates may be characterized by conventional means such as mass spectroscopy and, ELISA assay. The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments (such as thioMab or thioFab prepared as disclosed in WO2006/03448, incorporated by reference herein in its entirety.

C. Chimeric Antigen Receptors (CARs)

Also disclosed herein are chimeric antigen receptor (CARs) that are artificially constructed chimeric proteins including an extracellular antigen binding domain (e.g., single chain variable fragment (scFv)) that specifically binds to TEM8, linked to a transmembrane domain, linked to one or more intracellular T-cell signaling domains. Characteristics of the disclosed CARs include their ability to redirect T-cell specificity and reactivity towards TEM8 expressing cells in a non-MHC-restricted manner. The non-MHC-restricted TEM8 recognition gives T cells expressing a disclosed CAR the ability to recognize antigen independent of antigen processing.

The intracellular T cell signaling domains can include, for example, a T cell receptor signaling domain, a T cell costimulatory signaling domain, or both. The T cell receptor signaling domain refers to a portion of the CAR comprising the intracellular domain of a T cell receptor, such as the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Region

Several embodiments provide a CAR including an antigen binding domain that specifically binds to TEM8 as disclosed herein. For example, the antigen binding domain can be a scFv including the heavy chain variable region and the light chain variable region of any of the antibodies or antigen binding fragments thereof disclosed above.

In some embodiment, the antigen binding domain can include a heavy chain variable region and a light chain variable region including the HCDR1, HCDR2, and HCDR3, and LCDR1, LCDR2, and LCDR3 of the of the heavy and light chain variable regions, respectively, of one of the m825, m822. M830, or m863 antibodies (e.g., as set forth in Table 1 or Table 2).

In some embodiments, the antigen binding domain includes a heavy chain variable region and a light chain variable region including the amino acid sequences set forth as SEQ ID NOs: 1 and 2, respectively; SEQ ID NOs: 3 and 4, respectively; SEQ ID NOs: 5 and 6, respectively; or SEQ ID NOs: 7 and 8, respectively.

In several embodiments, the antigen binding domain can be a scFv. In some embodiments, the scFv includes a heavy chain variable region and a light chain variable region joined by a peptide linker, such as a linker including the amino acid sequence set forth as GGGGSGGGGSGGGGS (SEQ ID NO: 19).

The CAR can include a signal peptide sequence, e.g., N-terminal to the antigen binding domain. The signal peptide sequence may comprise any suitable signal peptide sequence. In an embodiment, the signal peptide sequence is a human granulocyte-macrophage colony-stimulating factor (GM-CSF) receptor sequence, such as an amino acid sequence including or consisting of LLVTSLLLCELPHPA-FLLIPDT SEQ ID NO: 20. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

Between the antigen binding domain and the transmembrane domain of the CAR, there may be a spacer domain, which includes a polypeptide sequence. The spacer domain may comprise up to 300 amino acids, preferably 10 to 100 amino acids and most preferably 25 to 50 amino acids. In some embodiments, the spacer domain can include an immunoglobulin domain, such as a human immunoglobulin sequence. In an embodiment, the immunoglobulin domain comprises an immunoglobulin CH2 and CH3 immunoglobulin G (IgG1) domain sequence (CH2CH3). In this regard, the spacer domain can include an immunoglobulin domain comprising or consisting of the amino acid sequence set forth as SEQ ID NO: 21:

EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGKKDPK

Without being bound to a particular theory, it is believed that the CH2CH3 domain extends the antigen binding domain of the CAR away from the membrane of CAR-expressing cells and may more accurately mimic the size and domain structure of a native TCR.

2. Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used.

The transmembrane domain may be derived either from a natural or from a synthetic source. Where the source is natural, the domain may be derived from any membrane-bound or transmembrane protein. Exemplary transmembrane domains for use in the disclosed CARs can include at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD154. Alternatively the transmembrane domain may be synthetic, in which case it will comprise predominantly hydrophobic residues such as leucine and valine. In several embodiments, a triplet of phenylalanine, tryptophan and valine will be found at each end of a synthetic transmembrane domain.

Optionally, a short oligo- or polypeptide linker, preferably between 2 and 10 amino acids in length may form the linkage between the transmembrane domain and the intracellular T cell signaling domain and/or T cell costimulatory domain of the CAR. A exemplary linker sequence includes one or more glycine-serine doublets.

In some embodiments, the transmembrane domain comprises the transmembrane domain of a T cell receptor, such as a CD8 transmembrane domain. Thus, the CAR can include a CD8 transmembrane domain including or consisting of SEQ ID NO: 22:

TTTPAPRPPTPAPTIASQPLSLRPEACRPAAGGAVHTRGLDFACDIYIWAP

LAGTCGVLLLSLVITLYC

In another embodiment, the transmembrane domain comprises the transmembrane domain of a T cell costimulatory molecule, such as CD137 or CD28. Thus, the CAR can include a CD28 transmembrane domain including or consisting of SEQ ID NO: 23:

IEVMYPPPYLDNEKSNGTIIHVKGKHLCPSPLFPGPSKPFWVLVVVGGVLA

CYSLLVTVAFIIFWVR

3. Intracellular Region

The intracellular region of the CAR includes one or more intracellular T cell signaling domains responsible for activation of at least one of the normal effector functions of a T cell in which the CAR is expressed or placed in. Exemplary T cell signaling domains are provided herein, and are known to the person of ordinary skill in the art.

While an entire intracellular T cell signaling domain can be employed in a CAR, in many cases it is not necessary to use the entire chain. To the extent that a truncated portion of the intracellular T cell signaling domain is used, such truncated portion may be used in place of the intact chain as long as it transduces the relevant T cell effector function signal.

Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability.

T cell receptor signaling domains regulate primary activation of the T cell receptor complex either in a stimulatory way, or in an inhibitory way. The disclosed CARs can include primary cytoplasmic signaling sequences that act in a stimulatory manner, which may contain signaling motifs that are known as immunoreceptor tyrosine-based activation motifs or ITAMs. Examples of ITAM containing primary cytoplasmic signaling sequences that can be included in a disclosed CAR include include those from CD3 zeta, FcR gamma, FcR beta, CD3 gamma, CD3 delta, CD3 epsilon, CDS, CD22, CD79a, CD79b, and CD66d proteins. In several embodiments, the cytoplasmic signaling molecule in the CAR includes an intracellular T cell signaling domain from CD3 zeta.

The intracellular region of the CAR can include the ITAM containing primary cytoplasmic signaling domain (such as CD3-zeta) by itself or combined with any other desired cytoplasmic domain(s) useful in the context of a CAR. For example, the cytoplasmic domain of the CAR can include a CD3 zeta chain portion and an intracellular costimulatory signaling domain. The costimulatory signaling domain refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40 (CD134), CD30, CD40, PD-1, ICOS, lymphocyte function-associated antigen 1 (LFA-1), CD2, CD7, LIGHT, NKG2C, and B7-H3. An additional example of a signaling domain that can be included in a disclosed CARs is a Tumor necrosis factor receptor superfamily member 18 (TNFRSF18; also known as glucocorticoid-induced TNFR-related protein, GITR) signaling domain.

In some embodiments, the CAR can include a CD3 zeta signaling domain, a CD8 signaling domain, a CD28 signaling domain, a CD137 signaling domain or a combination of two or more thereof. In one embodiment, the cytoplasmic domain includes the signaling domain of CD3-zeta and the signaling domain of CD28. In another embodiment, the cytoplasmic domain includes the signaling domain of CD3 zeta and the signaling domain of CD137. In yet another embodiment, the cytoplasmic domain includes the signaling domain of CD3-zeta and the signaling domain of CD28 and CD137. The order of the one or more T cell signaling domains on the CAR can be varied as needed by the person of ordinary skill in the art.

Exemplary amino acid sequences for such T cell signaling domains are provided. For example, the CD3 zeta signaling domain can include or consist of the amino acid sequence set forth as SEQ ID NO: 24 (RVKFSRSADAPAYQQGQNQ-LYNELNLGRREEYDVLDKRRGRDPEMGGKPRRKN-PQEGLYNEL QKDKMAEAYSEIGMKGERRRGKGH-DGLYQGLSTATKDTYDALHMQALPPR), the CD8 signaling domain can include or consist of the amino acid sequence set forth as SEQ ID NO: 25 (FVPVFLPAKPITT-PAPRPPTPAPTIASQPLSLRPEACR-PAAGGAVHTRGLDFACDIYIWAPLAGTC GVLLLSLVITLYCNHRNR), the CD28 signaling domain can include or consist of the amino acid sequence set forth as SEQ ID NO: 26 (SKRSRLLHSDYMNMTPRRPGP-TRKHYQPYAPPRDFAAYRS), the CD137 signaling domain can include or consist of the amino acid sequences set forth as SEQ ID NO: 27 (KRGRKKLLYIFKQPFMR-PVQTTQEEDGCSCRFPEEEEGGCEL) or SEQ ID NO: 28 (RFSVVKRGRKKLLYIFKQPFMRPVQTTQEEDGC-SCRFPEEEEGGCEL).

The cytoplasmic signaling sequences within the cytoplasmic signaling portion of the CAR of the invention may be linked to each other in a random or specified order. Optionally, a short polypeptide linker, preferably between 2 and 10 amino acids in length may form the linkage. A glycine-serine doublet provides a particularly suitable linker. Further, between the signaling domain and the transmembrane domain of the CAR, there may be a spacer domain, which includes a polypeptide sequence. The spacer domain may comprise up to 300 amino acids, preferably 10 to 100 amino acids and most preferably 25 to 50 amino acids.

4. Additional Description of CARs

Also provided are functional portions of the CARs described herein. The term "functional portion" when used in reference to a CAR refers to any part or fragment of the CAR, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The CAR or functional portion thereof, can include additional amino acids at the amino or carboxy terminus, or at both termini, which additional amino acids are not found in the amino acid sequence of the parent CAR. Desirably, the additional amino acids do not interfere with the biological function of the CAR or functional portion, e.g., recognize target cells, detect cancer, treat or prevent cancer, etc. More desirably, the additional amino acids enhance the biological activity, as compared to the biological activity of the parent CAR.

Also provided are functional variants of the CARs described herein, which have substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 85%, about 90%, about 91%, about 92%, about 93%, about 94%, about 95%, about 96%), about 97%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, αc-aminocycloheptane carboxylic acid, -(2-amino-2-norbornane)-carboxylic acid, γ-diaminobutyric acid, α,β-diaminopropionic acid, homophenylalanine, and α-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety.) For example, a nucleic acid molecule encoding a disclosed chimeric antigen binding receptor can be included in an expression vector (such as a lentiviral vector) for expression in a host cell, such as a T cell, to make the disclosed CAR. In some embodiments, methods of using the chimeric antigen receptor include isolating T cells from a subject, transforming the T cells with an expression vector (such as a lentiviral vector) encoding the chimeric antigen receptor, and administering the engineered T cells expressing the chimeric antigen receptor to the subject for treatment, for example for treatment of a tumor in the subject.

D. Polynucleotides and Expression

Nucleic acids encoding the amino acid sequences of antibodies, antibody binding fragments, conjugates, and CARs that specifically bind TEM8 are provided. Nucleic acids encoding these molecules can readily be produced by one of skill in the art, using the amino acid sequences provided herein (such as the CDR sequences, heavy chain and light chain sequences), sequences available in the art (such as framework sequences), and the genetic code. One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

Nucleic acid sequences encoding the of antibodies, antibody binding fragments, conjugates, and CARs that specifically bind TEM8 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In some embodiments, the nucleic acid molecule encodes a CAR as provided herein for expression in a T cell to generate a chimeric antigen receptor T cell. The nucleic acid molecule encoding the chimeric antigen binding receptor can be included in a vector (such as a lentiviral vector) for expression in a host cell, such as a T cell. Exemplary cells include a T cell, a Natural Killer (NK) cell, a cytotoxic T lymphocyte (CTL), and a regulatory T cell. Methods of generating nucleic acid molecules encoding chimeric antigen receptors and T cells including such receptors are known in the art (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety.)

The nucleic acid molecules can be expressed in a recombinantly engineered cell such as bacteria, plant, yeast, insect and mammalian cells. The antibodies, antigen binding fragments, and conjugates can be expressed as individual $V_H$ and/or $V_L$ chain (linked to an effector molecule or detectable marker as needed), or can be expressed as a fusion protein. Methods of expressing and purifying antibodies and antigen binding fragments are known and further described herein (see, e.g., Al-Rubeai (ed), *Antibody Expression and Production, Springer Press,* 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence (Gly$_4$-Ser)$_3$, such that the V$_H$ and V$_L$ sequences can be expressed as a contiguous single-chain protein, with the V$_L$ and V$_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed), Antibody Engineering, Vols. 1-2, 2$^{nd}$ Ed., Springer Press, 2010; Harlow and Lane, *Antibodies: A Laboratory Manual*, 2$^{nd}$, Cold Spring Harbor Laboratory, New York, 2013). Optionally, a cleavage site can be included in a linker, such as a furin cleavage site.

The nucleic acid encoding a V$_H$ and/or the V$_L$ optionally can encode an Fc domain (immunoadhesin). The Fc domain can be an IgA, IgM or IgG Fc domain. The Fc domain can be an optimized Fc domain, as described in U.S. Published Patent Application No. 2010/093979, incorporated herein by reference. In one example, the immunoadhesin is an IgG$_1$ Fc.

The single chain antibody may be monovalent, if only a single V$_H$ and V$_L$ are used, bivalent, if two V$_H$ and V$_L$ are used, or polyvalent, if more than two V$_H$ and V$_L$ are used. Bispecific or polyvalent antibodies may be generated that bind specifically to TEM8 and another antigen, such as, but not limited to, CD3. The encoded V$_H$ and V$_L$ optionally can include a furin cleavage site between the V$_H$ and V$_L$ domains.

Those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibodies, antibody binding fragments, conjugates, and CARs can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

Polynucleotide sequences encoding the antibody or antigen binding fragment or conjugate thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

The polynucleotide sequences encoding the antibody, or antigen binding fragment or conjugate thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or HIV-1 Env binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

For purposes of producing a recombinant CAR, the host cell may be a mammalian cell. The host cell may be a human cell. In some embodiments, the host cell may be a peripheral blood lymphocyte (PBL) or a peripheral blood mononuclear cell (PBMC), or a T cell. The T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), tumor infiltrating cells, memory T cells, naive T cells, and the like. The T cell may be a CD8$^+$ T cell or a CD4$^+$ T cell.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the antibodies, antigen binding fragments, and conjugates can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin.

Methods for expression of the antibodies, antigen binding fragments, and conjugates, and/or refolding to an appropriate active form, from mammalian cells, and bacteria such as *E. coli* have been described and are well-known and are applicable to the antibodies disclosed herein. See, e.g., Harlow and Lane, *Antibodies: A Laboratory Manual*, 2$^{nd}$, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

In addition to recombinant methods, the antibodies, antigen binding fragments, and/or conjugates can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-2156, 1963, and Stewart et al., *Solid Phase Peptide Synthesis, 2nd ed.*, Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

E. Methods of Detection

Methods are provided for detecting the presence of a cell that expresses TEM8 in a subject. In some embodiments, the methods include contacting a cell from a subject with one or more of the antibodies that specifically bind TEM8 or conjugate thereof to form an immune complex. The presence (or absence) of the immune complex is then detected. The presence of the immune complex indicates the presence of a cell that expresses TEM8 in the subject. The detection methods can involve in vivo detection or in vitro detection of the immune complex. In several embodiments, detection of a cell that expresses TEM8 includes detecting cell-surface expression of TEM8 on the endothelial cell. In several embodiments of the provided methods, detecting a cell that expresses TEM8 in a subject detects pathological angiogenesis in the subject, for example angiogenesis associated with tumor development. The cell can be an endothelial cell or a pericyte, for example.

Thus, methods are provided for detecting a cell that expresses TEM8, for example, an endothelial cell that expresses TEM8 or a pericyte that expresses TEM8. In a specific non-limiting example, the cell is an endothelial cell. In some embodiments, a subject is selected who has, is suspected of having, or is at risk of developing, a tumor, for example, a carcinoma. For example, the subject has, is suspected of having, or is at risk of developing breast carcinoma, lung carcinoma, colorectal carcinoma or melanoma. In some examples the subject has, is suspected of having, or is at risk of developing, breast, colorectal, lung or skin cancer. Thus, the presence of an endothelial cell expressing TEM8 can be detected in these subjects. In some examples, detecting an endothelial cell that expresses TEM8 detects a blood vessel comprising at least one endothelial cell that expresses TEM8. In some examples, the endothelial cell is a vascular endothelial cell, for example a vascular endothelial cell in a tumor associated blood vessel.

In one embodiment, a sample is obtained from a subject, and the presence of an endothelial cell that expresses TEM8 is assessed in vitro. For example, such methods include contacting an endothelial cell in a biological sample from the subject with one or more of the conjugates or antibodies provided herein that specifically bind TEM8 or an antigen binding fragment thereof to form an immune complex. The presence (or absence) of the immune complex is then detected. The presence of the immune complex on the endothelial cell from the subject indicates the presence of an endothelial cell that expresses TEM8 in the subject. For example, an increase in the presence of the immune complex in the sample as compared to formation of the immune complex in a control sample indicates the presence of an endothelial cell that expresses TEM8 in the subject.

A biological sample is typically obtained from a mammalian subject of interest, such as human. The sample can be any sample, including, but not limited to, tissue from biopsies, autopsies and pathology specimens. Biological samples also include sections of tissues, for example, frozen sections taken for histological purposes.

In some examples of the disclosed methods, the TEM8 specific antibody or antigen binding fragment is conjugated to a detectable marker. In some examples, the methods further include contacting a second antibody that specifically binds the TEM8 specific antibody, antigen binding fragment thereof, or a conjugate including these molecules, for a sufficient amount of time to form an immune complex and detecting this immune complex. An increase in the presence of this immune complex in a biological sample from a selected subject (as described above) compared to the presence of the immune complex in a control sample or other standard detects the presence of an endothelial cell that expresses TEM8 in the biological sample. In some examples, the second antibody is conjugated to a detectable marker.

Suitable detectable markers for the antibody or secondary antibody are described and known to the skilled artisan. For example, various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

The antibodies that specifically bind TEM8 and conjugates thereof can be used in immunohistochemical assays. These assays are well known to one of skill in the art (see Harlow & Lane, *Antibodies, A Laboratory Manual*, 2$^{nd}$ ed., Cold Spring Harbor Publications, New York (2013), for a description of immunoassay formats The antibodies disclosed herein can also be used to detect endothelial cells that express TEM8 as well as pericytes that express TEM8 in vivo. In some example, in vivo detection of an endothelial cell that expresses TEM8 detects pathological angiogenesis in the subject. Thus, methods are disclosed for detecting pathological angiogenesis in a subject, such as pathological angiogenesis associated with a tumor, such as a carcinoma; for example, a breast carcinoma, lung carcinoma, colorectal carcinoma or melanoma. In one embodiment, an effective amount of an antibody that specifically binds to TEM8 (or antigen binding fragment thereof) or a conjugate thereof is administered to the subject for a sufficient amount of time for the antibody or antigen binding fragment to form an immune complex, which can then be detected. Detection of the immune complex in the subject determines the presence of an endothelial cell that expresses TEM8, which detects pathological angiogenesis in the subject. In one specific, non-limiting example detection of an immune complex is performed by immunoscintigraphy. Other specific, non-limiting examples of immune complex detection include radiolocalization, radioimaging, magnetic resonance imaging (such as using a biotinylated antibody and avidin-iron oxide), positron emission tomography (such as using an $^{111}$indium-labeled monoclonal antibody) or fluorescence imaging (such as using luciferase or green fluorescent protein labeled antibodies). See Paty et al., *Transplantation.*, 77:1133-1137, 2004, herein incorporated by reference. In several examples, the disclosed method detects endothelial cells lining the inner wall of blood vessels in a tumor in the subject, for example, a breast carcinoma, lung carcinoma, colorectal carcinoma or melanoma.

In the setting of magnetic resonance imaging, contrast agent detection can be greatly impacted by magnetic resonance scanner field strength. Increased field strengths provide improvements by orders of magnitude in the ability to detect contrast agents (Hu et al., *Ann. Rev. Biomed. Eng.*, 6:157-184, 2004; Wedeking et al., *Magn. Reson. Imaging.*, 17:569-575, 1999). For example, the limit of detection of gadolinium at 2 tesla (T) is ~30 µM. At 4T the limit of detection is reduced to ~1 µM. With newly available 7 to 12T scanners one would expect to detect low (10-100) nM concentrations of this contrast agent. Similar sensitivity can also be identified using contrast agents such as iron oxide. Once detected the test results can be used to assist in or guide surgical or other excision of a tumor.

In one embodiment, an effective amount of an antibody or antigen binding fragment that specifically binds to TEM8 or a conjugate thereof is administered to a subject having a tumor following anti-cancer or anti-angiogenic treatment. After a sufficient amount of time has elapsed to allow for the administered antibody or antigen binding fragment or conjugate to form an immune complex with TEM8 on an endothelial cell, the immune complex is detected. For example, an antibody that specifically binds to TEM8 or conjugate thereof can be administered to a subject prior to, or following, treatment of a tumor. The tumor can be (but is not limited to) a breast, colorectal, lung or skin cancer. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Methods of Treatment

A therapeutically effective amount of an antibody or antigen binding fragment that specifically binds TEM8 or conjugate thereof or CAR T cell expressing an antigen binding fragment that specifically binds TEM8 can be administered to a subject to treat pathological angiogenesis, for example to treat a tumor, for example a carcinoma. In some embodiments, administration of a therapeutically effective amount of an antibody or antigen binding fragment that specifically binds TEM8 or conjugate thereof or CAR T cell expressing an antigen binding fragment that specifically binds TEM8 decreases pathological angiogenesis, such as pathological angiogenesis that occurs in various types of cancer, such as breast, colorectal, lung or skin cancer, or with macular degeneration. Thus, a subject can be selected for treatment that has, is suspected of having or is at risk of developing a tumor, such as a carcinoma.

In some examples, the antibodies, antigen binding fragments, CAR T cells, compositions and conjugates disclosed herein can be administered to a subject to decrease pathological angiogenesis in the subject, to slow or inhibit the growth or metastasis of a tumor, or treat corneal or retinal degeneration. In these applications, a therapeutically effective amount of an antibody or antigen binding fragment that specifically binds TEM8 or a conjugate or CAR T cells or composition is administered to a subject in an amount and under conditions sufficient to form an immune complex with TEM8, thereby slowing or inhibiting the growth or the metastasis of a tumor, or other pathological angiogenesis, or to inhibit a sign or a symptom of a cancer. Examples of suitable subjects include those diagnosed with or suspecting of having cancer (for example, a subject having a tumor), for example subjects having a carcinoma, such as a breast carcinoma, lung carcinoma, colorectal carcinoma or melanoma.

The therapeutically effective amount will depend upon the severity of the disease and the general state of the patient's health. A therapeutically effective amount is that which provides either subjective relief of a symptom(s) or an objectively identifiable improvement as noted by the clinician or other qualified observer. In one embodiment, a therapeutically effective amount is the amount necessary to inhibit tumor growth (such as growth of a breast carcinoma, lung carcinoma, colorectal carcinoma or melanoma), pathological angiogenesis, or the amount that is effective at reducing a sign or a symptom of the tumor. The therapeutically effective amount of the agents administered can vary depending upon the desired effects and the subject to be treated. In some examples, therapeutic amounts are amounts which eliminate or reduce the patient's tumor burden, or which prevent or reduce the proliferation of metastatic cells, or which prevent or reduce pathological angiogenesis.

Subjects that can benefit from the disclosed methods include human and veterinary subjects. Subjects can be screened prior to initiating the disclosed therapies, for example to determine whether the subject has a tumor or pathological angiogenesis, or both. The presence of a tumor or pathological angiogenesis, or both, indicates that the tumor or pathological angiogenesis can be treated using the methods provided herein.

Any method of administration can be used for the disclosed antibodies, antigen binding fragments, conjugates, compositions and additional agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The compositions that include an antibody or antigen binding fragment or conjugate thereof or CAR T cells can be formulated in unit dosage form suitable for individual administration of precise dosages. In addition, the compositions may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies, conjugates, compositions or additional agents can range from about 0.01 to about 30 mg/kg, such as from about 0.1 to about 10 mg/kg. In some examples, the dosage is at least about 0.1 mg/kg, at least about 0.2 mg/kg, at least about 0.3 mg/kg, at least about 0.4 mg/kg, at least about 0.5 mg/kg, at least about 1 mg/kg, at least about 4 mg/kg, at least about 3 mg/kg, at least about 5 mg/kg, at least about 6 mg/kg, at least about 7 mg/kg, at least about 8 mg/kg is at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, at least about 20 mg/kg, at least about 21 mg/kg, at least about 22 mg/kg, at least about 23 mg/kg, at least about 24 mg/kg at least about 25 mg/kg, at least about 26 mg/kg, at least about 27 mg/kg, at least about 28 mg/kg, at least about 29 mg/kg, or at least about 30 mg/kg.

In particular examples, the subject is administered a therapeutic composition that includes one or more of the conjugates, antibodies, compositions, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, a disclosed therapeutic agent is administered may be administered intravenously, subcutaneously or by another mode daily or multiple times per week for a period of time, followed by a period of no treatment, then the cycle is repeated. In some embodiments, the initial period of treatment (e.g., administration of the therapeutic agent daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the therapeutic agent is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

In additional embodiments, the antibodies, compositions and conjugates that specifically bind TEM8 can be used to decrease binding of Anthrax PA to a cell. For example, an effective amount of the provided antibodies, compositions and conjugates can be incubated with a cell under conditions sufficient to form an immune complex with TEM8, thereby decreasing binding of Anthrax PA to the cell. In some examples, an effective amount of the antibodies, compositions and conjugates that specifically bind TEM8 can be administered to a subject to decrease binding of Anthrax PA to a cell in the subject. Suitable subjects may include those diagnosed or at risk of developing with Anthrax infection or suspected of exposure to Anthrax.

Administration of the antibodies, antigen binding fragments, conjugates, CAR T cells, or compositions can be accompanied by administration of other anti-cancer or anti-angiogenesis agents or therapeutic treatments (such as surgical resection of a tumor or radiation therapy). For example, prior to, during, or following administration of a therapeutic amount of the antibodies or conjugates, the subject can receive one or more additional therapies. In one example, the subject receives one or more treatments to remove or reduce the tumor or pathological angiogenesis prior to administration of a therapeutic amount of one or more agents for treatment of the tumor or pathological angiogenesis. For example, the additional agent may include, but is not limited to, a chemotherapeutic agent, an anti-angiogenic agent, or a combination thereof. In another example, at least part of the tumor is surgically or otherwise excised or reduced in size or volume prior to administering the therapeutically effective amount of the antibody or antigen binding fragment or conjugate.

Particular examples of additional therapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the antibodies, conjugates disclosed herein. Methods and therapeutic dosages of such agents are known to those skilled in the art, and can be determined by a skilled clinician. In one example the chemotherapeutic agent includes 5-FU or IRT or both.

Microtubule binding agent refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264, can be used.

Suitable DNA and RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-FU and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

Examples of the commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, IRT (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Thus, non-limiting examples of chemotherapeutic agents for use in combination with the disclosed TEM8 specific antibodies, antigen binding fragments, or conjugates thereof, include chemotherapeutic agents such as erlotinib (TARCEVA®, Genentech/OSI Pharm.), bortezomib (VELCADE®, Millenium Pharm.), fulvestrant (FASLODEX®, AstraZeneca), sutent (SU11248, Pfizer), letrozole (FEMARA®, Novartis), imatinib mesylate (GLEEVEC®, Novartis), PTK787/ZK 222584 (Novartis), oxaliplatin (Eloxatin®, Sanofi), 5-FU (5-fluorouracil), leucovorin, Rapamycin (Sirolimus, RAPAMUNE®, Wyeth), lapatinib (TYKERB®, GSK572016, GlaxoSmithKline), lonafarnib (SCH 66336), sorafenib (BAY43-9006, Bayer Labs.), and gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; antifolate antineoplastic such as pemetrexed (ALIMTA® Eli Lilly), aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics, calicheamicin, calicheamicin gamma1I and calicheamicin omega1I; dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, for example, paclitaxel (TAXOL®, Bristol-Myers Squibb Oncology, Princeton, N.J.), ABRAXANE™ Cremophor-free, albumin, nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine (DMFO); retinoids such as retinoic acid; capecitabine; and pharmaceutically acceptable salts, acids or derivatives of any of the above.

Non-limiting examples of anti-angiogenic agents include molecules, such as proteins, enzymes, polysaccharides, oligonucleotides, DNA, RNA, and recombinant vectors, and small molecules that function to reduce or even inhibit blood vessel growth. Examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thromobospondin, endostatin, thalidomide, and derivatives and analogs thereof. For example, in some embodiments the anti-angiogenesis agent is an antibody that specifically binds to VEGF (for example, AVASTIN®, Roche) or a VEGF receptor (for example, a VEGFR2 antibody). In one example the anti-angiogenic agent includes a VEGFR2 antibody, or DMXAA (also known as Vadimezan or ASA404; available commercially, for example, from Sigma Corp., St. Louis, Mo.) or both. Exemplary kinase inhibitors include GLEEVAC®, IRESSA®, and TARCEVA® that prevent phosphorylation and activation of growth factors. Antibodies that can be used include HERCEPTIN® and AVASTIN® that block growth factors and the angiogenic pathway.

In some examples, the additional agent is a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, sorafenib, sunitinib, Tacatuzumab tetraxetan, Taplitumomab paptox, Tenatumomab, TGN1412, Ticilimumab (=tremelimumab), Tigatuzumab, TNX-650, Trastuzumab, Tremelimumab, Tucotuzumab celmoleukin, Veltuzumab, Volociximab, Votumumab, Zalutumumab.

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, and derivatives and analogs thereof.

Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

G. Compositions

Compositions are provided that include one or more of the disclosed conjugates, antibodies, or antigen binding fragments that specifically bind TEM8, or nucleic acid molecules or CARs, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenus) or local (such as intra-tumor) administration. In one example, the antibody that specifically binds TEM8 or an antigen binding fragment thereof, or conjugate including such an antibody or antigen binding fragment, is formulated for parenteral administration, such as intravenous administration. Compositions including a conjugate, antibody or antigen binding fragment as disclosed herein are of use, for example, for the treatment and detection of a tumor, for example a tumor occurring in breast, colorectal, lung or skin cancer. In some examples, the compositions are useful for the treatment or detection of a carcinoma. The compositions including a conjugate, antibody or antigen binding fragment as disclosed herein are also of use, for example, for the detection of pathological angiogenesis. The compositions including a conjugate, antibody or antigen binding fragment as disclosed herein are also of use, for example, for inhibiting the binding of Anthrax PA to TEM8.

The compositions for administration can include a solution of the conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms are known, or will be apparent, to those skilled in the art.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, Pa. (1995). In some embodiments, the composition can be a liquid formulation including one or more antibodies, antigen binding fragments (such as an antibody or antigen binding fragment that specifically binds to TEM8), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, antigen binding fragments, or conjugates may be provided in lyophilized form and rehydrated with sterile water before administration, although they are also provided in sterile solutions of known concentration. The antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. Antibodies, antigen binding fragments and conjugates can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat.

No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

In some examples, a subject is administered the DNA encoding the antibody or antigen binding fragments thereof, to provide in vivo antibody production, for example using the cellular machinery of the subject. Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression.

In another approach to using nucleic acids, a disclosed antibody, or antibody binding fragments thereof can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (*Bacillus Calmette Guerin*) provides another vector for expression of the disclosed antibodies (see Stover, *Nature* 351:456-460, 1991).

In one embodiment, a nucleic acid encoding a disclosed antibody, or antibody binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

H. Kits

Kits are also provided. For example, kits for detecting a cell (such as an endothelial cell or a pericytes) that expresses TEM8 in a subject, treating a tumor in a subject, or decreasing binding of Anthrax PA to a cell. The kits will typically include an antibody or antigen binding fragment that specifically binds TEM8 and/or a conjugate thereof.

More than one of the conjugates or antibodies or antigen binding fragments that specifically bind TEM8 can be included in the kit. Thus, the kit can include two or more antibodies that specifically bind TEM8, or an antibody or antigen binding fragment that specifically binds TEM8 and a conjugate thereof, or a combination thereof. In some embodiments, an antigen binding fragment or conjugate including an antigen binding fragment, such as an Fv fragment, is included in the kit. In one example, such as for in vivo uses, the antibody can be a scFv fragment.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed TEM8 specific antibodies, antigen binding fragments, or conjugates. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed TEM8 specific antibodies or fragments thereof, or conjugates thereof, for example, in a method of treating or preventing a tumor. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

The following examples are provided to illustrate particular features of certain embodiments, but the scope of the claims should not be limited to those features exemplified.

Example 1

TEM8 Specific Antibodies

This example illustrates the isolation of a panel of fully human anti-TEM8 antibodies from a human naïve yeast display scFv library, and characterization of those antibodies. The selection strategy involved serial panning of the libraries on both TEM8-transfected mammalian cells and purified recombinant TEM8-ED protein derived from mammalian cells, and resulted in the identification of four TEM8 antibodies, termed m825, m822, m830, and m863.

Four fully human monoclonal antibodies, m822, m825, m830 and m863 were identified from a human naïve yeast display scFv library by sorting, screening and affinity maturation against human and mouse TEM8. The TEM8 antibodies were identified from a library screen (see Puri et al., MAbs. 5:533-9, 2013 for a description of the library). The sequences of the heavy and light chain variable regions, as well as the heavy and light chain CDRs (defined by IMGT) of the identified antibodies are provided in Table 3, below.

Recombinant human and mouse TEM8 ectodomain proteins were used as the target for selection. In the first round of selection, approximately $5 \times 10^{10}$ cells from the naïve antibody library were incubated with 10 µg of biotinylated human TEM8 protein in 50 ml 0.1% bovine serum albumin (BSA)-phosphate-buffered saline (PBS), called PBSA, at room temperature for 2 hours with gentle rotation. Then, the mixture was washed three times with 0.1% PBSA to remove the unbound antibody fragments. Biotinylated TEM8 together with bound antibody fragments were subsequently incubated with 100 μl of strepatavidin-conjugated microbeads (Milenvi Biotec, Auburn, Calif.) and loaded onto the AutoMACS system for sorting. Cells which display antibody fragments with high affinity to TEM8 were collected and later amplified in SDCAA Medium (20 g Dextrose, 6.7 g Difco yeast nitrogen base without amino acids, 5 g Bacto casamino acids, 5.4 g Na$_2$HPO$_4$ and 8.56 g NaH$_2$PO$_4$. H$_2$O dissolved in 1 L of distilled water) at 250 rpm at 30° C. for 24 hours. After that, the culture was induced in SGCAA Medium (20 g Galactose, 20 g Raffinose, 1 g Dextrose, 6.7 g Difco yeast nitrogen base without amino acids, 5 g Bacto casamino acids, 5.4 g Na$_2$HPO$_4$ and 8.56 g NaH$_2$PO$_4$. H$_2$O dissolved in 1 L of distilled water) at 250 rpm at 20° C. for 18 hours. The pool obtained was subjected to another round of selection for binding to biotinylated recombinant human TEM8. To ensure sufficient diversity of antibody fragments for second and third rounds of screening, 100 folds of the pool size from the prior round of sorting was used as the input cell number.

For the third round of selection, Fc-fused recombinant human TEM8 was used. The screening was carried out in a similar way to the previous two rounds of selection toward human TEM8. Finally, antibody fragments that bound to human TEM8 were pulled down by protein G-conjugated microbeads. The yeast cells expressing antibody fragments that possess high binding affinity to human TEM8 were collected and further characterized.

TABLE 3

Protein sequence of the VH and VL domains of the m825, m822, m830, and m863 antibodies (with IMGT CDRs in bold).

| Antibody | | protein sequence (CDRs underlined) |
|---|---|---|
| m825 | VH | QVQLVQSGAEVKKPGTSVKVSCKVPGYTFSSYAISWVRQ APGQGLEWMGGIIPIFGTTNYAQKFQGRVTITGEESTST VYMELSSLRSEDTAVYYCARDTDYMFDYWGQGTLVTVSS (SEQ ID NO: 1) |
| | VL | SSELTQDPVVSVALGETVSITCQGDNLRDFYASWYQQKP GQAPLLVMYGKNRRPSGIPDRFSGSTSGNTLSLTITGAQ AEDEADYYCSSRDNSKHVVFGGGTKVTVL (SEQ ID NO: 2) |
| m822 | VH | QVQLVQSGAEVKKPGASVKVSCKVSGYTFSSYAISWVRQ APGQGLEWMGGIIPIFGTANYAQKFQGRVTITADESTST AYMELSSLRSEDTAVYYCARDTDYMFDYWGQGTLVTVSS (SEQ ID NO: 3) |
| | VL | SSELTQDPVVSVALGETVSITCQGDNLRDFYASWYQQKP GQAPLLVMYGKNRRPSGIPDRFSGSTSGNTLSLTITGAQ AEDEADYYCSSRDNSKHVVFGGGTKVTVL (SEQ ID NO: 4) |
| m830 | VH | EVQLVESGGGVVQPGRSVRLSCAASGFTFSTYTMHWVRQ APGKGLEWVAISNDGSNKYYADPVRGRFTISRDNSKNT LYLQMNSLRAEDTAVYYCVRGSSWYRGNWFDPWGQGTLV TVSS (SEQ ID NO: 5) |
| | VL | DIQMTQSPSSLSASVGDRVTIACRASQTISRYLNWYQQK PGKAPKLLIYAASSLQSGVSSRFSGSGSGTEFTLTISSL QPEDFATYFCQQTYSPPITFGQGTRLEIKR (SEQ ID NO: 6) |
| m863 | VH | EVQLVETGAEVKKPGASVKVSCKASGYTFTGYYMHWVRQ APGQGLEWMGWINPTSGSTNYAQKFQGRVTMTRDTSIST AYMELSGLRSDDTAVYYCVRDPGSPKWLAFDPWGQGTLV TVSS (SEQ ID NO: 7) |

TABLE 3-continued

Protein sequence of the VH and VL domains of the m825, m822, m830, and m863 antibodies (with IMGT CDRs in bold).

| Antibody | | protein sequence (CDRs underlined) |
|---|---|---|
| | VL | DIQLTQSPSSLSASVGDRVTITCRASRAISRYLNWYQQK PGKAPKLLIYAASSLQSGVSSRFSGSGSGTEFTLTISSL QPEDFATYFCQQTYSPPITFGQGTRLEIKR (SEQ ID NO: 8) |

The binding affinity of the m822, m825, m830, and m863 antibody interaction with TEM8 was assayed by surface plasmon resonance. The assay was performed on a Biacore instrument substantially as described (see, e.g., Feng et al., Mol Cancer Ther. 2006 January; 5(1):114-20.) using a for the m822, m825, m830, and m863 antibodies in IgG1 format and recombinant human TEM8 ectodomain. The apparent $K_D$ for m822, m825, m830, and m863 antibody binding to TEM8 determined by these assays is presented in Table 4.

TABLE 4

Binding affinities of the TEM8 antibodies measured by surface plasmon resonance

| Antibody | Calculated $K_D$ (M) |
|---|---|
| m822 | $3.5 \times 10^{-8}$ |
| m825 | $3.4 \times 10^{-11}$ |
| m830 | $1.2 \times 10^{-8}$ |
| m863 | $1.2 \times 10^{-9}$ |

The m825, m822, m830, and m863 were converted to human IgG according to standard methods (see, e.g., Zhu et al., J Virol. 2006 January; 80(2):891-9).

Figure 1B:
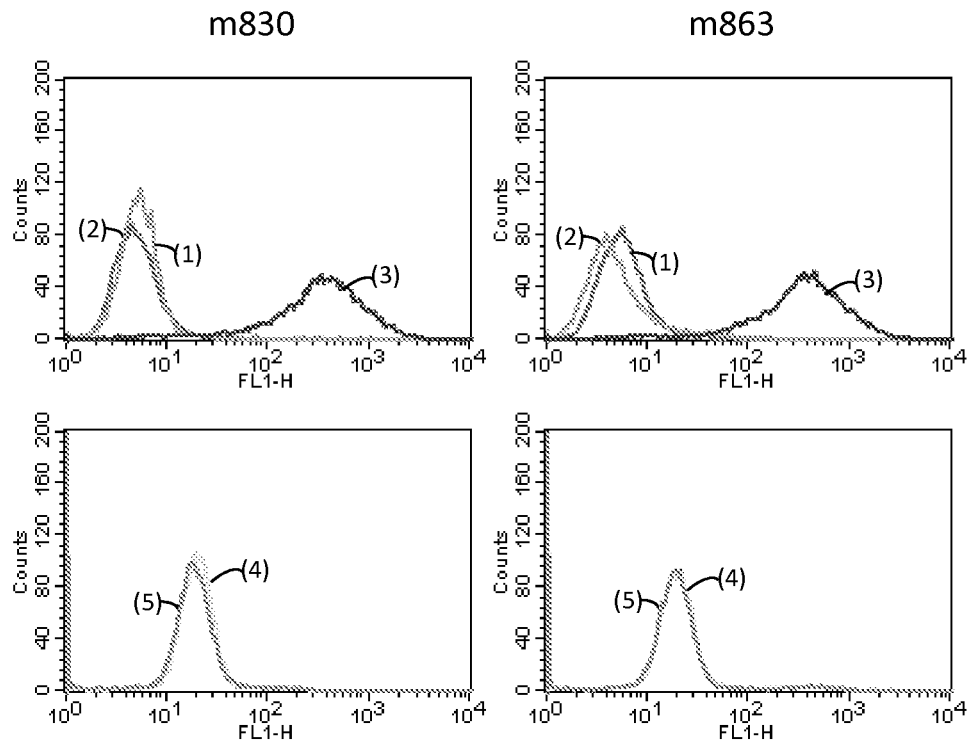

Screening assays were performed using the m825, m822, m830, and m863 antibodies in human IgG1 format to confirm that these antibodies can bind with high affinity to both human and mouse TEM8 in soluble form and also the cell surface native forms, but not human or mouse CMG2, a second receptor for anthrax toxin protein (ANTXR2). The screening assays were performed substantially as described in Chaudhary et al., Cancer Cell, 21:212-226, 2012, and PCT Pub. Nos. WO2012174160, each of which is incorporated herein in its entirety. Briefly, Chinese hamster ovary (CHO) cells or human embryonic kidney 293 (293) cells expressing human TEM8 (hTEM8) or human CMG2 (hCMG2) were incubated with the m825, m822, m830, or m863 antibody and binding was assayed using FACS analysis. The results show that each of the m825, m822, m830, and m863 antibodies bound to hTEM8 on the cell surface, but not to hCMG2 (see FIGS. 1A and 1B).

The m825, m822, m830, and m863 antibodies were also tested to determine if they can inhibit the binding of protective antigen (PA) subunit of anthrax toxin to TEM8 according to previously described methods (Chaudhary et al., Cancer Cell, 21:212-226, 2012, and PCT Pub. Nos. WO2012174160, each of which is incorporated herein in its entirety). Each of the m825, m822, m830, and m863 antibodies inhibited (PA) binding to TEM8.

Figure 2:
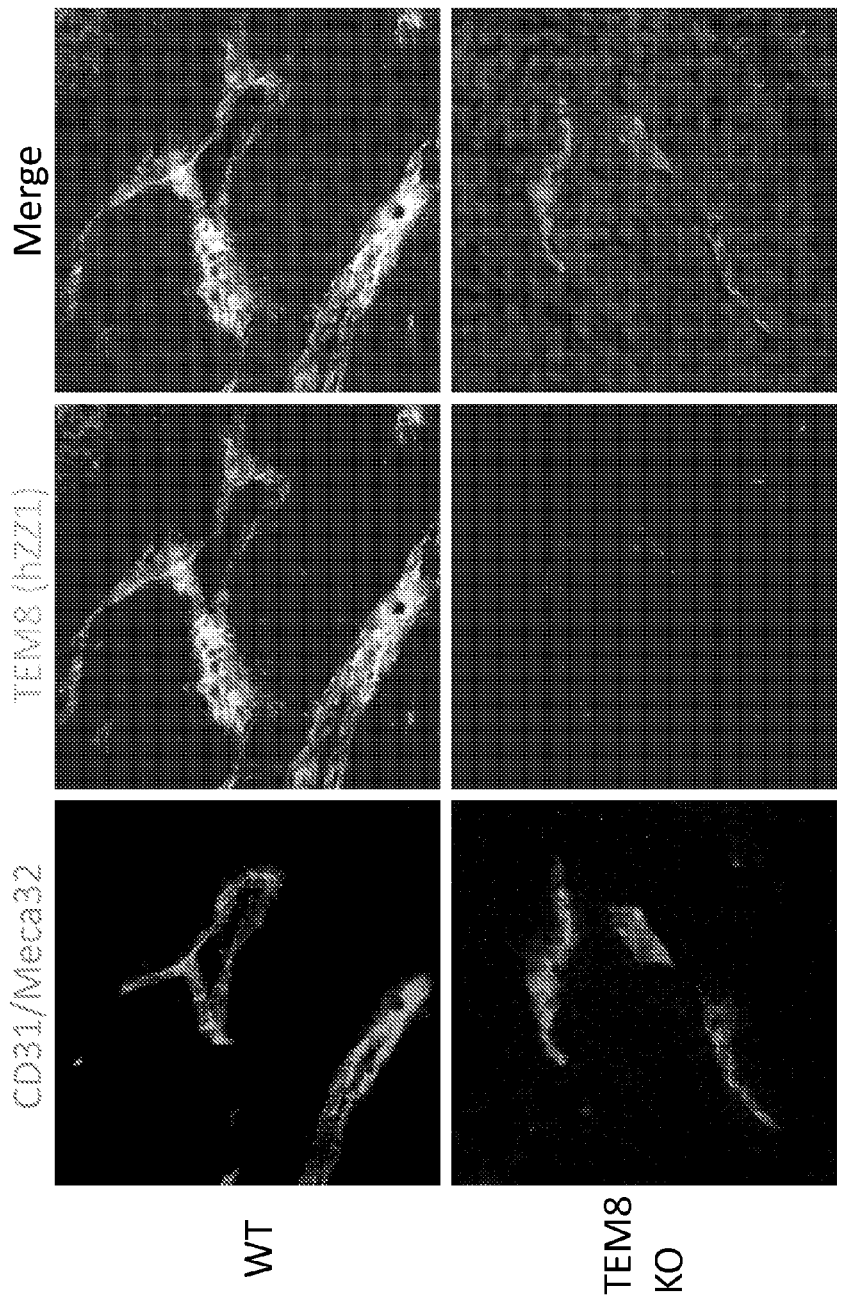
FIG. 2 shows a series of digital images illustrating immunofluorescent staining of tumor vessels using m825 antibody in a human IgG1 format. Wildtype (WT) and TEM8 knockout (TEM8 KO) mice were inoculated with DLD-1 colon cancer cells subcutaneously. After formation of the xenograft tumor, a sample from the tumor was obtained and stained with CD31 antibody (specific for blood vessels) and the m825 antibody (specific for TEM8). The m825 antibody stained the DLD-1 tumor vessels by immunofluorescence.

The m825, m822, m830, and m863 antibodies were also tested to determine if they can be used to label tumor vessels. Immunofluorescence staining assays were performed to determine if the m825 antibody in human IgG format (human m825-IgG1) would specifically label tumor blood vessels (FIG. 2). The assays were performed substantially as previously described (Chaudhary et al., Cancer Cell, 21:212-226, 2012, and PCT Pub. Nos. WO2012174160, each of which is incorporated herein in its entirety). Briefly, wild-type (WT) and TEM8 knockout TEM8 KO mice were administered DLD-1 cells subcutaneously and a xenograft tumor was allowed to develop. A sample from the tumor was obtained and stained with CD31 antibody (specific for blood vessels) and the human m825-IgG1 antibody. As illustrated in FIG. 2, the human m825-IgG1 specifically stained tumor vessels. This result indicates that the identified TEM8 antibodies can be used as diagnostic reagents for detections of tumor blood vessels.

Animal studies were performed to demonstrate that the antibodies inhibit tumor growth in vivo.

Figure 5:
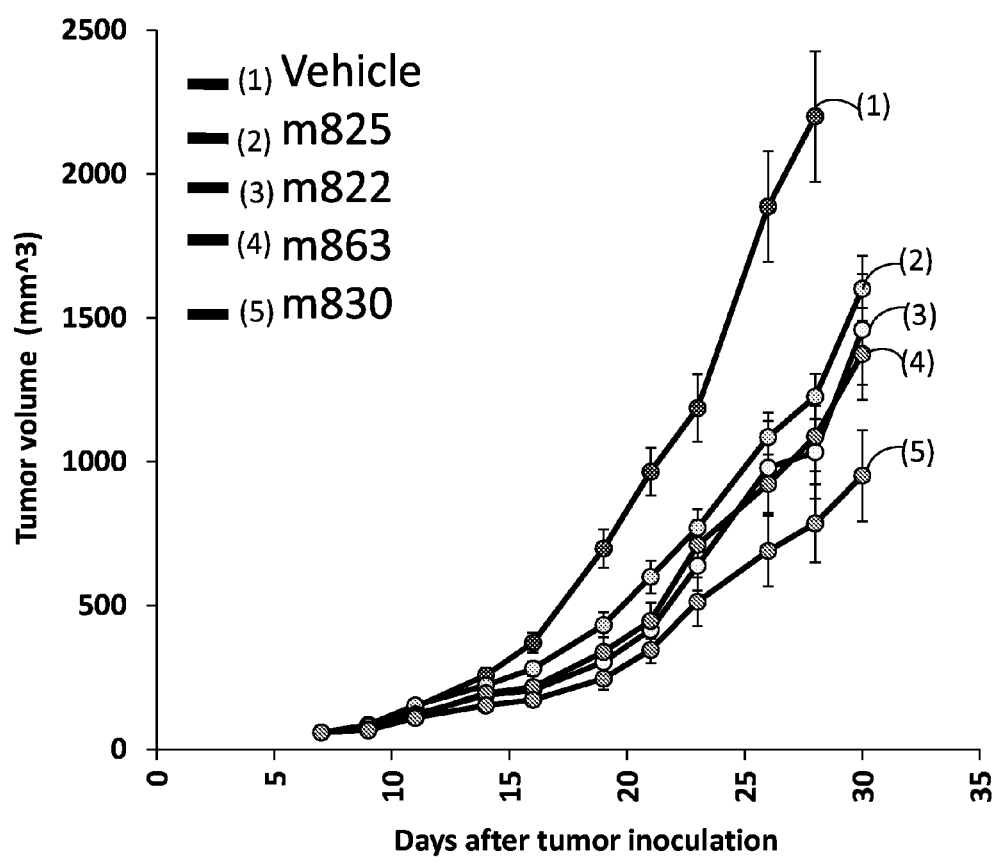
FIG. 5 is a graph illustrating inhibition of the growth of UACC melanoma cell xenografts grown subcutaneously in athymic nude mice by anti-TEM8 antibodies. Mice were inoculated with UACC melanoma cells subcutaneously, and the m825, m822, m830, and m863 antibodies in fully human IgG1 format were administered three time a week to the mice at a dose of 15 mg/Kg.

First, the human m825-IgG1 antibody was assayed for inhibition of UACC melanoma cell xenografts grown subcutaneously in athymic nude mice. The assay method used was substantially according to previously described methods (Chaudhary et al., Cancer Cell, 21:212-226, 2012, and PCT Pub. Nos. WO2012174160, each of which is incorporated herein in its entirety). Briefly, human m825-IgG1 antibody, control IgG, or control vehicle (PBS), were administered IP to the mice at a dose of 20 or 40 mg/kg starting 7 days after inoculation of the mice with the UACC cells (see arrows indicating treatment days in FIG. 3). Treatment with human inoculation of the mice with the UACC cells. Treatment with the m825, m822, m830, and m863 antibodies significantly reduced tumor volume over the course of the experiment compared to controls (FIG. 5).

Figure 6A:
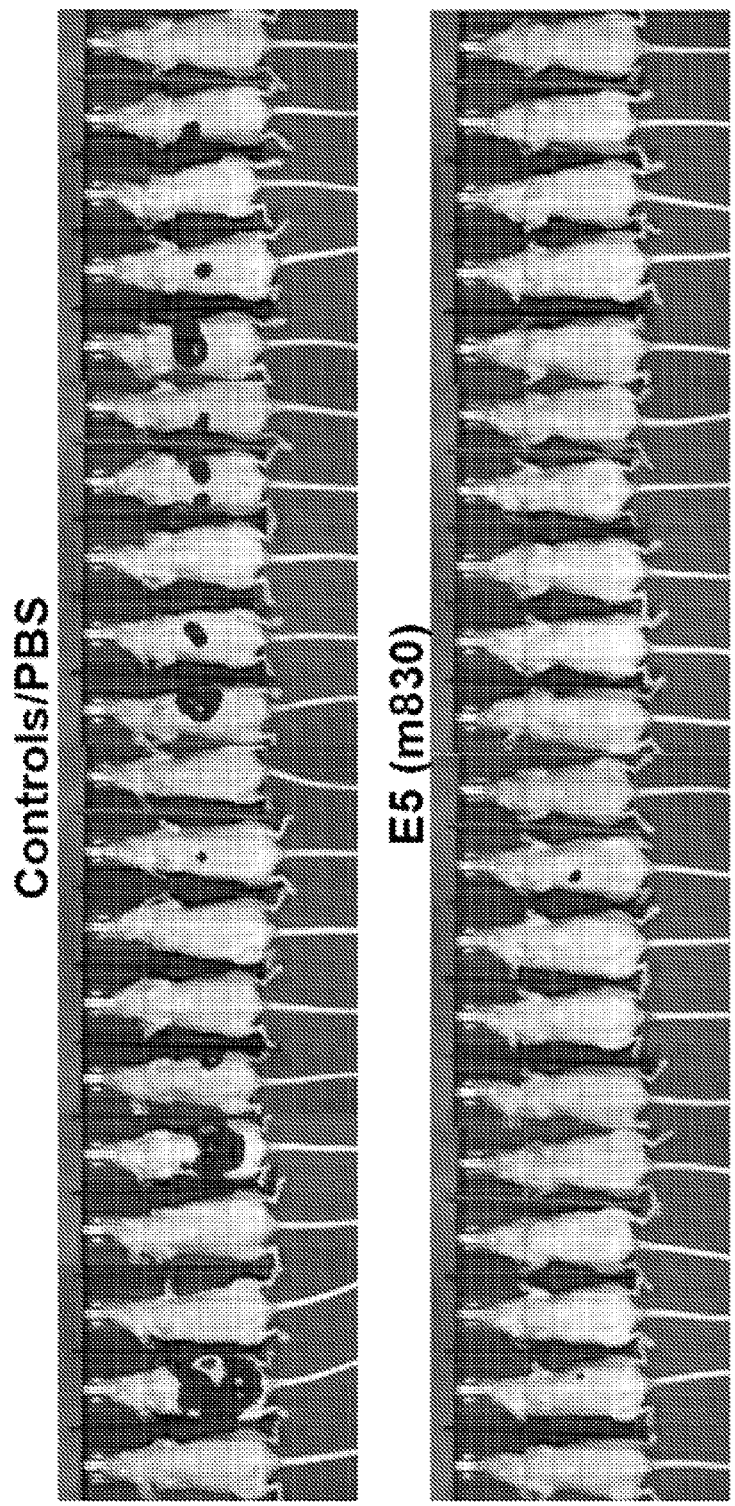
FIGS. 6A and 6B are set of digital images and a graph illustrating that treatment with m830 antibody inhibits colon cancer metastasis to liver in an animal model.
Figure 6B:
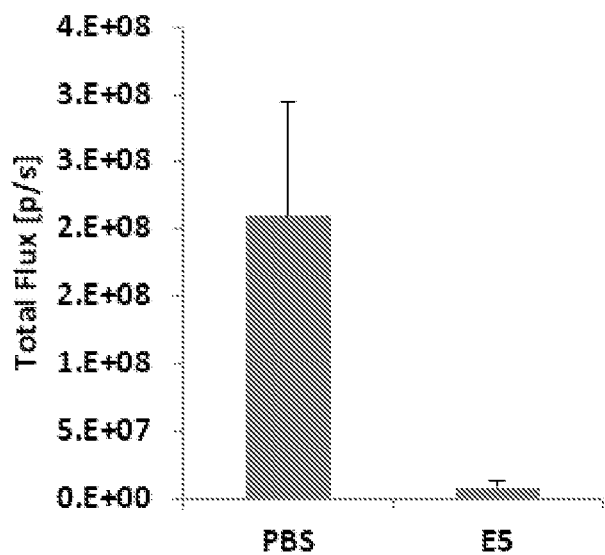

Additionally, assays were performed to determine if the anti-TEM8 antibodies could inhibit tumor metastasis in an animal model (FIG. 6). Athymic nude mice were injected intrasplenically with human colon cancer cells. The mice were then treated with the human m830-IgG1 antibody, and metastasis of the colon cancer to the liver of the mice was measured using bioluminescence. As shown in FIGS. 6 A and 6B, treatment with the human m830-IgG1 antibody drastically reduced metastasis in this animal model.

Figure 3:
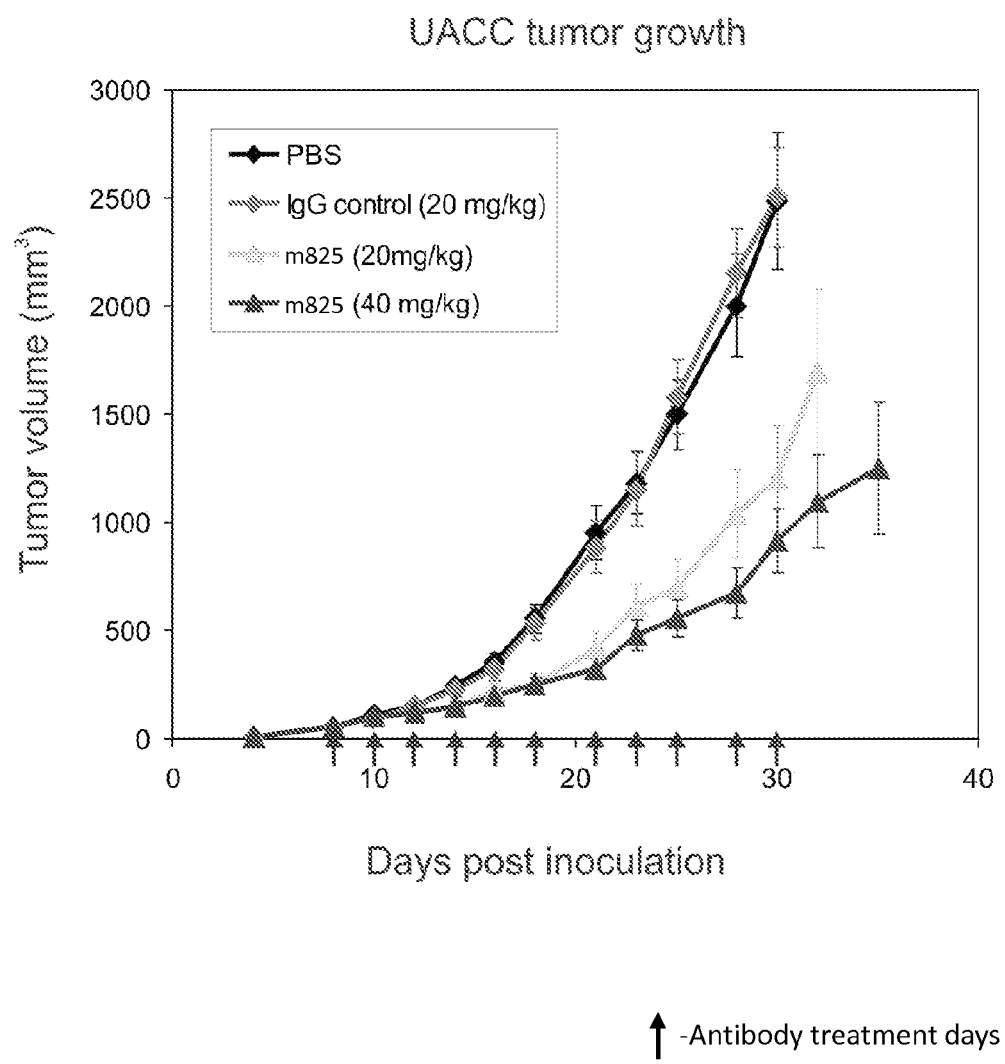
FIG. 3 is a graph illustrating inhibition of the growth of UACC melanoma cell xenografts by the m825 antibody in athymic nude mice. Mice were inoculated with UACC melanoma cells subcutaneously, and m825 antibody, control IgG, or control vehicle, were administered to the mice at a dose of 20 or 40 mg/Kg on each of the days indicated by an arrow on the graph.

An antibody drug conjugate including the m825 antibody (in human IgG1 format) conjugated to MMAE (m825-MMAE) was generated substantially according to previously described methods (see, e.g., U.S. Pub. Nos. 2011/0268751, 2008/0305044, 2007/0258987, each of which is incorporated by reference herein in its entirety). Briefly, inter-chain disulfide bonds of purified m825 antibody were partially reduced with tris (2-carboxyethyl)-phosphine hydrochloride (TCEP HCL) to form thiol groups. The reaction was performed at 25° C. for 1.5 hours with a TCEP concentration of 2.2 mole equivalents to m825 antibody. The partially reduced m825 antibody was incubated with MMAE toxin linked to a stretcher unit, a Val-Cit peptide cleavage site, and a spacer set forth as:

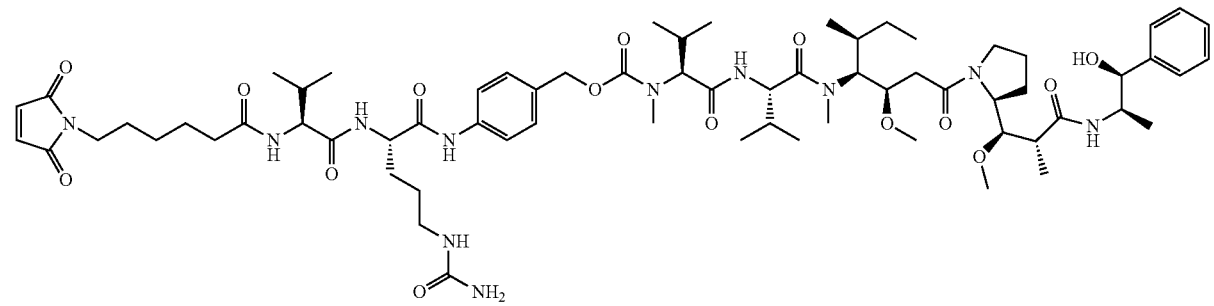 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

m825-IgG1 significantly reduced tumor volume over the course of the experiment compared to controls (FIG. 3).

Figure 4:
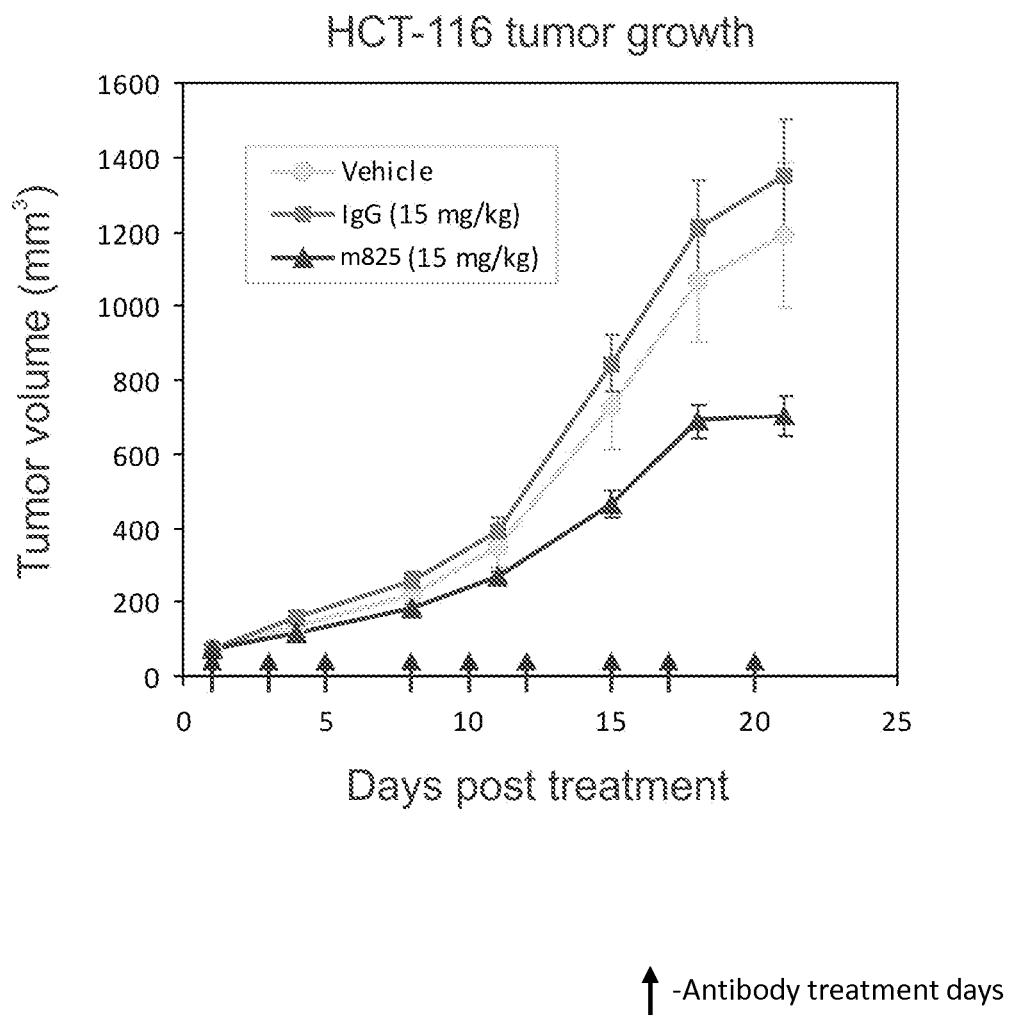
FIG. 4 is a graph illustrating that the m825 antibody inhibits the growth of HCT116 colon cancer cell xenografts grown subcutaneously in athymic nude mice. Mice were inoculated with HCT116 colon cancer cells subcutaneously, and m825 antibody, control IgG, or control vehicle, were administered to the mice at a dose of 15 mg/Kg on each of the days indicated by an arrow on the graph.

Additionally, human m825-IgG1 was assayed for inhibition of HCT-116 colon cancer cell xenografts grown subcutaneously in athymic nude mice. The assay method used was performed substantially according to previously described methods (Chaudhary et al., Cancer Cell, 21:212-226, 2012, and PCT Pub. Nos. WO2012174160, each of which is incorporated herein in its entirety). Briefly, human m825-IgG1 antibody, control IgG, or control vehicle (PBS), were administered IP to the mice at a dose of 15 mg/kg on after inoculation of the mice with the HCT-116 cells (see arrows indicating treatment days in FIG. 4). Treatment with human m825-IgG1 significantly reduced tumor volume over the course of the experiment compared to controls (FIG. 4).

Further, the m825, m822, m830, and m863 antibodies in human IgG format were each assayed for inhibition of UACC melanoma cell xenografts grown subcutaneously in athymic nude mice (FIG. 5). The assay method used was substantially according to previously described methods (Chaudhary et al., Cancer Cell, 21:212-226, 2012, and PCT Pub. Nos. WO2012174160, each of which is incorporated herein in its entirety). Briefly, m825, m822, m830, or m863 antibody, or control vehicle (PBS), was administered IP to the mice at a dose of 15 mg/kg on the seventh day after The reaction was performed at 25° C. for 1 hour with the MMAE compound concentration of 5.5 mole equivalents to m825 antibody. DMSO was included in the reaction at 10.5% v/v to maintain solubility of the MMAE linker. The conjugation reaction was then quenched by adding a 10× molar ration of N-Acetyl-L-Cysteine relative to m825 antibody at 25° C. for 15 minutes. The resulting m825-MMAE conjugate was subjected to buffer exchange using standard methods, and concentrated as needed.

Figure 7:
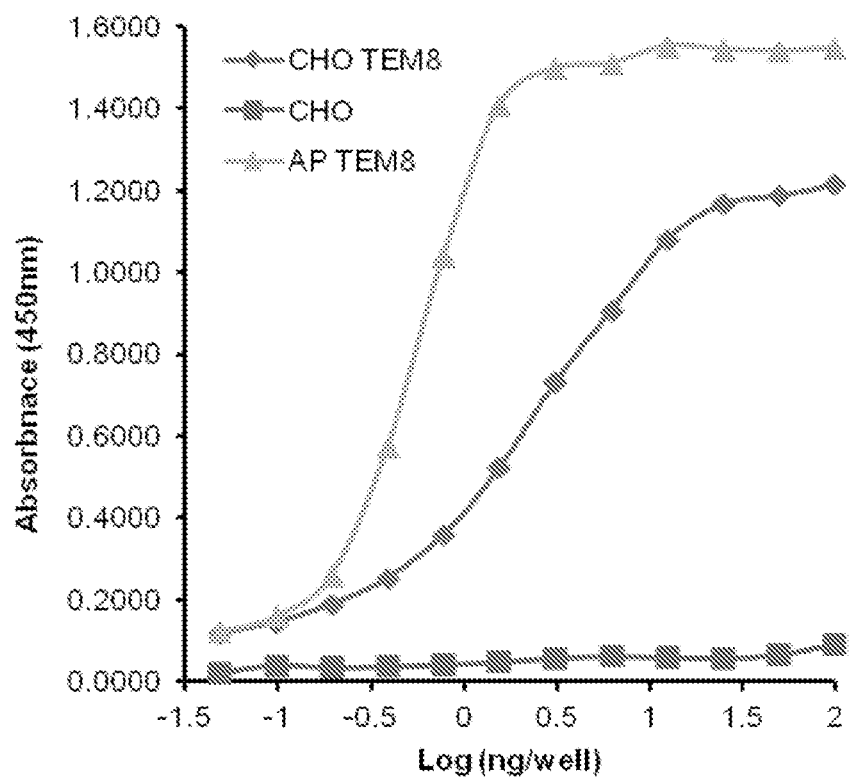
FIG. 7 is a graph illustrating binding of an antibody drug conjugate including the fully human m825 antibody conjugated to the MMAE toxin to recombinant TEM8 (AP-TEM8) as well as CHO cells overexpressing TEM8 (CHO TEM8). CHO cells that do not express TEM8 (CHO) were used as a negative control.

The m825-MMAE conjugate was tested for binding to cell-surface TEM8 by assaying binding to CHO cells expressing human TEM8. As shown in FIG. 7, the m825-MMAE conjugate specifically bound to the TEM8 expressing CHO cells, but not to control CHO cells lacking TEM8 expression.

Figure 8:
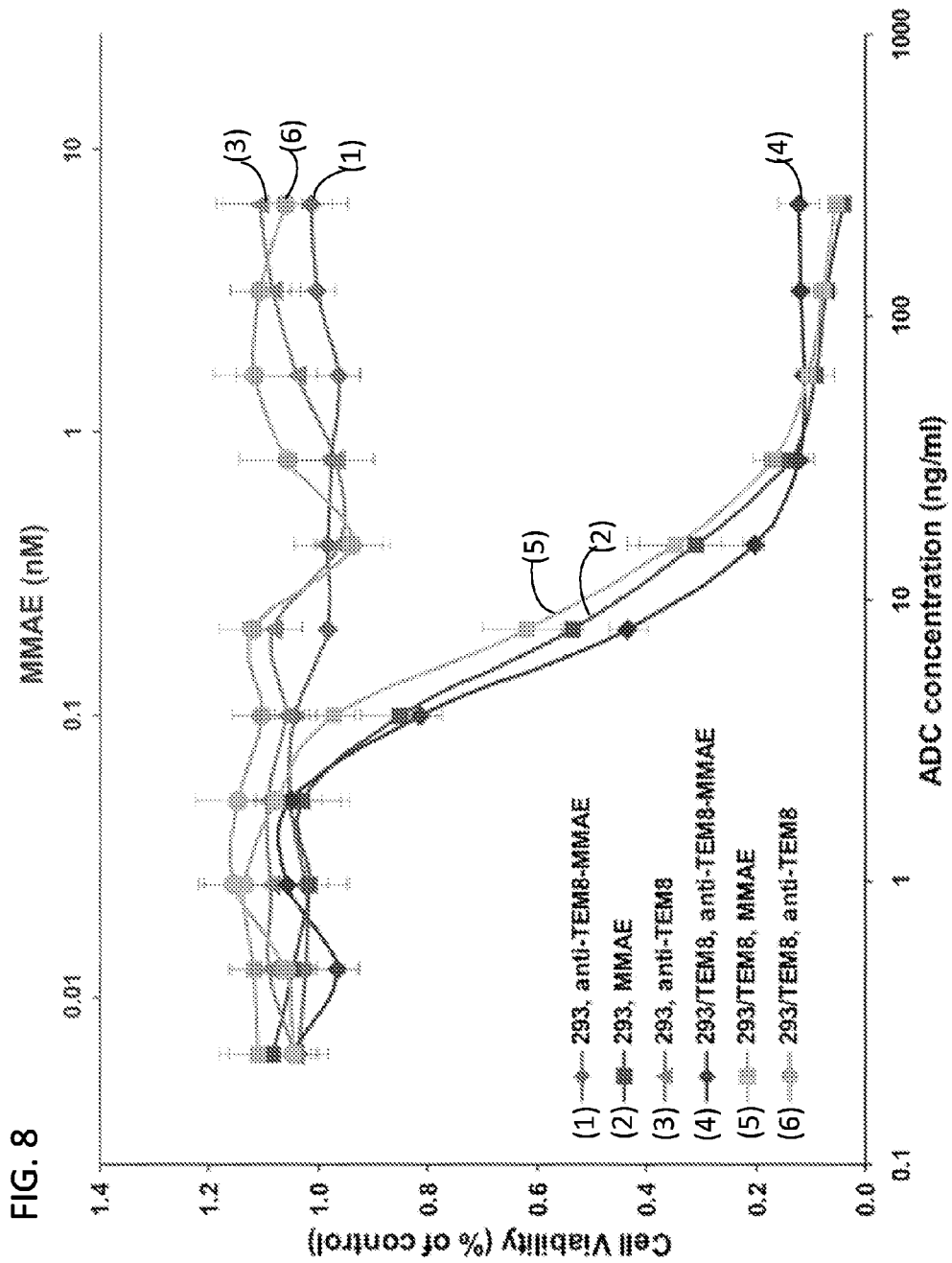
FIG. 8 is a graph illustrating that an antibody drug conjugate including the fully human m825 antibody conjugated to the MMAE toxin is selectively cytotoxic towards cells expressing TEM8. HEK 293 cells (293) or HEK 293 cells transfected with TEM8 (293/TEM8) were treated with MMAE alone (MMAE), m825 alone (anti-TEM8), or an antibody drug conjugate including the fully human m825 antibody conjugated to MMAE (anti-TEM8-MMAE). The MMAE toxin was cytotoxic towards both 293 and 293/TEM8 cells, whereas the antibody drug conjugate was selectively cytotoxic towards 293/TEM8 cells.

The selectivity of the m825-MMAE conjugate for TEM8 expressing cells was assayed in vitro (FIG. 8). HEK 293 cells (control) or HEK 293 cells expressing TEM8 were treated with MMAE alone, human m825-IgG1 antibody, or the m825-MMAE conjugate. As shown in FIG. 8, the MMAE toxin alone was cytotoxic towards HEK 293 cells regardless of TEM8 expression, whereas the m825-MMAE conjugate was only cytotoxic toward HEK-293 cells expressing TEM8.

Figure 9:
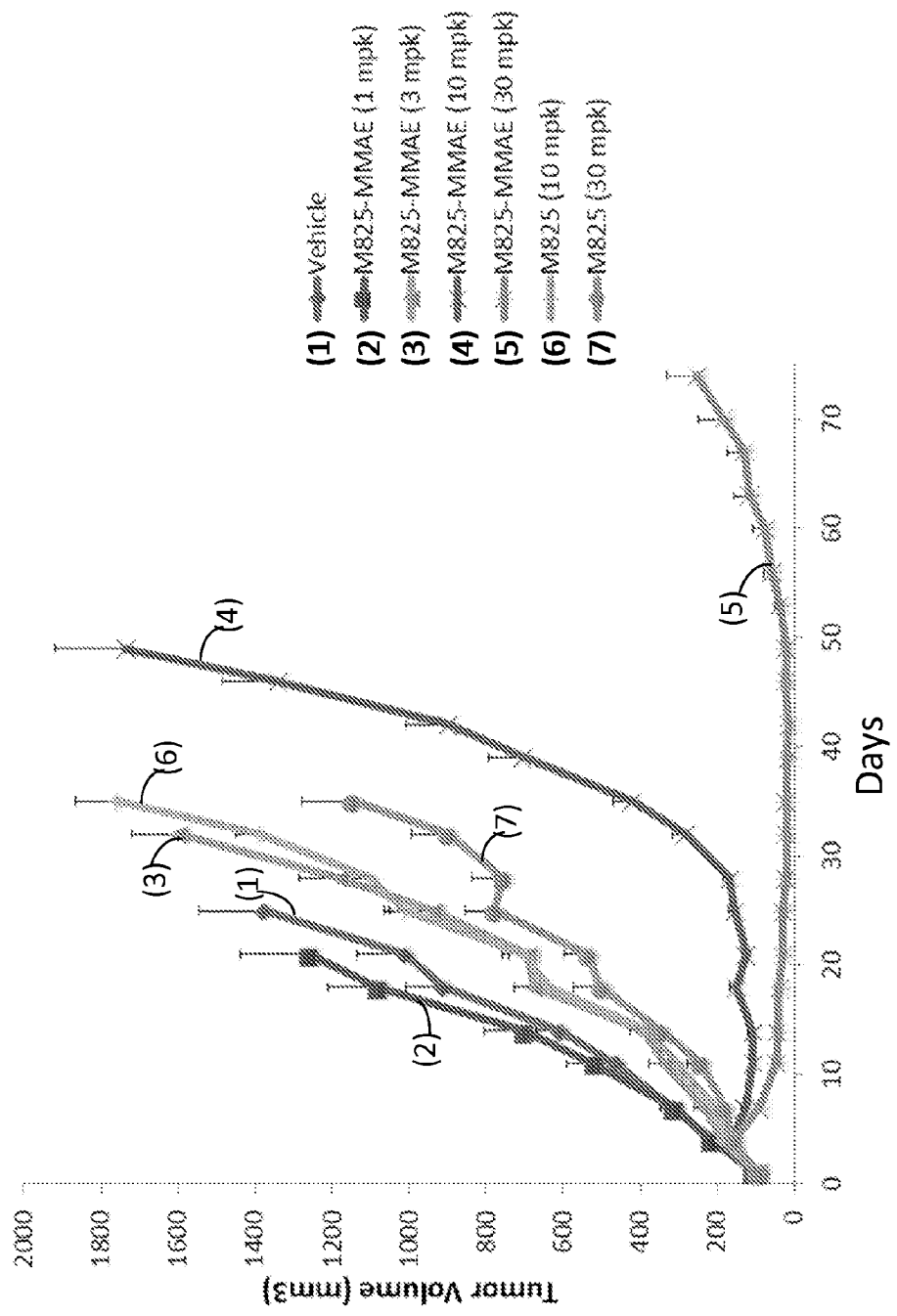
FIG. 9 is a graph illustrating regression of human colon cancer xenografts following treatment with an antibody drug conjugate including the fully human m825 antibody conjugated to MMAE (m825-MMAE). Colon cancer xenografts (HCT116 cells) were grown subcutaneously in Athymic nude mice. The mice were administered the indicated amount (mg/kg, mpk) of vehicle, m825 antibody alone (M825), or m825-MMAE, twice a week for three weeks.
Figure 10:
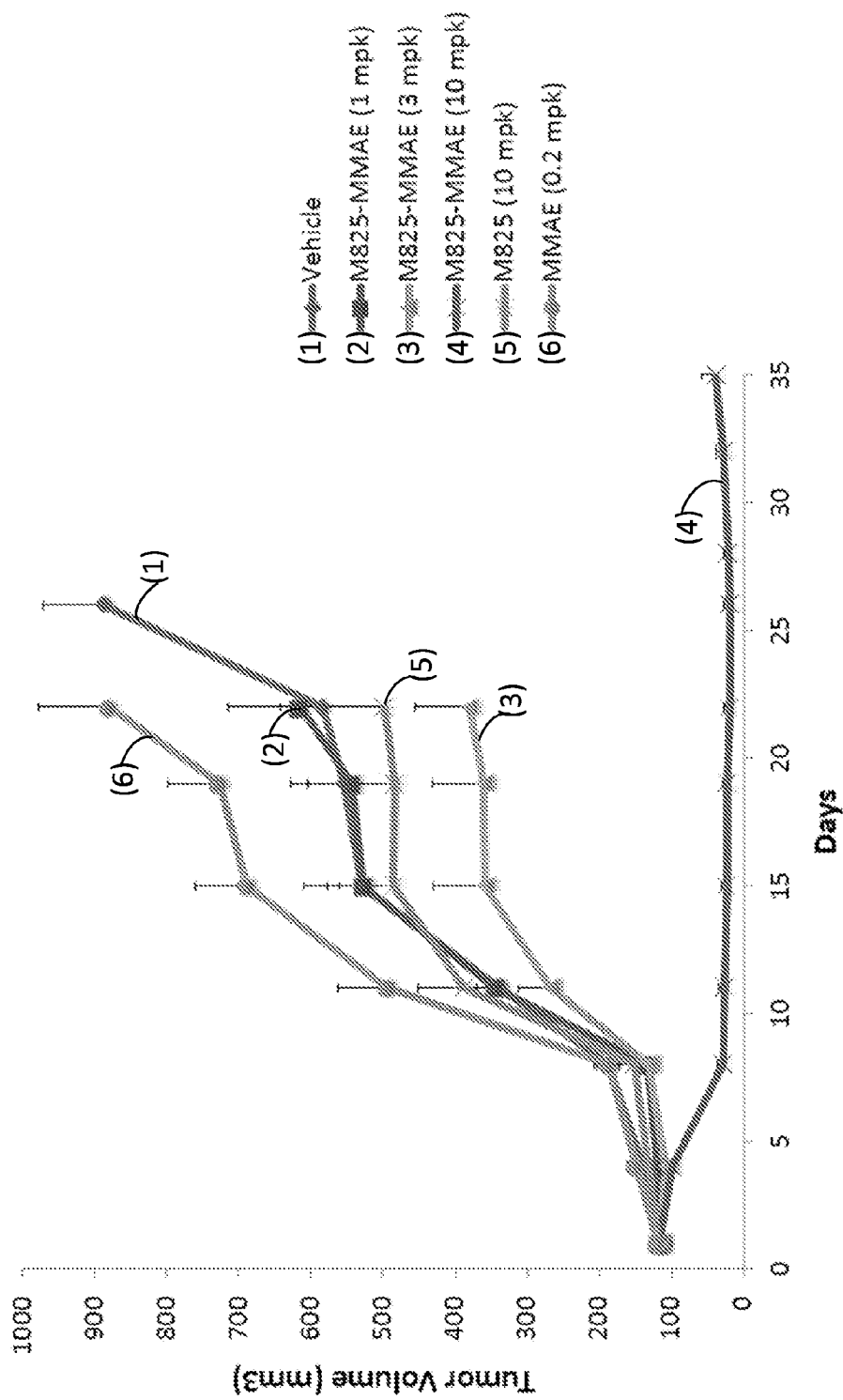
FIG. 10 is a graph illustrating regression of human ovarian cancer xenografts following treatment with an antibody drug conjugate including the fully human m825 antibody conjugated to MMAE. Ovarian cancer xenografts (OVCAR3 cells) were grown subcutaneously in Athymic nude mice. The mice were administered the indicated amount (mg/kg, mpk) of vehicle, m825 antibody alone (M825), MMAE alone, or m825-MMAE twice a week for three and a half weeks.

To further assay the anti-cancer activity of anti-TEM8 antibodies and antibody-drug conjugates thereof, the effects of these compounds on xenograft growth in Athymic nude mice was tested (FIGS. 9 and 10). Human colon cancer xenografts (HCT116 cells) were grown subcutaneously in Athymic nude mice. The mice were treated with the m825-MMAE conjugate at a concentration of 1, 3, 10, or 30 mg/kg, or human m825-IgG1 antibody alone at a concentration of 10 or 30 mg/kg, twice a week for three weeks. The results indicate that both the human m825-IgG1 antibody and the m825-MMAE conjugate successfully reduced tumor growth in this animal model. Additionally, at comparable dosages, the m825-MMAE conjugate was more effective at reducing tumor growth that m825 antibody alone.

Additionally, ovarian cancer xenografts (OVCAR3 cells) were grown subcutaneously in Athymic nude mice. The mice were treated with the m825-MMAE conjugate (1, 3, or 10 mg/kg), human m825-IgG1 antibody alone (10 mg/kg), or MMAE alone (0.2 mg/kg), twice a week for three and a half weeks. The results show that the m825-MMAE conjugate (at 3 and 10 mg/kg) reduced xenograft growth in this animal model. Additionally, at comparable dosages, the m825-MMAE conjugate was more effective at reducing tumor growth that m825 antibody alone.

These in vivo assays illustrate that the m825, m822, m830, and m863 antibodies, and antibody-drug-conjugates thereof, can be used as cancer therapeutics.

Example 2

Detection of an Endothelial Cell that Expresses TEM8 in a Human

This example describes particular methods that can be used to detect an endothelial cell that expresses TEM8 in a subject. However, one skilled in the art will appreciate that similar methods can be used. Such detection may be performed, for example, before, during, or after, treating the subject (or combination thereof) with an antibody that specifically binds TEM8 or conjugate thereof.

A TEM8 specific monoclonal antibody (such, but not limited to, a TEM8 specific monoclonal antibody including a heavy chain variable region including a H-CDR1, H-CDR2, and H-CDR3 including amino acids 26-33, 51-58, and 97-106 of SEQ ID NO: 1, respectively, and a light chain variable region including a L-CDR1, L-CDR2, and L-CDR3 including amino acids 26-31, 49-51, and 88-97 of SEQ ID NO: 2, respectively) or a TEM8 specific monoclonal antibody conjugated to a detectable marker is administered to the subject. Administration can be achieved by any sufficient method known in the art, but is typically intravenous administration. Typically, the conjugate is administered as a component of a composition including the conjugate and a pharmaceutically acceptable carrier.

An effective amount of the antibody or conjugate is administered to the subject. The amount of antibody or conjugate administered is sufficient to form a detectable immune complex with TEM8 in the subject. A effective amount can being readily determined by one skilled in the art, for example using routine trials establishing dose response curves. In addition, particular exemplary dosages are provided above. The antibody or conjugate can be administered in single or multiple dose delivery or via continuous delivery over an extended time period.

In the case of an antibody, the antibody utilized for detection of pathological angiogenesis in a subject is detected with a secondary reagent (such as a secondary antibody conjugated to a detectable marker) useful for diagnostic imaging. For example, a detectable marker used for magnetic resonance imaging, such as super paramagnetic iron oxide nanocrystals. The particular secondary reagent will depend on the particular type of diagnostic imaging utilizes, as will be appreciated by the skilled artisan.

In the case of a conjugate, the conjugate utilized for detection of pathological angiogenesis in a subject typically includes a detectable marker useful for diagnostic imaging. For example, a detectable marker used for magnetic resonance imaging, such as super paramagnetic iron oxide nanocrystals. The particular detectable marker will depend on the particular type of diagnostic imaging utilizes, as will be appreciated by the skilled artisan.

Detection of the endothelial cell that expresses TEM8 is accomplished by detecting the antibody or conjugate immobilized in the subject using the diagnostic imaging method corresponding to the detectable marker used. For example, if the detectable marker is super paramagnetic iron oxide nanocrystals, then the diagnostic imaging methods will typically include magnetic resonance imaging.

Example 3

Treatment of Cancer in a Human

This example describes a particular method that can be used to treat a primary or metastatic tumor in humans by administration of one or more antibodies that specifically bind TEM8 or a conjugate thereof. Although particular methods, dosages, and modes of administrations are provided, one skilled in the art will appreciate that variations can be made without substantially affecting the treatment.

Human patients are treated intravenously with at least 1 µg (such as 0.001-1000 mg) of one or more antibodies that specifically bind TEM8 or conjugate thereof, (such, but not limited to, a TEM8 specific monoclonal antibody including a heavy chain variable region including a H-CDR1, H-CDR2, and H-CDR3 including amino acids 26-33, 51-58, and 97-106 of SEQ ID NO: 1, respectively, and a light chain variable region including a L-CDR1, L-CDR2, and L-CDR3 including amino acids 26-31, 49-51, and 88-97 of SEQ ID NO: 2, respectively), for example for a period of at least 1 day, 1 week, 1 month, at least 2 months, at least 3 months, at least 6 months, at least one year, at least 2 years, or at least five years or more or less time. Administration of the antibody or conjugate can be used in conjunction with normal cancer therapy (for example rather than replacing the therapy). Thus, the antibody or conjugate can be added to the usual and customary anti-angiogenic, chemotherapy, surgery, radiation treatments (or combination thereof) conventionally used for the particular tumor type. Administration of the antibody or conjugate can be continued after customary therapy was stopped and can be taken long term (for example over a period of months or years).

Briefly, the method includes screening subjects to determine if they have a tumor, such as a primary or metastatic tumor. Subjects having a tumor are selected. In a clinical trial, half of the subjects would follow the established protocol for treatment of the tumor (such as a normal anti-angiogenic/chemotherapy/radiotherapy/surgery regimen). The other half would follow the established protocol for treatment of the tumor (such as a normal anti-angiogenic/chemotherapy/radiotherapy/surgery regimen) in combination with administration of the a antibody or conjugate described herein. In some examples, the tumor is surgically excised (in whole or part) prior to treatment with the antibody or conjugate.

Screening Subjects

The subject is first screened to determine if they have a tumor. Examples of methods that can be used to screen for tumors include a combination of ultrasound, tissue biopsy, or detection of tumor-associated vasculature. However, such pre-screening is not required prior to administration of the antibody or conjugate disclosed herein.

Pre-Treatment of Subjects

The subject is treated prior to administration of an antibody that specifically binds TEM8 or conjugate thereof. However, such pre-treatment is not always required, as can be determined by a skilled clinician. For example, the tumor can be surgically excised (in total or in part) prior to administration of one or more antibodies or conjugates. In addition, the subject can be treated with an established protocol for treatment of the particular tumor present (such as a normal anti-angiogenesis/chemotherapy/radiotherapy regimen).

Administration

Administration can be achieved by any sufficient method known in the art, but is typically intravenous administration. Typically, the antibody or conjugate is administered as a component of a composition including the antibody or conjugate and a pharmaceutically acceptable carrier.

A therapeutically effective amount of the antibody or conjugate is administered to the subject. The amount of antibody or conjugate administered is sufficient to treat a subject having a tumor. A therapeutically effective amount can be readily determined by one skilled in the art, for example using routine trials establishing dose response curves. In addition, particular exemplary dosages are provided above. The antibody or conjugate can be administered in a single dose delivery, via continuous delivery over an extended time period, in a repeated administration protocol (for example, by a daily, weekly, or monthly repeated administration protocol).

Assessment

Following the administration of one or more therapies, subjects having a tumor can be monitored for tumor treatment, such as regression or reduction in tumor burden (for example, reduction in metastatic lesions). In particular examples, subjects are analyzed one or more times, starting seven days following treatment.

Subjects can be monitored using any method known in the art. For example, diagnostic imaging can be used (such as x-rays, CT scans, MRIs, ultrasound, fiber optic examination, and laparoscopic examination), as well as analysis of biological samples from the subject (for example analysis of blood, tissue biopsy, or other biological samples), such as analysis of the type of cells present, or analysis for a particular tumor marker. In one example, if the subject has a metastatic tumor, assessment can be made using ultrasound, MRI, or CAT scans and analysis of the type of cells contained in a tissue biopsy.

In view of the many possible embodiments to which the principles of the disclosed embodiments may be applied, it should be recognized that the illustrated embodiments are only preferred examples of the invention and should not be taken as limiting. We therefore claim all that comes within the scope and spirit of the following claims.

We claim:

1. An isolated monoclonal antibody or antigen binding fragment thereof, comprising a heavy chain variable region and a light chain variable region, comprising one of:
   (a) a heavy chain complementarity determining region (H-CDR)1, a H-CDR2, and a H-CDR3 of the heavy chain variable region set forth as SEQ ID NO: 1, and a light chain complementarity determining region (L-CDR)1, a L-CDR2, and a L-CDR3 of the light chain variable region set forth as SEQ ID NO: 2 (m825);
   (b) a H-CDR1, a H-CDR2, and a H-CDR3 of the heavy chain variable region set forth as SEQ ID NO: 3, and a L-CDR1, a L-CDR2, and a L-CDR3 of the light chain variable region set forth as SEQ ID NO: 4 (m822);
   (c) a H-CDR1, a H-CDR2, and a H-CDR3 of the heavy chain variable region set forth as SEQ ID NO: 5, and a L-CDR1, a L-CDR2, and a L-CDR3 of the light chain variable region set forth as SEQ ID NO: 6 (m830); or
   (d) a H-CDR1, a H-CDR2, and a H-CDR3 of the heavy chain variable region set forth as SEQ ID NO: 7, and a L-CDR1, a L-CDR2, and a L-CDR3 of the light chain variable region set forth as SEQ ID NO: 8 (m863); and
   wherein the monoclonal antibody or antigen binding fragment specifically binds to tumor endothelial marker 8 (TEM8) and is neutralizing.

2. The antibody or antigen binding fragment of claim 1, wherein:
   (a) the H-CDR1, H-CDR2, and H-CDR3, comprise amino acids 26-33, 51-58, and 97-106 of SEQ ID NO: 1, respectively, and the L-CDR1, L-CDR2, and L-CDR3 comprise amino acids 26-31, 49-51, and 88-97 of SEQ ID NO: 2, respectively (m825);
   (b) the H-CDR1, H-CDR2, and H-CDR3, comprise amino acids 26-33, 51-58, and 97-106 of SEQ ID NO: 3, respectively, and the L-CDR1, L-CDR2, and L-CDR3 comprise amino acids 26-31, 49-51, and 88-97 of SEQ ID NO: 4, respectively (m822);
   (c) the H-CDR1, H-CDR2, and H-CDR3, comprise amino acids 26-33, 51-58, and 97-110 of SEQ ID NO: 5, respectively, and the L-CDR1, L-CDR2, and L-CDR3 comprise amino acids 27-32, 50-52, and 89-97 of SEQ ID NO: 6, respectively (m830); or
   (d) the H-CDR1, H-CDR2, and H-CDR3, comprise amino acids 26-33, 51-58, and 97-110 of SEQ ID NO: 7, respectively, and the L-CDR1, L-CDR2, and L-CDR3 comprise amino acids 27-32, 50-52, and 89-97 of SEQ ID NO: 8, respectively (m863).

3. The antibody or antigen binding fragment of claim 1, comprising:
   (a), wherein the heavy chain variable region comprises the amino acid sequence set forth as SEQ ID NO: 1;
   (b), wherein the heavy chain variable region comprises the amino acid sequence set forth as SEQ ID NO: 3;
   (c), wherein the heavy chain variable region comprises the amino acid sequence set forth as SEQ ID NO: 5; or
   (d), wherein the heavy chain variable region comprises the amino acid sequence set forth as SEQ ID NO: 7.

4. The antibody or antigen binding fragment of claim 1, comprising:
   (a), wherein the light chain variable region comprises the amino acid sequence set forth as SEQ ID NO: 2;
   (b), wherein the light chain variable region comprises the amino acid sequence set forth as SEQ ID NO: 4;
   (c), wherein the light chain variable region comprises the amino acid sequence set forth as SEQ ID NO: 6; or
   (d), wherein the light chain variable region comprises the amino acid sequence set forth as SEQ ID NO: 8.

5. The antibody or antigen binding fragment of claim 1, wherein the heavy and light chain variable regions comprise the amino acid sequences set forth as
   (a) SEQ ID NO: 1 and SEQ ID NO: 2, respectively;
   (b) SEQ ID NO: 3 and SEQ ID NO: 4, respectively;
   (c) SEQ ID NO: 5 and SEQ ID NO: 6, respectively; or
   (d) SEQ ID NO: 7 and SEQ ID NO: 8, respectively.

6. The antibody of claim 1, wherein the monoclonal antibody or antigen binding fragment comprises a human framework region.

7. The antibody of claim 1, wherein the antibody is an IgG.

8. The antibody of claim 1.

9. The antigen binding fragment of claim 1.

10. The antigen binding fragment of claim 9, wherein the antigen binding fragment is a Fv, Fab, F(ab')$_2$, scFV or a scFV$_2$ fragment.

11. The antibody or antigen binding fragment of claim 1, conjugated to an effector molecule or a detectable marker.

12. The antibody or antigen binding fragment of claim 11, wherein the effector molecule is an anti-angiogenic agent, chemotherapeutic agent, and/or toxin.

13. The antibody or antigen binding fragment of claim 12, wherein the toxin is a maytansinoid toxin and/or an auristatin toxin.

14. The isolated monoclonal antibody or antigen binding fragment of claim 13, wherein
the maytansinoid toxin is DM1; and/or
the auristatin toxin is Monomethyl Auristatin E (MMAE) or Monomethyl Auristatin F (MMAF).

15. The antibody or antigen binding fragment of claim 11, wherein the antibody or antigen binding fragment is conjugated to the effector molecule by a linker.

16. The antibody or antigen binding fragment of claim 15, wherein the linker is a cleavable linker.

17. The antibody or antigen binding fragment of claim 16, wherein the linker is a cathepsin-cleavable linker.

18. The antibody or antigen binding fragment of claim 15, wherein the linker is a selectively cleavable peptide linker.

19. The antibody or antigen binding fragment of claim 15, wherein the linker is a non-cleavable linker.

20. The antibody or antigen binding fragment of claim 11, wherein the detectable marker is a fluorescent, enzymatic, heavy metal or radioactive marker.

21. An isolated nucleic acid molecule encoding the antibody or antigen binding fragment of claim 1.

22. The nucleic acid molecule of claim 21, encoding a chimeric antigen receptor.

23. A vector comprising the nucleic acid molecule of claim 21.

24. The vector of claim 23, for use in making a chimeric antigen receptor T cell.

25. A host cell, comprising the nucleic acid molecule of claim 21 or a vector comprising the nucleic acid molecule.

26. The host cell of claim 25, wherein the host cell is a T cell.

27. An antibody-drug-conjugate according to formula I:

region (H-CDR)1, a H-CDR2, and a H-CDR3 comprising amino acids 26-33, 51-58, and 97-106 of SEQ ID NO: 1, respectively, and a light chain variable region comprising a light chain complementarity determining region (L-CDR)1, a L-CDR2, and a L-CDR3 comprising amino acids 26-31, 49-51, and 88-97 of SEQ ID NO: 2, respectively, wherein the antibody or antigen binding fragment specifically binds to tumor endothelial marker 8 (TEM 8);
wherein S is a sulfur atom of the antibody; and
wherein n is an integer between 1 and 10.

28. The antibody drug conjugate of claim 27, wherein the heavy chain variable region comprises the amino acid sequence set forth as SEQ ID NO: 1 and the light chain variable region comprises the amino acid sequence set forth as SEQ ID NO: 2.

29. The antibody drug conjugate of claim 27, wherein n is an even integer from 2 to 8.

30. The antibody drug conjugate of claim 27, wherein n is an even integer from 2 to 4.

31. A composition, comprising an effective amount of the antibody or antigen binding fragment of claim 1, a nucleic acid molecule encoding the antibody or antigen binding fragment, or an antibody drug conjugate comprising the antibody or antigen binding fragment, and a pharmaceutically acceptable carrier.

32. A kit for detecting pathological angiogenesis in a subject, treating a tumor in a subject, or decreasing the binding of Anthrax protective antigen to a cell, comprising a container comprising the antibody or antigen binding fragment of claim 1, or a nucleic acid molecule encoding the antibody or antigen binding fragment, or a vector comprising the nucleic acid molecule, or an antibody drug conjugate comprising the antibody or antigen binding fragment, or a

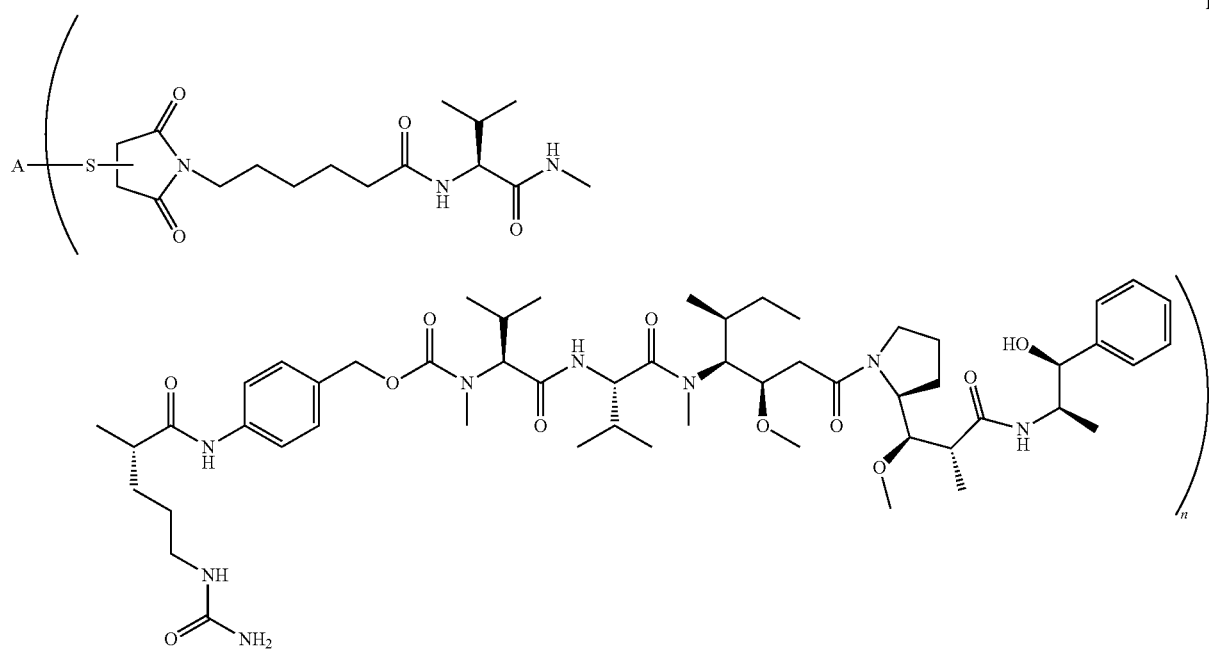

I wherein A is an antibody or antigen binding fragment thereof comprising a heavy chain variable region comprising a heavy chain complementarity determining composition comprising the antibody, antigen binding fragment, nucleic acid molecule, vector, or antibody drug conjugate, and instructions for using the kit.

33. A method of treating a subject with a tumor, comprising:
selecting a subject with a tumor; and
administering to the subject a therapeutically effective amount of the antibody or antigen binding fragment of claim 1 under conditions sufficient to form an immune complex, wherein formation of the immune complex treats the tumor in the subject.

34. The method of claim 33, further comprising administering to the subject a therapeutically effective amount of an anti-angiogenic agent or a chemotherapeutic agent.

35. The method of claim 33, wherein the antibody or antigen binding fragment is conjugated to a maytansinoid toxin and/or an auristatin toxin.

36. The method of claim 35, wherein: the maytansinoid toxin is DM1; and/or the auristatin toxin is Monomethyl Auristatin E (MMAE) or Monomethyl Auristatin F (MMAF).

37. The method of claim 33, wherein the tumor is colorectal, skin, lung, breast, prostate, or head and neck cancer.

38. The method of claim 33, wherein treating the tumor comprises a reduction in tumor burden and/or a reduction in tumor growth.

39. The method of claim 33, wherein the tumor is in a tumor microenvironment comprising a cell with increased cell surface expression of TEM8.

40. The method of claim 39, wherein the cell is an endothelial cell or a stromal cell.

41. A method of detecting the presence of a cell with cell-surface expression of TEM8 in a subject, comprising:
contacting a cell from the subject with an effective amount of the antibody or antigen binding fragment of claim 1 under conditions sufficient to form an immune complex; and
detecting the presence of the immune complex on the cell from the subject, wherein the presence of the immune complex on the cell from the subject indicates the presence of an cell with cell-surface expression of TEM8 in the subject.

42. The method of claim 41, wherein the contacting is in vivo.

43. The method of claim 41, wherein the contacting is in vitro.

44. The method of claim 43, wherein the cell is in a biological sample from the subject.

45. The method of claim 41, wherein the cell is an endothelial cell, a tumor stromal cell, and/or a tumor cell.

46. The method of claim 41, wherein the cell is an endothelial cell, and wherein detecting the presence of the endothelial cell expressing TEM8 in a subject detects pathological angiogenesis in the subject.

47. The method of claim 41, wherein the cell is an endothelial cell, and wherein detecting the presence of the endothelial cell expressing TEM8 in the subject detects a tumor in the subject.

48. A method of decreasing the binding of Anthrax protective antigen to a cell, comprising:
contacting the cell with an effective amount of the antibody or antigen binding fragment of claim 1 under conditions sufficient to form an immune complex, wherein formation of the immune complex decreases the binding of Anthrax protective antigen to the cell.

49. The method of claim 48, wherein contacting the cell with an effective amount of the antibody or antigen binding fragment comprises administering a therapeutically effective amount of the antibody or antigen binding fragment to a subject comprising the cell.

* * * * *

SEQUENCE LISTING

```
<160> NUMBER OF SEQ ID NOS: 28

<210> SEQ ID NO 1
<211> LENGTH: 117
<212> TYPE: PRT
<213> ORGANISM: Artificial Sequence
<220> FEATURE:
<223> OTHER INFORMATION: antibody sequence

<400> SEQUENCE: 1

Gln Val Gln Leu Val Gln Ser Gly Ala Glu Val Lys Lys Pro Gly Thr
1               5                   10                  15

Ser Val Lys Val Ser Cys Lys Val Pro Gly Tyr Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Gln Gly Arg Val Thr Ile Thr Gly Glu Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Thr Asp Tyr Met Phe Asp Tyr Trp Gly Gln Gly Thr Leu
            100                 105                 110

Val Thr Val Ser Ser
        115

<210> SEQ ID NO 2
<211> LENGTH: 107
<212> TYPE: PRT
<213> ORGANISM: Artificial Sequence
```

<220> FEATURE:
<223> OTHER INFORMATION: antibody sequence

<400> SEQUENCE: 2

```
Ser Ser Glu Leu Thr Gln Asp Pro Val Val Ser Val Ala Leu Gly Glu
1               5                   10                  15

Thr Val Ser Ile Thr Cys Gln Gly Asp Asn Leu Arg Asp Phe Tyr Ala
            20                  25                  30

Ser Trp Tyr Gln Gln Lys Pro Gly Gln Ala Pro Leu Leu Val Met Tyr
        35                  40                  45

Gly Lys Asn Arg Arg Pro Ser Gly Ile Pro Asp Arg Phe Ser Gly Ser
    50                  55                  60

Thr Ser Gly Asn Thr Leu Ser Leu Thr Ile Thr Gly Ala Gln Ala Glu
65                  70                  75                  80

Asp Glu Ala Asp Tyr Tyr Cys Ser Ser Arg Asp Asn Ser Lys His Val
                85                  90                  95

Val Phe Gly Gly Gly Thr Lys Val Thr Val Leu
            100                 105
```

<210> SEQ ID NO 3
<211> LENGTH: 117
<212> TYPE: PRT
<213> ORGANISM: Artificial Sequence
<220> FEATURE:
<223> OTHER INFORMATION: antibody sequence

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Asp Tyr Met Phe Asp Tyr Trp Gly Gln Gly Thr Leu
            100                 105                 110

Val Thr Val Ser Ser
        115
```

<210> SEQ ID NO 4
<211> LENGTH: 107
<212> TYPE: PRT
<213> ORGANISM: Artificial Sequence
<220> FEATURE:
<223> OTHER INFORMATION: antibody sequence

<400> SEQUENCE: 4

```
Ser Ser Glu Leu Thr Gln Asp Pro Val Val Ser Val Ala Leu Gly Glu
1               5                   10                  15

Thr Val Ser Ile Thr Cys Gln Gly Asp Asn Leu Arg Asp Phe Tyr Ala
            20                  25                  30

Ser Trp Tyr Gln Gln Lys Pro Gly Gln Ala Pro Leu Leu Val Met Tyr
        35                  40                  45
```

```
Gly Lys Asn Arg Arg Pro Ser Gly Ile Pro Asp Arg Phe Ser Gly Ser
     50                  55                  60

Thr Ser Gly Asn Thr Leu Ser Leu Thr Ile Thr Gly Ala Gln Ala Glu
 65                  70                  75                  80

Asp Glu Ala Asp Tyr Tyr Cys Ser Ser Arg Asp Asn Ser Lys His Val
                 85                  90                  95

Val Phe Gly Gly Gly Thr Lys Val Thr Val Leu
            100                 105
```

<210> SEQ ID NO 5
<211> LENGTH: 121
<212> TYPE: PRT
<213> ORGANISM: Artificial Sequence
<220> FEATURE:
<223> OTHER INFORMATION: antibody sequence

<400> SEQUENCE: 5

```
Glu Val Gln Leu Val Glu Ser Gly Gly Gly Val Val Gln Pro Gly Arg
 1               5                  10                  15

Ser Val Arg Leu Ser Cys Ala Ala Ser Gly Phe Thr Phe Ser Thr Tyr
             20                  25                  30

Thr Met His Trp Val Arg Gln Ala Pro Gly Lys Gly Leu Glu Trp Val
         35                  40                  45

Ala Ile Ile Ser Asn Asp Gly Ser Asn Lys Tyr Tyr Ala Asp Pro Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Gly Ser Ser Trp Tyr Arg Gly Asn Trp Phe Asp Pro Trp Gly
            100                 105                 110

Gln Gly Thr Leu Val Thr Val Ser Ser
        115                 120
```

<210> SEQ ID NO 6
<211> LENGTH: 108
<212> TYPE: PRT
<213> ORGANISM: Artificial Sequence
<220> FEATURE:
<223> OTHER INFORMATION: antibody sequence

<400> SEQUENCE: 6

```
Asp Ile Gln Met Thr Gln Ser Pro Ser Ser Leu Ser Ala Ser Val Gly
 1               5                  10                  15

Asp Arg Val Thr Ile Ala Cys Arg Ala Ser Gln Thr Ile Ser Arg Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Ser Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Phe Cys Gln Gln Tyr Ser Pro Pro Ile
                 85                  90                  95

Thr Phe Gly Gln Gly Thr Arg Leu Glu Ile Lys Arg
            100                 105
```

<210> SEQ ID NO 7

<211> LENGTH: 121
<212> TYPE: PRT
<213> ORGANISM: Artificial Seuqence
<220> FEATURE:
<223> OTHER INFORMATION: antibody sequence

<400> SEQUENCE: 7

```
Glu Val Gln Leu Val Glu Thr Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Thr Ser Gly Ser Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Gly Leu Arg Ser Asp Asp Thr Ala Val Tyr Tyr Cys
                85                  90                  95
Val Arg Asp Pro Gly Ser Pro Lys Trp Leu Ala Phe Asp Pro Trp Gly
            100                 105                 110
Gln Gly Thr Leu Val Thr Val Ser Ser
        115                 120
```

<210> SEQ ID NO 8
<211> LENGTH: 108
<212> TYPE: PRT
<213> ORGANISM: Artificial Sequence
<220> FEATURE:
<223> OTHER INFORMATION: antibody sequence

<400> SEQUENCE: 8

```
Asp Ile Gln Leu Thr Gln Ser Pro Ser Ser Leu Ser Ala Ser Val Gly
1               5                   10                  15
Asp Arg Val Thr Ile Thr Cys Arg Ala Ser Arg Ala Ile Ser Arg Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Ser Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Phe Cys Gln Gln Thr Tyr Ser Pro Pro Ile
                85                  90                  95
Thr Phe Gly Gln Gly Thr Arg Leu Glu Ile Lys Arg
            100                 105
```

<210> SEQ ID NO 9
<211> LENGTH: 1695
<212> TYPE: DNA
<213> ORGANISM: Homo sapiens

<400> SEQUENCE: 9

```
atggccacgg cggagcggag agccctcggc atcggcttcc agtggctctc tttggccact    60
ctggtgctca tctgcgccgg gcaagggggga cgcaggagg atgggggtcc agcctgctac   120
ggcggatttg acctgtactt cattttggac aaatcaggaa gtgtgctgca ccactggaat   180
gaaatctatt actttgtgga acagttggct cacaaattca tcagcccaca gttgagaatg   240
```

```
tcctttattg ttttctccac ccgaggaaca accttaatga aactgacaga agacagagaa    300
caaatccgtc aaggcctaga agaactccag aaagttctgc caggaggaga cacttacatg    360
catgaaggat ttgaaagggc cagtgagcag atttattatg aaaacagaca agggtacagg    420
acagccagcg tcatcattgc tttgactgat ggagaactcc atgaagatct ctttttctat    480
tcagagaggg aggctaatag gtctcgagat cttggtgcaa ttgtttactg tgttggtgtg    540
aaagatttca atgagacaca gctggccggg attgcggaca gtaaggatca tgtgtttccc    600
gtgaatgacg gctttcaggc tctgcaaggc atcatccact caattttgaa gaagtcctgc    660
atcgaaattc tagcagctga accatccacc atatgtgcag gagagtcatt tcaagttgtc    720
gtgagaggaa acggcttccg acatgcccgc aacgtggaca gggtcctctg cagcttcaag    780
atcaatgact cggtcacact caatgagaag ccctttctg tggaagatac ttatttactg    840
tgtccagcgc ctatcttaaa agaagttggc atgaaagctg cactccaggt cagcatgaac    900
gatggcctct cttttatctc cagttctgtc atcatcacca ccacacactg ttctgacggt    960
tccatcctgg ccatcgccct gctgatcctg ttcctgctcc tagccctggc tctcctctgg   1020
tggttctggc ccctctgctg cactgtgatt atcaaggagg tcctccacc ccctgccgag   1080 gagagtgagg aagaagatga tgatggtctg cctaagaaaa agtggccaac ggtagacgcc   1140
tcttattatg gtgggagagg cgttggaggc attaaaagaa tggaggttcg ttggggagaa   1200
aagggctcca cagaagaagg tgctaagttg gaaaaggcaa agaatgcaag agtcaagatg   1260
ccggagcagg aatatgaatt ccctgagccg cgaaatctca acaacaatat gcgtcggcct   1320
tcttcccccc ggaagtggta ctctccaatc aagggaaaac tcgatgcctt gtgggtccta   1380
ctgaggaaag gatatgatcg tgtgtctgtg atgcgtccac agccaggaga cacggggcgc   1440
tgcatcaact tcaccagggt caagaacaac cagccagcca agtacccact caacaacgcc   1500
taccacacct cctcgccgcc tcctgccccc atctacactc ccccacctcc tgcgccccac   1560
tgccctcccc cgccccccag cgcccctacc cctcccatcc cgtccccacc ttccaccctt   1620
ccccctcctc cccaggctcc acctcccaac agggcacctc ctccctcccg ccctcctcca   1680
aggccttctg tctag                                                    1695
```

<210> SEQ ID NO 10
<211> LENGTH: 564
<212> TYPE: PRT
<213> ORGANISM: Homo sapiens

<400> SEQUENCE: 10

Met Ala Thr Ala Glu Arg Arg Ala Leu Gly Ile Gly Phe Gln Trp Leu
1               5                   10                  15

Ser Leu Ala Thr Leu Val Leu Ile Cys Ala Gly Gln Gly Gly Arg Arg
                20                  25                  30

Glu Asp Gly Gly Pro Ala Cys Tyr Gly Gly Phe Asp Leu Tyr Phe Ile
            35                  40                  45

Leu Asp Lys Ser Gly Ser Val Leu His His Trp Asn Glu Ile Tyr Tyr
        50                  55                  60

Phe Val Glu Gln Leu Ala His Lys Phe Ile Ser Pro Gln Leu Arg Met
65                  70                  75                  80

Ser Phe Ile Val Phe Ser Thr Arg Gly Thr Thr Leu Met Lys Leu Thr
                85                  90                  95

Glu Asp Arg Glu Gln Ile Arg Gln Gly Leu Glu Glu Leu Gln Lys Val
            100                 105                 110

```
Leu Pro Gly Gly Asp Thr Tyr Met His Glu Gly Phe Glu Arg Ala Ser
            115                 120                 125

Glu Gln Ile Tyr Tyr Glu Asn Arg Gln Gly Tyr Arg Thr Ala Ser Val
130                 135                 140

Ile Ile Ala Leu Thr Asp Gly Glu Leu His Glu Asp Leu Phe Phe Tyr
145                 150                 155                 160

Ser Glu Arg Glu Ala Asn Arg Ser Arg Asp Leu Gly Ala Ile Val Tyr
                165                 170                 175

Cys Val Gly Val Lys Asp Phe Asn Glu Thr Gln Leu Ala Arg Ile Ala
            180                 185                 190

Asp Ser Lys Asp His Val Phe Pro Val Asn Asp Gly Phe Gln Ala Leu
        195                 200                 205

Gln Gly Ile Ile His Ser Ile Leu Lys Lys Ser Cys Ile Glu Ile Leu
    210                 215                 220

Ala Ala Glu Pro Ser Thr Ile Cys Ala Gly Glu Ser Phe Gln Val Val
225                 230                 235                 240

Val Arg Gly Asn Gly Phe Arg His Ala Arg Asn Val Asp Arg Val Leu
                245                 250                 255

Cys Ser Phe Lys Ile Asn Asp Ser Val Thr Leu Asn Glu Lys Pro Phe
            260                 265                 270

Ser Val Glu Asp Thr Tyr Leu Leu Cys Pro Ala Pro Ile Leu Lys Glu
        275                 280                 285

Val Gly Met Lys Ala Ala Leu Gln Val Ser Met Asn Asp Gly Leu Ser
    290                 295                 300

Phe Ile Ser Ser Ser Val Ile Ile Thr Thr Thr His Cys Ser Asp Gly
305                 310                 315                 320

Ser Ile Leu Ala Ile Ala Leu Leu Ile Leu Phe Leu Leu Leu Ala Leu
                325                 330                 335

Ala Leu Leu Trp Trp Phe Trp Pro Leu Cys Cys Thr Val Ile Ile Lys
            340                 345                 350

Glu Val Pro Pro Pro Ala Glu Glu Ser Glu Glu Glu Asp Asp Asp
        355                 360                 365

Gly Leu Pro Lys Lys Lys Trp Pro Thr Val Asp Ala Ser Tyr Tyr Gly
    370                 375                 380

Gly Arg Gly Val Gly Gly Ile Lys Arg Met Glu Val Arg Trp Gly Glu
385                 390                 395                 400

Lys Gly Ser Thr Glu Glu Gly Ala Lys Leu Glu Lys Ala Lys Asn Ala
                405                 410                 415

Arg Val Lys Met Pro Glu Gln Glu Tyr Glu Phe Pro Glu Pro Arg Asn
            420                 425                 430

Leu Asn Asn Asn Met Arg Arg Pro Ser Ser Pro Arg Lys Trp Tyr Ser
        435                 440                 445

Pro Ile Lys Gly Lys Leu Asp Ala Leu Trp Val Leu Leu Arg Lys Gly
    450                 455                 460

Tyr Asp Arg Val Ser Val Met Arg Pro Gln Pro Gly Asp Thr Gly Arg
465                 470                 475                 480

Cys Ile Asn Phe Thr Arg Val Lys Asn Asn Gln Pro Ala Lys Tyr Pro
                485                 490                 495

Leu Asn Asn Ala Tyr His Thr Ser Ser Pro Pro Ala Pro Ile Tyr
            500                 505                 510

Thr Pro Pro Pro Pro Ala Pro His Cys Pro Pro Pro Pro Ser Ala
        515                 520                 525

Pro Thr Pro Pro Ile Pro Ser Pro Pro Ser Thr Leu Pro Pro Pro Pro
```

Gln Ala Pro Pro Asn Arg Ala Pro Pro Ser Arg Pro Pro
545             550             555             560

Arg Pro Ser Val

<210> SEQ ID NO 11
<211> LENGTH: 351
<212> TYPE: DNA
<213> ORGANISM: Artificial Sequence
<220> FEATURE:
<223> OTHER INFORMATION: antibody sequence

<400> SEQUENCE: 11
caggtccagc tggtgcagtc tggggctgag gtgaagaagc ctgggacctc agtgaaggtc    60
tcctgcaagg ttcctggata caccttcagc agctatgcta tcagctgggt gcgacaggcc   120
cctggacaag gcttgagtg gatgggaggg atcatccta tctttggtac aacaaactac     180
gcacagaagt tccagggcag agtcacgatt accggggagg aatccacgag cacagtctac   240
atggagctga gcagcctgag atctgaggac acggccgtgt attactgtgc gagagatacg   300
gactacatgt tgactactg gggccaggga accctggtca ccgtgagctc a            351

<210> SEQ ID NO 12
<211> LENGTH: 321
<212> TYPE: DNA
<213> ORGANISM: Artificial Sequence
<220> FEATURE:
<223> OTHER INFORMATION: antibody sequence

<400> SEQUENCE: 12
tcttctgagc tgactcagga ccctgttgtg tctgtggcct tgggagagac agtcagtatc    60
acatgccaag agacaacct cagagacttt tatgcaagct ggtaccaaca gaagccagga    120
caggcccctc tactagtcat gtatggtaaa acaggcggc cctcaggat cccagaccga    180 ttctctggct ccacctcagg aaacacactt tccttgacca tcactgggc tcaggcggaa    240 gatgaggctg actattactg tagctcccgg gacaacagta agcatgtggt gttcggcggg   300
gggaccaagg tcaccgtcct a                                             321

<210> SEQ ID NO 13
<211> LENGTH: 351
<212> TYPE: DNA
<213> ORGANISM: Artificial Sequence
<220> FEATURE:
<223> OTHER INFORMATION: antibody sequence

<400> SEQUENCE: 13
caggtccagc tggtgcagtc tgggctgag gtgaagaagc tggggcctc agtgaaggtc      60 tcctgcaagg tttctggata caccttcagc agctatgcta tcagctgggt gcgacaggcc   120
cctggacaag gcttgagtg gatgggaggg atcatccta tctttggtac agcaaactac     180
gcacagaagt tccagggcag agtcacgatt accgcggacg aatccacgag cacagcctac   240
atggagctga gcagcctgag atctgaggac acggccgtgt attactgtgc gagagatacg   300
gactacatgt tgactactg gggccaggga accctggtca ccgtgagctc a             351

<210> SEQ ID NO 14
<211> LENGTH: 321
<212> TYPE: DNA
<213> ORGANISM: Artificial sequence
<220> FEATURE:

<223> OTHER INFORMATION: antibody sequence

<400> SEQUENCE: 14

| tcttctgagc tgactcagga ccctgttgtg tctgtggcct tgggagagac agtcagtatc | 60 |
| acatgccaag gagacaacct cagagacttt tatgcaagct ggtaccaaca gaagccagga | 120 |
| caggcccctc tactagtcat gtatggtaaa acaggcggc cctcagggat cccagaccga | 180 |
| ttctctggct ccacctcagg aaacacactt tccttgacca tcactgggc tcaggcggaa | 240 |
| gatgaggctg actattactg tagctcccgg gacaacagta agcatgtggt gttcggcggg | 300 |
| gggaccaagg tcaccgtcct a | 321 |

<210> SEQ ID NO 15
<211> LENGTH: 363
<212> TYPE: DNA
<213> ORGANISM: Artificial Sequence
<220> FEATURE:
<223> OTHER INFORMATION: antibody sequence

<400> SEQUENCE: 15

| gaggtgcagc tggtggagtc tgggggaggc gtggtccagc ctgggaggtc cgtgagactc | 60 |
| tcctgtgcag cctctggatt caccttcagt acctatacta tgcactgggt ccgccaggct | 120 |
| ccaggcaagg ggctggagtg ggtggcaatt atctcaaatg atggaagcaa taagtactac | 180 |
| gcagaccccg tgaggggccg attcaccatc tccagagaca attccaagaa cacgctgtat | 240 |
| ctgcaaatga acagcctgag agctgaggac acggctgtgt attactgtgt acgtggcagc | 300 |
| agctggtatc gcggaaattg gttcgacccc tggggccagg gaaccctggt caccgtgagc | 360 |
| tca | 363 |

<210> SEQ ID NO 16
<211> LENGTH: 324
<212> TYPE: DNA
<213> ORGANISM: Artificial Sequence
<220> FEATURE:
<223> OTHER INFORMATION: antibody sequence

<400> SEQUENCE: 16

| gacatccaga tgacccagtc tccatcctcc ctgtctgcat ctgtaggaga cagagtcacc | 60 |
| atcgcttgcc gggcaagtca gaccattagt aggtatttaa attggtatca gcagaaacca | 120 |
| gggaaagccc ctaagctcct gatctatgct gcatccagtt tgcaaagtgg ggtctcatca | 180 |
| aggttcagtg gcagtggatc tgggacagag ttcactctca ccatcagcag tctgcagcct | 240 |
| gaagattttg caacttattt ctgtcaacag acttacagtc cccgatcac cttcggccaa | 300 |
| gggacacgac tggagattaa acga | 324 |

<210> SEQ ID NO 17
<211> LENGTH: 363
<212> TYPE: DNA
<213> ORGANISM: Artificial Sequence
<220> FEATURE:
<223> OTHER INFORMATION: antibody sequence

<400> SEQUENCE: 17

| gaggtgcagc tggtggagac cggggctgag gtgaagaagc ctggggcctc agtgaaggtc | 60 |
| tcctgcaagg cttctggata caccttcacc ggctactata tgcactgggt gcgacaggcc | 120 |
| cctggacaag ggcttgagtg gatgggatgg atcaacccta ccagtggtag cacaaactat | 180 |
| gcacagaagt ttcagggcag ggtcaccatg accagggaca cgtccatcag cacagcctac | 240 |

```
atggagctga gcgggctgag atctgacgac actgccgtgt attactgtgt gagagatccg      300
ggttctccta gtggctggcc ttcgacccc tggggccagg gcaccctggt caccgtgagc      360
tca                                                                    363
```

<210> SEQ ID NO 18
<211> LENGTH: 324
<212> TYPE: DNA
<213> ORGANISM: Artificial Sequence
<220> FEATURE:
<223> OTHER INFORMATION: antibody sequence

<400> SEQUENCE: 18

```
gacatccagt tgacccagtc tccatcctcc ttgtctgctt ctgtaggaga cagagtcacc       60
atcacttgcc gggcaagtcg ggccattagt aggtatttaa attggtatca gcagaaacca      120
gggaaagccc ctaagctcct gatctatgct gcatccagtt tgcaaagtgg ggtctcatca      180
aggttcagtg gcagtggatc tgggacagag ttcactctca ccatcagcag tctgcagcct      240
gaagattttg caacttattt ctgtcaacag acttacagtc cccgatcac cttcggccaa      300 gggacacgac tggagattaa acgt                                              324
```

<210> SEQ ID NO 19
<211> LENGTH: 15
<212> TYPE: PRT
<213> ORGANISM: Artificial Sequence
<220> FEATURE:
<223> OTHER INFORMATION: Peptide linker

<400> SEQUENCE: 19

```
Gly Gly Gly Gly Ser Gly Gly Gly Gly Ser Gly Gly Gly Gly Ser
1               5                   10                  15
```

<210> SEQ ID NO 20
<211> LENGTH: 22
<212> TYPE: PRT
<213> ORGANISM: homo sapiens

<400> SEQUENCE: 20

```
Leu Leu Val Thr Ser Leu Leu Leu Cys Glu Leu Pro His Pro Ala Phe
1               5                   10                  15

Leu Leu Ile Pro Asp Thr
            20
```

<210> SEQ ID NO 21
<211> LENGTH: 236
<212> TYPE: PRT
<213> ORGANISM: homo sapiens

<400> SEQUENCE: 21

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

```
Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys Lys Asp Pro Lys
225                 230                 235

<210> SEQ ID NO 22
<211> LENGTH: 69
<212> TYPE: PRT
<213> ORGANISM: homo sapiens

<400> SEQUENCE: 22

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 23
<211> LENGTH: 67
<212> TYPE: PRT
<213> ORGANISM: homo sapiens

<400> SEQUENCE: 23

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
        50                  55                  60

Trp Val Arg
65

<210> SEQ ID NO 24
<211> LENGTH: 112
```

```
<212> TYPE: PRT
<213> ORGANISM: homo sapiens

<400> SEQUENCE: 24

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 25
<211> LENGTH: 84
<212> TYPE: PRT
<213> ORGANISM: homo sapiens

<400> SEQUENCE: 25

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
                20                  25                  30

Arg Pro Glu Ala Cys Arg Pro Ala Ala Gly Gly Ala Val His Thr Arg
            35                  40                  45

Gly Leu Asp Phe Ala Cys Asp Ile Tyr Ile Trp Ala Pro Leu Ala Gly
            50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 26
<211> LENGTH: 40
<212> TYPE: PRT
<213> ORGANISM: homo sapiens

<400> SEQUENCE: 26

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
                20                  25                  30

Arg Asp Phe Ala Ala Tyr Arg Ser
            35                  40

<210> SEQ ID NO 27
<211> LENGTH: 42
<212> TYPE: PRT
<213> ORGANISM: homo sapiens

<400> SEQUENCE: 27

Lys Arg Gly Arg Lys Lys Leu Leu Tyr Ile Phe Lys Gln Pro Phe Met
1               5                   10                  15
```

```
Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 28
<211> LENGTH: 47
<212> TYPE: PRT
<213> ORGANISM: homo sapiens

<400> SEQUENCE: 28

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
            35                  40                  45
```